United States Patent
Springer et al.

(10) Patent No.: US 9,439,893 B2
(45) Date of Patent: Sep. 13, 2016

(54) 1-(5-TERT-BUTYL-2-PHENYL-2H-PYRAZOL-3-YL)-3-[2-FLUORO-4-(1-METHYL-2-OXO-2,3-DIHYDRO-1H-IMIDAZO[4,5-B]PYRIDIN-7-YLOXY)-PHENYL]-UREA AND RELATED COMPOUNDS AND THEIR USE IN THERAPY

(71) Applicants: CANCER RESEARCH TECHNOLOGY LIMITED, London (GB); INSTITUTE OF CANCER RESEARCH: ROYAL CANCER HOSPITAL (THE), London (GB)

(72) Inventors: Caroline Springer, Sutton (GB); Ion Niculescu-Duvaz, Sutton (GB); Richard Marais, London (GB); Dan Niculescu-Duvaz, Sutton (GB); Alfonso Zambon, Sutton (GB); Delphine Menard, Allonnes (FR)

(73) Assignees: CANCER RESEARCH TECHNOLOGY LIMITED, London (GB); INSTITUTE OF CANCER RESEARCH: ROYAL CANCER HOSPITAL (THE), London (GB)

(*) Notice: Subject to any disclaimer, the term of this patent is extended or adjusted under 35 U.S.C. 154(b) by 0 days.

(21) Appl. No.: 14/813,658

(22) Filed: Jul. 30, 2015

(65) Prior Publication Data

US 2016/0030405 A1 Feb. 4, 2016

Related U.S. Application Data

(63) Continuation of application No. 14/331,653, filed on Jul. 15, 2014, now Pat. No. 9,120,789, which is a continuation of application No. 13/520,613, filed as application No. PCT/GB2011/000106 on Jan. 27, 2011, now Pat. No. 8,815,896.

(60) Provisional application No. 61/300,085, filed on Feb. 1, 2010.

(51) Int. Cl.
| | |
|---|---|
| *A61K 31/437* | (2006.01) |
| *A61K 31/444* | (2006.01) |
| *C07D 471/04* | (2006.01) |
| *A61K 31/4353* | (2006.01) |
| *C07D 401/02* | (2006.01) |

(52) U.S. Cl.
CPC ......... *A61K 31/437* (2013.01); *A61K 31/4353* (2013.01); *C07D 401/02* (2013.01); *C07D 471/04* (2013.01)

(58) Field of Classification Search
CPC .................. A61K 31/444; A61K 31/437
USPC ........................................... 514/303
See application file for complete search history.

(56) References Cited

U.S. PATENT DOCUMENTS

| | | |
|---|---|---|
| 4,082,845 A | 4/1978 | Saari et al. |
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,521,073 A | 5/1996 | Davis et al. |
| 5,877,020 A | 3/1999 | Alitalo et al. |
| 5,879,672 A | 3/1999 | Davis et al. |
| 5,882,864 A | 3/1999 | An et al. |
| 6,030,831 A | 2/2000 | Godowski et al. |
| 6,218,529 B1 | 4/2001 | An et al. |
| 6,258,809 B1 | 7/2001 | Rajagopalan et al. |
| 6,492,529 B1 | 12/2002 | Kapadia et al. |
| 7,625,922 B2 | 12/2009 | Niculescu-Duvaz et al. |

(Continued)

FOREIGN PATENT DOCUMENTS

| | | |
|---|---|---|
| EP | 1724268 A1 | 11/2006 |
| JP | 55665863 A | 6/1981 |

(Continued)

OTHER PUBLICATIONS

Suijkerbuijk et al., Journal of Medicinal Chemistry (2010), 53(7), 2741-2756.*
Abasolo et al.,"Kinetic study on the anelation of heterocycles. 2. pyrido[2,3-b]pyrazine and pyrido[3,4-b]pyrazine derivatives synthesized by the Hinsberg reaction," J Heterocyclic Chem. 27(2):157-162 (1990).
Adams et al., "Roles of ephrinB ligands and EphB receptors in cardiovascular development: demarcation of arterial/venous domains, vascular morphogenesis, and sprouting angiogenesis," Genes Dev. 13(3):295-306 (1999).

(Continued)

*Primary Examiner* — Niloofar Rahmani
(74) *Attorney, Agent, or Firm* — Clark & Elbing LLP

(57) ABSTRACT

The present invention pertains generally to the field of therapeutic compounds, and more specifically to certain compounds of the following formula (for convenience, collectively referred to herein as "IP compounds"), which, inter alia, are useful in the treatment of cancer, e.g., cancer characterised by (e.g., driven by) mutant RAS ("mutant RAS cancer"). The present invention also pertains to pharmaceutical compositions comprising such compounds, and the use of such compounds and compositions in the treatment of cancer, e.g., mutant RAS cancer.

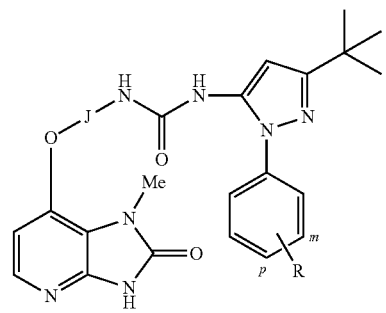

29 Claims, 10 Drawing Sheets

(56) References Cited

U.S. PATENT DOCUMENTS

| | | | |
|---|---|---|---|
| 7,951,819 B2 | 5/2011 | Niculescu-Duvaz et al. |
| 8,198,279 B2 | 6/2012 | Springer et al. |
| 8,383,816 B2 | 2/2013 | Niculescu-Duvaz et al. |
| 8,546,387 B2 | 10/2013 | Springer et al. |
| 8,815,896 B2 | 8/2014 | Springer et al. |
| 8,912,191 B2 | 12/2014 | Springer et al. |
| 9,120,789 B2 | 9/2015 | Springer et al. |
| 9,155,737 B2 | 10/2015 | Springer et al. |
| 2004/0082583 A1 | 4/2004 | Cheung et al. |
| 2007/0287838 A1 | 12/2007 | Niculescu-Duvaz et al. |
| 2008/0113967 A1 | 5/2008 | Flynn et al. |
| 2009/0325945 A1 | 12/2009 | Niculescu-Duvaz et al. |
| 2010/0298320 A1 | 11/2010 | Springer et al. |
| 2011/0053946 A1 | 3/2011 | Niculescu-Duvaz et al. |
| 2012/0238568 A1 | 9/2012 | Springer et al. |
| 2012/0283288 A1 | 11/2012 | Springer et al. |

FOREIGN PATENT DOCUMENTS

| | | |
|---|---|---|
| JP | 55738777 A | 3/1982 |
| WO | WO-98/13350 A1 | 4/1998 |
| WO | WO-99/16438 A1 | 4/1999 |
| WO | WO-99/21859 A1 | 5/1999 |
| WO | WO-00/35436 A2 | 6/2000 |
| WO | WO-00/40235 A2 | 7/2000 |
| WO | WO-00/45435 A1 | 8/2000 |
| WO | WO-01/05392 A2 | 1/2001 |
| WO | WO-01/36383 A1 | 5/2001 |
| WO | WO-01/46196 A1 | 6/2001 |
| WO | WO-02/102367 A1 | 12/2002 |
| WO | WO-03/056036 A2 | 7/2003 |
| WO | WO-2004/014300 A2 | 2/2004 |
| WO | WO-2004/083458 A1 | 9/2004 |
| WO | WO-2004/110452 A1 | 12/2004 |
| WO | WO-2006/003378 A1 | 1/2006 |
| WO | WO-2006/024834 A1 | 3/2006 |
| WO | WO-2006/040568 A1 | 4/2006 |
| WO | WO-2006/043090 A1 | 4/2006 |
| WO | WO-2006/067466 A2 | 6/2006 |
| WO | WO-2007/059202 A2 | 5/2007 |
| WO | WO-2007/064872 A2 | 6/2007 |
| WO | WO-2007/067444 A1 | 6/2007 |
| WO | WO-2007/076092 A2 | 7/2007 |
| WO | WO-2007/125330 A1 | 11/2007 |
| WO | WO-2008/009700 A1 | 1/2008 |
| WO | WO-2008/044688 A1 | 4/2008 |
| WO | WO-2009/007934 A2 | 1/2009 |
| WO | WO-2009/077766 A1 | 6/2009 |
| WO | WO-2009/130487 A1 | 10/2009 |
| WO | WO-2010/038085 A2 | 4/2010 |
| WO | WO-2010/038086 A2 | 4/2010 |
| WO | WO-2010/067130 A1 | 6/2010 |
| WO | WO-2010/067131 A1 | 6/2010 |
| WO | WO-2010/112936 A1 | 10/2010 |
| WO | WO-2011/004276 A1 | 1/2011 |
| WO | WO-2011/028540 A1 | 3/2011 |
| WO | WO-2011/070368 A1 | 6/2011 |
| WO | WO-2011/070369 A1 | 6/2011 |
| WO | WO-2011/092469 A1 | 8/2011 |
| WO | WO-2011/121366 A1 | 10/2011 |
| WO | WO-2011/124923 A2 | 10/2011 |
| WO | WO-2011/124930 A1 | 10/2011 |
| WO | WO-2011/158039 A1 | 12/2011 |
| WO | WO-2011/158042 A2 | 12/2011 |
| WO | WO-2011/158044 A2 | 12/2011 |
| WO | WO-2012/008564 A1 | 1/2012 |
| WO | WO-2012/149547 A1 | 11/2012 |
| WO | WO-2012/177725 A1 | 12/2012 |
| WO | WO-2013/001372 A2 | 1/2013 |
| WO | WO-2013/033133 A1 | 3/2013 |
| WO | WO-2013/050756 A1 | 4/2013 |
| WO | WO-2013/050757 A1 | 4/2013 |
| WO | WO-2014/027209 A1 | 2/2014 |
| WO | WO-2014/033446 A1 | 3/2014 |
| WO | WO-2014/033447 A2 | 3/2014 |
| WO | WO-2014/033448 A1 | 3/2014 |
| WO | WO-2014/033449 A1 | 3/2014 |
| WO | WO-2014/076484 A1 | 5/2014 |
| WO | WO-2014/140582 A1 | 9/2014 |
| WO | WO-2014/162121 A1 | 10/2014 |

OTHER PUBLICATIONS

Akula et al.,"Raf promotes human herpesvirus-8 (HHV-8/KSHV) infection," Oncogene. 23(30):5227-5241 (2004).

Alon et al., "Vascular endothelial growth factor acts as a survival factor for newly formed retinal vessels and has implications for retinopathy of prematurity," Nat Med. 1(10):1024-1028 (1995).

Ananthanarayanan et al., "Reaction of azides in presence of aluminium chloride," Indian J Chem. 27B:156-7 (1988).

Anastasaki et al "Continual low-level MEK inhibition ameliorates cardio-facio-cutaneous phenotypes in zebrafish," Dis Model Mech. 5(4):546-552 (2012).

Angerer et al., "Demonstration of tissue-specific gene expression by in situ hybridization," Methods Enzymol. 152:649-61 (1987).

Antony et al.,"C-RAF Mutations confer resistance to RAF inhibitors," Cancer Res. 73(15):4840-4851 (2013).

Arcaini et al., "The BRAF V600E mutation in hairy cell leukemia and other mature B-cell neoplasms," Blood. 119(1):188-191 (2012) (5 pages).

Asrih et al., "Role of mitogen-activated protein kinase pathways in multifactorial adverse cardiac remodeling associated with metabolic syndrome," Mediators Inflamm. 2013:367245 (2013) (12 pages).

Auvray et al., "Preparation and nucleophilic substitution of (E)-1-bromo-2-phenylsulfonyl-2-alkenes and 3-acetoxy-2-phenylsulfonyl-1-alkenes," Tetrahedron. 44(19):6095-106 (1988).

Avenoza et al., "New efficient synthesis of 4-amino-3-arylphenols," Synthesis. 671-674 (1995).

Badalian-Very et al., "Recent advances in the understanding of Langerhans cell histiocytosis," Br J Haematol. 156(2): 163-172 (2012).

Ballesteros et al., "Study of the catalytic properties of tris (3,6-dioxaheptyl) amine (tda-1) in heteroaromatic nucleophilic substitution of chloropyridines and their n-oxides," Tetrahedron. 43(11):2557-64 (1987).

Bart et al., "Development of novel, highly potent inhibitors of V-RAF murine sarcoma viral oncogene homologue B1 (BRAF): increasing cellular potency through optimization of a distal heteroaromatic group," J Med Chem. 53:2741-56 (2010).

Bates et al., "A new synthesis of pyrazinol[2,3-c]isoquinolines," Aust J Chem. 43(1): 179-184 (1990).

Belgore et al., "Localisation of members of the vascular endothelial growth factor (VEGF) family and their receptors in human atherosclerotic arteries," J Clin Pathol. 57(3): 266-272 (2004).

Benn et al., "Hepatitis B virus HBx protein activates Ras-GTP complex formation and establishes a Ras, Raf, MAP kinase signaling cascade," Proc Natl Acad Sci USA. 91(22): 10350-10354 (1994).

Berge et al., "Pharmaceutical salts," J Pharm Sci. 66(1):1-19 (1977).

Bergman et al., "Synthesis of pyridopyrazino[2,3-b]indoles and 10H-indolo[3,2-g]pteridins," Recl Trav Chim Pays-Bas. 115(1): 31-36 (1996).

Berry et al., "TNF-alpha in asthma," Curr Opin Pharmacol. 7(3): 279-282 (2007).

Bhatt et al., "Preparation of N'-2-phenyl-4-quinolinoyl-N3-aryl thioureas," J Instit Chem (India). 52:113-4 (1980).

Bianchi et al., "Compounds with antiulcer and antisecretory activity," Eur J Med Chem. 16(4):321-6 (1981).

Borthakur et al., "New direct synthesis of thioamides from carboxylic acids," Tetrahedron Letters. 36(37):6745-6 (1995).

Bos, "Ras oncogenes in human cancer: a review," Cancer Res. 49(17):4682-9 (1989).

Broekhof et al., "Novel applications of alpha-aminosubstituted diphenylphosphine oxides. The conversion of aldehydes into alpha-aminomethylketones," Tetrahedron Lett. 22(29):2799-802 (1981).

Brooks et al., "Integrin alpha v beta 3 antagonists promote tumor regression by inducing apoptosis of angiogenic blood vessels," Cell. 79(7): 1157-64 (1994).

(56) References Cited

OTHER PUBLICATIONS

Brose et al., "BRAF and RAS mutations in human lung cancer and melanoma," Cancer Res. 62(23):6997-7000 (2002).
Bruckner et al.,"Tyrosine phosphorylation of transmembrane ligands for Eph receptors," Science. 275(5306):1640-3 (1997).
Bruder et al., "Serum-, TPA-, and Ras-induced expression from Ap-1/Ets-driven promoters requires Raf-1 kinase," Genes Dev. 6(4):545-56 (1992).
Byeon et al., "The role of Src kinase in macrophage-mediated inflammatory responses," Mediators Inflamm. 2012:512926 (2012) (19 pages).
Calhoun et al., "BRAF and FBXW7 (CDC4, FBW7, AGO, SEL10) mutations in distinct subsets of pancreatic cancer: potential therapeutic targets," Am J Pathol. 163(4): 1255-1260 (2003).
Cantrell, "GTPases and T cell activation," Immunol Rev.192:122-30 (2003).
Chan et al., "Regulation of antigen receptor signal transduction by protein tyrosine kinases," Curr Opin Immunol. 8(3):394-401 (1996).
Chapman et al., "Improved survival with vemurafenib in melanoma with BRAF V600E mutation," N Engl J Med. 364(26): 2507-2516 (2011).
Ciampi et al., "Oncogenic AKAP9-BRAF fusion is a novel mechanism of MAPK pathway activation in thyroid cancer," J Clin Invest. 115(1): 94-101 (2005).
Clare et al., "Protease inhibitors: synthesis of a series of bacterial collagenase inhibitors of the sulfonyl amino acyl hydroxamate type," J Med Chem. 44(13):2253-8 (2001).
Clark-Lewis et al., "Quinoxaline derivatives. Part IV. Dihydro-oxo-1 : 4 : 5-triazanaphthalenecarboxyureides and related spiroHydantoins," J Chem Soc. 430-439 (1957).
Cohen et al., "Lack of BRAF mutation in primary uveal melanoma," Invest Ophthalmol Vis Sci. 44(7):2876-8 (2003).
Colville-Nash et al., "Angiogenesis and rheumatoid arthritis: pathogenic and therapeutic implications," Ann Rheum Dis. 51(7):919-25 (1992).
Comins et al., "Grignard addition to 1-acyl salts of chiral 4-alkoxypyridines. A new enantioselective preparation of 2-alkyl-2,3-dihydro-4-pyridones," Tetrahedron Lett. 35(40):7343-6 (1994).
Cooper, "Membrane-associated tyrosine kinases as molecular switches," Semin Cell Biol. 5(6):377-87 (1994).
Corcoran et al., "BRAF gene amplification can promote acquired resistance to MEK inhibitors in cancer cells harboring the BRAF V600E mutation," Sci Signal. 3(149):ra84 (2010) (10 pages).
Correia, "Reaction of phenylglyoxal with aniline under acidic conditions," J Org Chem 43(17):3394-6 (1978).
Coulthard et al., "p38(MAPK): stress responses from molecular mechanisms to therapeutics," Trends Mol Med. 15(8): 369-379 (2009).
Courtneidge et al., "The Src family of protein tyrosine kinases: regulation and functions," Dev Suppl. 57-64 (1993).
Cowely et al., "Activation of MAP kinase kinase is necessary and sufficient for PC12 differentiation and for transformation of NIH 3T3 cells," Cell. 77(6):841-52 (1994).
Cuadrado et al., "Mechanisms and functions of p38 MAPK signalling," Biochem J. 429(3): 403-417 (2010).
Cushman et al., "19F NMR studies on the mechanism of riboflavin synthase. Synthesis of 6-(Trifluoromethyl)-7-oxo-8-(D-ribityl)Iumazine and 6-(Trifluoromethyl)-7-methyl-8-(D-ribityl)Iumazine," J Org Chem. 57(21): 5630-5643 (1992).
Damodar Reddy et al., 2001, "Role of MAP kinase pathways in primitive neuroectodermal tumors," Anticancer Res. 21(4A): 2733-2738 (2001).
Davies et al., "Mutations of the BRAF gene in human cancer," Nature. 417(6892):949-54 (2002).
Davis et al., "Isolation of angiopoietin-1, a ligand for the TIE2 receptor, by secretion-trap expression cloning," Cell. 87(7):1161-9 (1996).

Davis et al., "Raf and mitogen-activated protein kinase regulate stellate cell collagen gene expression," J Biol Chem. 271(19): 11039-11042 (1996) (5 pages).
Denekamp, "Review article: angiogenesis, neovascular proliferation and vascular pathophysiology as targets for cancer therapy," Br J Radiol. 66(783):181-96 (1993).
Dettner et al., "Chemical defense of giant springtail *Tetrodontophora bielanensis* (Waga) (Insecta: *Collembola*)," J Chem Ecol. 22(5): 1051-1074 (1996).
Dhomen et al., "Oncogenic Braf induces melanocyte senescence and melanoma in mice," Cancer Cell. 15(4): 294-303 (2009).
Dickson et al., "Raf functions downstream of Ras1 in the Sevenless signal transduction pathway," Nature. 360(6404):600-3 (1992).
Downward, "Targeting RAS signalling pathways in cancer therapy," Nat Rev Cancer. 3(1):11-22 (2003).
Dubey et al., "Structure and reactions of monoanils obtained from 2,3-pyridinediamines," Indian J Chem. 40B(5): 361-367 (2001).
DuBois, "Amination of aryl sulfamate esters. A convenient general synthesis of aliphatic sulfamides," J Org Chem. 45:5373-5 (1980).
Ellis et al., "VEGF-targeted therapy: mechanisms of anti-tumour activity," Nat Rev Cancer. 8(8):579-591 (2008).
Falchook et al., "RAF inhibitor dabrafenib (GSK2118436) is active in melanoma brain metastases, multiple BRAF genotypes and diverse cancers" NIH Public Access Author Manuscript 20 pages Jul. 24, 2014, published in final edited form as "Dabrafenib in patients with melanoma, untreated brain metastases, and other solid tumours: a phase 1 dose-escalation trial," Lancet. 379(9829):1893-1901 (2012).
Fernandez-Medarde et al., "Ras in cancer and developmental diseases," Genes Cancer. 2(3):344-358 (2011).
Fidler et al., "The implications of angiogenesis for the biology and therapy of cancer metastasis," Cell. 79(2):185-8 (1994).
Flaherty et al., "Inhibition of mutated, activated BRAF in metastatic melanoma," N Engl J Med. 363(9): 809-819 (2010).
Folkman et al., "Angiogenesis," J Biol Chem. 267(16):10931-4 (1992).
Folkman, "Angiogenesis and angiogenesis inhibition: An overview," EXS. 79:1-8 (1997).
Folkman, "Angiogenesis in cancer, vascular, rheumatoid and other disease," Nat Med. 1(1):27-31 (1995).
Folkman, "The role of angiogenesis in tumor growth," Semin Cancer Biol. 3(2):65-71 (1992).
Fourrey et al., "Preparation of stable 1,4-dihydropyrazines," J Chem Soc., Perkins Transactions 1: Org. and Bio. Chem. 8:1841-3 (1987).
Friedlander et al., "Definition of two angiogenic pathways by distinct alpha v integrins," Science. 270(5241):1500-2 (1995).
Fujita et al., "ERK and p38 mediate high-glucose-induced hypertrophy and TGF-beta expression in renal tubular cells," Am J Physiol Renal Physiol. 286(1): F120-6 (2004).
Fukuda et al., "Epstein-Barr virus latent membrane protein 2A mediates transformation through constitutive activation of the Ras/PI3-K/Akt Pathway," J Virol. 81(17): 9299-9306 (2007).
Gale et al., "Growth factors acting via endothelial cell-specific receptor tyrosine kinases: VEGFs, angiopoietins, and ephrins in vascular development," Genes Dev. 13(9):1055-66 (1999).
Galons,"Cyclisation indolique selon Bischler en presence d'acides de Lewis," J Heterocyclic Chemistry. 18:561-63 (1981).
Garnett et al., "Guilty as charged: B-RAF is a human oncogene," Cancer Cell. 6(4):313-9 (2004).
Gaudi et al., "Molecular bases of cutaneous and uveal melanomas," Patholog Res Int. 2011:159421 (2011) (8 pages).
Genot et al.,"Ras regulation and function in lymphocytes," Curr Opin Immunol. 12(3):289-94 (2000).
Geppert et al., "Lipopolysaccharide signals activation of tumor necrosis factor biosynthesis through the ras/raf-1/MEK/MAPK pathway," Mol Med. 1(1): 93-103 (1994).
Giannotti et al., "New dibenzothiadiazepine derivatives with antidepressant activities," J Med Chem 34(4):1356-62 (1991).
Giardina et al., "Replacement of the quinoline system in 2-phenyl-4-quinolinecarboxamide NK-3 receptor antagonists," Farmaco. 54(6):364-74 (1999).

(56) References Cited

OTHER PUBLICATIONS

Girotti et al., "Inhibiting EGF receptor or SRC family kinase signaling overcomes BRAF inhibitor resistance in melanoma," Cancer Discov. 3(2): 158-167 (2013).
Glinka, "Synthesis and structure of new hetercyclic systems containing the sulfamide group," Pol J Chem. 65:2053-5 (1991).
Golub et al., "Molecular classification of cancer: class discovery and class prediction by gene expression monitoring," Science. 286(5439):531-7 (1999).
Gorden et al., "Analysis of BRAF and N-RAS mutations in metastatic melanoma tissues," Cancer Res. 63(14):3955-7 (2003).
Graf et al., "Mitogen-activated protein kinase activation is involved in platelet-derived growth factor-directed migration by vascular smooth muscle cells," Hypertension. 29(1 Pt. 2): 334-339 (1997).
Gray-Schopfer et al., "Melanoma biology and new targeted therapy," Nature. 445(7130):851-7 (2007).
Greger et al., "Combinations of BRAF, MEK, and PI3K/mTOR inhibitors overcome acquired resistance to the BRAF inhibitor GSK2118436 dabrafenib, mediated by NRAS or MEK mutations," Mol Cancer Ther. 11(4): 909-920 (2012).
Grosios et al., "Angiogenesis inhibition by the novel VEGF receptor tyrosine kinase inhibitor, PTK787/ZK222584, causes significant anti-arthritic effects in models of rheumatoid arthritis," Inflamm Res. 53(4): 133-142 (2004).
Guarna et al., "Synthesis of a new enantiopure bicyclic gamma/delta-amino acid (BTKa) derived from tartaric acid and alpha-amino acetophenone," Tetrahedron. 58(49):9865-70 (2002).
Haase et al., "A role for mitogen-activated protein kinase activation by integrins in the pathogenesis of psoriasis," J Clin Invest. 108(4): 527-536 (2001).
Haesslein et al., "Recent advances in cyclin-dependent kinase inhibition. Purine-based derivatives as anti-cancer agents. Roles and perspectives for the future," Curr Top Med Chem. 2(9):1037-50 (2002).
Hammond et al., "Structure-activity relationships in a series of NPY Y5 antagonists: 3-amido-9-ethylcarbazoles, core-modified analogues and amide isosteres," Bioorg Med Chem Lett. 13(12):1989-92 (2003).
Haroche et al., "High prevalence of BRAF V600E mutations in Erdheim-Chester disease but not in other non-Langerhans cell histiocytoses," Blood. 120(3): 2700-2703 (2012) (5 pages).
Heidorn et al., "Kinase-dead BRAF and oncogenic RAS cooperate to drive tumor progression through CRAF," Cell. 140(2): 209-221 (2010).
Helbling et al., "The receptor tyrosine kinase EphB4 and ephrin-B ligands restrict angiogenic growth of embryonic veins in Xenopus laevis," Development. 127(2):269-78 (2000).
Hirayama et al., "Design, synthesis and biological activity of YM-60828 derivatives: potent and orally-bioavailable factor Xa inhibitors based on naphthoanilide and naphthalensulfonanilide templates," Bioorg Med Chem. 10(8):2597-610 (2002).
Holland et al., "Bidirectional signalling through the EPH-family receptor Nuk and its transmembrane ligands," Nature. 383(6602):722-5 (1996).
Hu et al., "Mutation that blocks ATP binding creates a pseudokinase stabilizing the scaffolding function of kinase suppressor of Ras, CRAF and BRAF," Proc Natl Acad Sci USA. 108(15): 6067-6072 (2011) (9 pages).
Hwang et al., "Over-expression of c-raf-1 proto-oncogene in liver cirrhosis and hepatocellular carcinoma," Hepatol Res. 29(2): 113-121 (2004).
Ingber et al., "Synthetic analogues of fumagillin that inhibit angiogenesis and suppress tumour growth," Nature. 348(6301):555-7 (1990).
Inoue et al., "Vascular endothelial growth factor (VEGF) expression in human coronary atherosclerotic lesions: possible pathophysiological significance of VEGF in progression of atherosclerosis," Circulation. 98(20): 2108-2116 (1998).
International Preliminary Report on Patentability for International Application No. PCT/GB2005/004081, issued Apr. 24, 2007 (8 pages).
International Preliminary Report on Patentability for International Application No. PCT/GB2007/001534, issued Oct. 28, 2008 (10 pages).
International Preliminary Report on Patentability for International Application No. PCT/GB2008/004208, issued Jun. 22, 2010 (6 pages).
International Preliminary Report on Patentability for International Application No. PCT/GB2009/001077, issued Oct. 26, 2010 (6 pages).
International Preliminary Report on Patentability for International Application No. PCT/GB2011/000106, issued Aug. 7, 2012 (7 pages).
International Search Report and Written Opinion for International Application No. PCT/GB2005/004081, mailed Feb. 2, 2006 (12 pages).
International Search Report and Written Opinion for International Application No. PCT/GB2008/004208, mailed Mar. 5, 2009 (7 pages).
International Search Report and Written Opinion for International Application No. PCT/GB2009/001077, mailed Sep. 21, 2009 (8 pages).
International Search Report and Written Opinion for International Application No. PCT/GB2011/000106, mailed Mar. 18, 2011 (10 pages).
International Search Report and Written Opinion for International Application No. PCT/GB2014/053489, mailed Jan. 15, 2015 (11 pages).
International Search Report and Written Opinion for International Application No. PCT/GB2014/053490, mailed Jan. 26, 2015 (10 pages).
International Search Report for International Application No. PCT/GB2007/001534, mailed Sep. 6, 2007 (4 pages).
Ishii et al., "First synthesis and reactivities of isolable dithiiranes and their 1-oxides," Bulletin of the Chemical Society of Japan. 70:509-23 (1997).
Itaya et al., "Syntheses of the marine ascidian purine aplidiamine and its 9-beta-d-ribofuranoside," Tetrahedron Lett. 39:4695-6 (1998).
Jaffee et al., "Inhibition of MAP kinase kinase (MEK) results in an anti-inflammatory response in vivo," Biochem Biophys Res Commun. 268(2): 647-651 (2000).
Janvier et al., "Ammonium chloride-promoted four-component synthesis of pyrrolo[3,4-b]pyridin-5-one," J Am Chem Soc. 124(11):2560-7 (2002).
Jessen et al., "MEK inhibition exhibits efficacy in human and mouse neurofibromatosis tumors," J Clin Invest 123(1): 340-347 (2013).
Ji et al., "ERK MAP kinase activation in superficial spinal cord neurons induces prodynorphin and NK-1 upregulation and contributes to persistent inflammatory pain hypersensitivity," J Neurosci. 22(2): 478-85 (2002).
Jo et al., "MEK inhibitor, U0126, attenuates cisplatin-induced renal injury by decreasing inflammation and apoptosis," Kidney Int. 67(2): 458-466 (2005).
Johnson et al., "Preparation and reactions of sulfonimidoyl chlorides," J Org Chem. 44(13):2055-61 (1979).
Johnson et al., "The role of MKK1/2 kinase activity in human cytomegalovirus infection," J Gen Virol. 82(Pt 3): 493-497 (2001).
Jursic, "Synthetic application of micellar catalysis. williamson's synthesis of ethers," Tetrahedron. 44(21):6677-80 (1988).
Kahlon et al., "Angiogenesis in atherosclerosis," Can J Cardiol. 8(1):60-4 (1992).
Kam et al.,"TNF-alpha antagonists for the treatment of Crohn's disease," Expert Opin Pharmacother. 1(4): 615-622 (2000).
Karim et al.,"Impaired inflammatory pain and thermal hyperalgesia in mice expressing neuron-specific dominant negative mitogen activated protein kinase kinase (MEK)," Mol Pain. 2: 2 (2006) (10 pages).
Keffer et al., "Transgenic mice expressing human tumour necrosis factor: a predictive genetic model of arthritis," EMBO J. 10(13): 4025-4031 (1991).

(56) References Cited

OTHER PUBLICATIONS

Kolch et al., "Raf-1 protein kinase is required for growth of induced NIH/3T3 cells," Nature. 349(6308):426-8 (1991).
Kotoula et al., "Mutational analysis of the BRAF, RAS and EGFR genes in human adrenocortical carcinomas," Endocr Relat Cancer. 16(2): 565-572 (2009).
Lala et al., "Role of nitric oxide in tumor progression: lessons from experimental tumors," Cancer Metastasis Rev. 17(1):91-106 (1998).
Leese et al., "Polyazanaphthalenes. Part I. Some derivatives of 1:4:5-triazanaphthalene and quinoxaline," J Chem Soc. 303-309 (1955).
Lemonnier et al., "Role of N-cadherin and protein kinase C in osteoblast gene activation induced by the S252W fibroblast growth factor receptor 2 mutation in Apert craniosynostosis," J Bone Miner Res. 16(5):832-45 (2001).
Li et al., "Activation of NF-kappaB via a Src-dependent Ras-MAPK-pp90rsk pathway is required for Pseudomonas aeruginosa-induced mucin overproduction in epithelial cells," Proc Natl Acad Sci USA. 95(10): 5718-5723 (1998).
Lin et al., "VEGF and its receptor-2 involved in neuropathic pain transmission mediated by P2X2(/)3 receptor of primary sensory neurons," Brain Res Bull. 83(5):284-291 (2010).
Lindauer et al., "Dasatinib," Recent Results Cancer Res. 184: 83-102 (2010).
Link et al., "Phosphodiesterase 4 inhibition but not beta-adrenergic stimulation suppresses tumor necrosis factor-alpha release in peripheral blood mononuclear cells in septic shock," Crit Care. 12(6):R159 (2008) (9 pages).
Liu et al., "Effects of overexpression of ephrin-B2 on tumour growth in human colorectal cancer," Br J Cancer. 90(8):1620-6 (2004).
Long et al., "Prognostic and clinicopathologic associations of oncogenic BRAF in metastatic melanoma," J Clin Oncol. 29(10): 1239-1246 (2011).
Lorenz et al., "Cardiac hypertrophy: targeting Raf/MEK/ERK1/2-signaling," Int J Biochem Cell Biol. 41(12): 2351-2355 (2009).
Lowenberg et al.,"Specific inhibition of c-Raf activity by semapimod induces clinical remission in severe Crohn's disease," J Immunol. 175(4): 2293-2300 (2005).
Lozinskii et al., "Alkylthio derivatives of the aminoketene S,N-Acetals of heterocyclic beta-dicarbonyl compounds: one stage synthesis and properties," Chemistry of Heterocyclic Compounds. 38(9):1077-80 (2002).
Luo et al., "Coxsackievirus B3 replication is reduced by inhibition of the extracellular signal-regulated kinase (ERK) signaling pathway," J Virol. 76(7): 3365-3373 (2002).
Ma et al., "The ERK/MAPK pathway, as a target for the treatment of neuropathic pain," Expert Opin Ther Targets. 9(4):699-713 (2005).
Maddahi et al.,"Cerebral ischemia induces microvascular pro-inflammatory cytokine expression via the MEK/ERK pathway," J Neuroinflammation. 7:14 (2010) (13 pages).
Mammas et al., "Involvement of the ras genes in female genital tract cancer," Int J Oncol. 26(5):1241-1255 (2005).
Mansour et al., "Transformation of mammalian cells by constitutively active MAP kinase kinase," Science. 265(5174):966-70 (1994).
Marais et al., "Differential regulation of Raf-1, A-Raf, and B-Raf by oncogenic ras and tyrosine kinases," J Biol Chem. 272(7):4378-83 (1997).
Martich et al., "Detection of interleukin 8 and tumor necrosis factor in normal humans after intravenous endotoxin: the effect of antiinflammatory agents," J Exp Med. 173(4):1021-1024 (1991).
Martin et al., "Update on lymphocyte specific kinase inhibitors: a patent survey," Expert Opin Ther Pat. 20(11): 1573-1593 (2010).
Mashelkar et al., "Synthesis of some novel 4-substituted coumarins having potential biological activity (Part II)," Indian J Chem. 45B(4): 967-971 (2006).
Mataloni et al., "Synthesis of secondary amines by reduction of alpha-amidoalkylphenyl sulfones with sodium acetoxyborohydride," Synlett. 8:1129-32 (2003).
McCann et al.,"Apremilast, a novel PDE4 inhibitor, inhibits spontaneous production of tumour necrosis factor-alpha from human rheumatoid synovial cells and ameliorates experimental arthritis," Arthritis Res Ther. 12(3): R107 (2010) (11 pages).
McKay et al., "Complexity in KSR function revealed by Raf inhibitor and KSR structure studies," Small GTPases. 2(5):276-281 (2011) (7 pages).
McKillop et al., "Applications of ethyl carboethoxyformimidate to heterocyclic synthesis: preparation of condensed pyrazinones and 1,4-oxazinones," Synthesis. 3:301-304 (1997).
McMahon, "VEGF receptor signalling in tumor angiogenesis," Oncologist. 5(suppl I):3-10 (2000).
Mei et al., "Distribution, levels and phosphorylation of Raf-1 in Alzheimer's disease," J Neurochem. 99(5): 1377-1388 (2006).
Menard et al., "Novel potent BRAF inhibitors: toward 1 nM compounds through optimization of the central phenyl ring," J Med Chem. 52(13): 3881-3891 (2009).
Mercer et al., "Emerging role of MAP kinase pathways as therapeutic targets in COPD," Int J Chron Obstruct Pulmon Dis. 1(2):137-150 (2006).
Messinger et al., "Synthesis of alpha-amino- and alpha-amidosulfones. 5. Sulfones as chemical transport forms of substances with germicidae effect," Arch Pharm (Weinheim). 307(8):653-5 (1974). (In German with partial English language translation).
Metzner et al., "Fibroblast growth factor receptors as therapeutic targets in human melanoma: synergism with Braf inhibition," J Invest Dermatol. 131(10): 2087-2095 (2011).
Meyers et al., "FGFR2 exon IIIa and IIIc mutations in Crouzon, Jackson-Weiss, and Pfeiffer syndromes: evidence for missense changes, insertions, and a deletion due to alternative RNA splicing," Am J Hum Genet. 58(3):491-8 (1996).
Milella et al., "Therapeutic targeting of the MEK/MAPK signal transduction module in acute myeloid leukemia," J Clin Invest. 108(6): 851-859 (2001).
Mineo et al., "Prognostic impact of VEGF, CD31, CD34, and CD105 expression and tumour vessel invasion after radical surgery for IB-IIA non-small cell lung cancer," J Clin Pathol. 57(6):591-7 (2004).
Miura et al., "Simvastatin suppresses coronary artery endothelial tube formation by disrupting Ras/Raf/ERK signaling," Atherosclerosis. 175(2): 235-243 (2004).
Mohanta et al., "1-(methyldithiocarbony)imidazole: a useful thiocarbonyl transfer reagent for synthesis of substituted thioureas," Tetrahedron. 56(4):629-37 (2000).
Montagut et al., "Elevated CRAF as a potential mechanism of acquired resistance to BRAF inhibition in melanoma," Cancer Res. 68(12): 4853-4861 (2008) (16 pages).
Moore et al., "ROMP-generated oligomeric sulfonyl chlorides as versatile soluble scavenging agents," Org Lett. 5(2):105-7 (2003).
Mukherjee et al., "Raf-1 expression may influence progression to androgen insensitive prostate cancer," Prostate. 64(1):101-107 (2005).
Mukhopadhyay et al., "Role of TNFalpha in pulmonary pathophysiology," Respir Res. 7:125 (2006) (9 pages).
Mustonen et al., "Endothelial receptor tyrosine kinases involved in angiogenesis," J Cell Biol. 129(4):895-8 (1995).
Nakamoto et al., "Diverse roles for the Eph family of receptor tyrosine kinases in carcinogenesis," Miscrosc Res Tech. 59(1):58-67 (2002).
Nakamura et al., "Novel strategies for the treatment of inflammatory bowel disease: Selective inhibition of cytokines and adhesion molecules," World J Gastroenterol. 12(29): 4628-4635 (2006).
Nazarian et al., "Melanomas acquire resistance to B-RAF(V600E) inhibition by RTK or N-RAS upregulation," Nature. 468(7326): 973-977 (2010) (7 pages).
O'Reilly et al., "Angiostatin: A novel angiogenesis inhibitor that mediates the suppression of metastases by a Lewis lung carcinoma," Cell. 79(2):315-28 (1994).

(56) References Cited

OTHER PUBLICATIONS

Oeztuerk-Winder et al., "The many faces of p38 mitogen-activated protein kinase in progenitor/stem cell differentiation," Biochem J. 445(1): 1-10 (2012).
Orre et al., "VEGF, VEGFR-1, VEGFR-2, microvessel density and endothelial cell proliferation in tumours of the ovary," Int J Cancer. 84(2):101-8 (1999).
Ozawa et al., "Growth factors and their receptors in pancreatic cancer," Teratog Carcinog Mutagen. 21(1):27-44 (2001).
Pabst et al., "Analysis of K-ras mutations in pancreatic tissue after fine needle aspirates," Anticancer Res. 19(4A):2481-3 (1999).
Palanisamy et al., "Rearrangements of the RAF kinase pathway in prostate cancer, gastric cancer and melanoma," Nat. Med. 16(7): 793-798 (2010) (7 pages).
Parlow et al., "Synthesis and crystal structures of substituted benzenes and benzoquinones as tissue factor VIIa inhibitors," J Med Chem. 46(20):4297-312 (2003).
Partanen et al., "A novel endothelial cell surface receptor tyrosine kinase with extracellular epidermal growth factor homology domains," Mol Cell Biol. 12(4):1698-707 (1992).
Partanen et al., "Functions of Tie1 and Tie2 receptor tyrosine kinases in vascular development," Curr Top Microbiol Immunol. 237:159-72 (1999).
Patani et al., "Bioisosterism: a rational approach to drug design," Chem Rev. 96(8):3147-76 (1996).
Paulson et al., "Receptor tyrosine kinases and the regulation of hematopoiesis," Semin Immunol. 7(4):267-77 (1995).
Payne et al., "Human papillomavirus type 6b virus-like particles are able to activate the Ras-MAP kinase pathway and induce cell proliferation," J Virol. 75(9): 4150-4157 (2001).
Peacock et al., "A novel angiogenesis inhibitor suppresses rat adjuvant arthritis," Cell Immunol. 160(2):178-84 (1995).
Peacock et al., "Angiogenesis inhibition suppresses collagen arthritis," J Exp Med. 175(4):1135-8 (1992).
Pelletier et al., "In vivo selective inhibition of mitogen-activated protein kinase kinase 1/2 in rabbit experimental osteoarthritis is associated with a reduction in the development of structural changes," Arthritis Rheum. 48(6): 1582-1593 (2003).
Peters, "Vascular endothelial growth factor and the angiopoietins working together to build a better blood vessel," Circ Res. 83(3):342-3 (1998).
Petrovan et al., "DNA vaccination against VEGF receptor 2 reduces atherosclerosis in LDL receptor-deficient mice," Arterioscler Thromb Vasc Biol. 27(5): 1095-1100 (2007) (11 pages).
Pinedo et al., "Translational research: the role of VEGF in tumor angiogenesis," The Oncologist. 5:1-2 (2000).
Planz et al., "MEK-specific inhibitor U0126 blocks spread of Borna disease virus in cultured cells," J Virol. 75(10): 4871-4877 (2001).
Pleschka et al., "Influenza virus propagation is impaired by inhibition of the Raf/MEK/ERK signalling cascade," Nat Cell Biol. 3(3): 301-305 (2001) (7 pages).
Plomp et al., "Pfeiffer syndrome type 2: further delineation and review of the literature," Am J Med Genet. 75(3):245-51 (1998).
Poulikakos et al., "RAF inhibitor resistance is mediated by dimerization of aberrantly spliced BRAF(V600E)," Nature. 480(7377): 387-390 (2011) (5 pages).
Poulikakos et al., "RAF inhibitors transactivate RAF dimers and ERK signalling in cells with wild-type BRAF," Nature. 464(7287): 427-430 (2010) (5 pages).
Powers et al., "Fibroblast growth factors, their receptors and signalling," Endocr Relat Cancer. 7(3):165-97 (2000).
Prakash et al., "A convenient synthesis of alpha-anilinoacetophenones using hypervalent iodine," Indian Journal of Chemistry, Section B: Organic Chemistry Including Medicinal Chemistry. 31:349-50 (1992).
Prix et al., "Diagnostic biochip array for fast and sensitive detection of K-ras mutations in stool," Clin Chem. 48(3):428-35 (2002).
Rajagopalan et al., "Tumorgenesis: RAF/RAS oncogenes and mismatch-repairs status," Nature. 418(6901):934 (2002).

Ramadas et al., "LAC sulfur assisted synthesis of symmetrical thioureas," Synth Comm. 27(23):2255-60 (1997).
Reck et al., "Novel N-linked aminopiperidine inhibitors of bacterial topoisomerase type II: broad-spectrum antibacterial agents with reduced hERG activity," J Med Chem. 54(22): 7834-7847 (2011).
Remli et al., "Reaction of o-arylenediamines with ethyl 3-fluoro 2-ketoesters synthesis of quinoxaline derivatives," J Fluorine Chem. 44:15-23 (1989).
Riva et al., "Differential c-myc, c-jun, c-raf and p53 expression in squamous cell carcinoma of the head and neck: implication in drug and radioresistance," Eur J Cancer B Oral Oncol. 31 B(6): 384-391 (1995).
Rotsos et al., "Cystoid macular edema," Clin Ophthalmol. 2(4): 919-930 (2008).
Rubinstein et al., "Incidence of the V600K mutation among melanoma patients with BRAF mutations, and potential therapeutic response to the specific BRAF inhibitor PLX4032," J Transl Med. 8: 67 (2010) (3 pages).
Rudy et al., "Zweikernige Alloxan-Abkömmlinge von 2.3-Diaminopyridinen," Chemische Berichte. 71:1323-1332 (1938) (Abstract Included) (11 pages).
Salama et al., "BRAF in Melanoma: Current strategies and future directions," Clin Cancer Res. 19(16): 4326-4334 (2013).
Sarkis et al., "Synthesis and spectroscopic properties of some new N,N'-disubstituted thioureas of potential biological interest," J Heterocyclic Chemistry. 22:137-40 (1985).
Schindler et al., "Analysis of BRAF V600E mutation in 1,320 nervous system tumors reveals high mutation frequencies in pleomorphic xanthoastrocytoma, ganglioglioma and extra-cerebellar pilocytic astrocytoma," Acta Neuropathol. 121(3): 397-405 (2011).
Schreck et al., "Raf kinases: Oncogenesis and drug discovery," Int J Cancer. 119(10): 2261-2271 (2006).
Search Report for British Application No. GB 0423554.5, dated Feb. 23, 2005 (1 page).
Search Report for British Application No. GB 0608268.9, dated Aug. 9, 2006 (1 page).
Search Report for British Application No. GB 0807609.3, dated Aug. 21, 2008 (2 pages).
Search Report for United Kingdom Application No. GB 1320729.5, dated May 20, 2014 (2 pages).
Search Report for United Kingdom Application No. GB 1320732.9, dated May 19, 2014 (2 pages).
Seki et al., "Reaction products of dialkyl acetylenedicarboxylates with 2,3-diaminopyridine," J Heterocyclic Chem. 32(3): 1071-1073 (1995).
Shakhov et al., "Kappa B-type enhancers are involved in lipopolysaccharide-mediated transcriptional activation of the tumor necrosis factor alpha gene in primary macrophages," J Exp Med. 171(1): 35-47 (1990).
Shapira et al., "Protection against endotoxic shock and lipopolysaccharide-induced local inflammation by tetracycline: correlation with inhibition of cytokine secretion," Infect Immun. 64(3):825-828 (1996).
Shaw et al., "The preparation of 2,6-diaminopyrazine, 2,6-diazidopyrazine and some of their derivatives," J Heterocycl Chem. 17(1): 11-6 (1980).
Sherman et al., "Synthesis of unsymmetrical and regio-defined 2,3,6-quinoxaline and 2,3,7-pyridopyrazine derivatives," Tetrahedron Lett. 48(51):8943-8946 (2007).
Shi et al., "Melanoma whole-exome sequencing identifies (V600E)B-RAF amplification-mediated acquired B-RAF inhibitor resistance," Nat Commun. 3: 724 (2012) (8 pages).
Shibuya, "Vascular endothelial growth factor and its receptor system: physiological functions in angiogenesis and pathological roles in various diseases," J Biochem. 153(1):13-19 (2013).
Shiina et al., "A new method for the synthesis of carboxamides and peptides using 1,1'-carbonyldioxydi[2(1H)-pyridone] (CDOP) in the absence of basic promoters," Tetrahedron Letters. 44:1951-55 (2003).
Shin et al., "Expression of EphrinB2 identifies a stable genetic difference between arterial and venous vascular smooth muscle as well as endothelial cells, and marks subsets of microvessels at sites of adult neovascularization," Dev Biol. 230(2):139-50 (2001).

(56) References Cited

OTHER PUBLICATIONS

Sievert et al.,"Paradoxical activation and RAF inhibitor resistance of BRAF protein kinase fusions characterizing pediatric astrocytomas," Proc Natl Acad Sci USA. 110(15): 5957-5962 (2013) (9 pages).
Singer et al., "Mutations in BRAF and KRAS characterize the development of low-grade ovarian serous carcinoma," J Natl Cancer Inst. 95(6):484-6 (2003).
Smalley et al.,"CRAF inhibition induces apoptosis in melanoma cells with non-V600E BRAF mutations," Oncogene. 28(1): 85-94 (2009).
Smith et al.,"Vascular endothelial growth factor receptors VEGFR-2 and VEGFR-3 are localized primarily to the vasculature in human primary solid cancers," Clin Cancer Res. 16(14): 3548-3561 (2010).
Solit et al., "BRAF mutation predicts sensitivity to MEK inhibition," Nature. 439(7074):358-62 (2006).
Song et al., "Activation of ERK/CREB pathway in spinal cord contributes to chronic constrictive injury-induced neuropathic pain in rats," Acta Pharmacol Sin. 26(7): 789-98 (2005).
Sosman et al., "Survival in BRAF V600-mutant advanced melanoma treated with vemurafenib," N Engl J Med. 366(8):707-714 (2012).
Srinivas et al., "A highly convenient, efficient, and selective process for preparation of esters and amides from carboxylic acids using Fe(3+)-K-10-montmorillonite clay," J Org Chem. 68(3):1165-7 (2003).
Srivastava et al., "Synthesis and antithyroid activity of some benzimidazolyl and benzenesulphonyl thiocarbamides" Current Science. 50(7):305-7 (1981).
Straussman et al., "Tumour micro-environment elicits innate resistance to RAF inhibitors through HGF secretion," Nature. 487(7408): 500-504 (2012) (7 pages).
Suijkerbuijk et al., "Development of novel, highly potent inhibitors of V-RAF murine sarcoma viral oncogene homologue B1 (BRAF): increasing cellular potency through optimization of a distal heteroaromatic group," J Med Chem. 53(7):2741-56 (2010).
Sullivan et al., "BRAF in melanoma: pathogenesis, diagnosis, inhibition, and resistance," J Skin Cancer. 2011:423239 (2011) (8 pages).
Suri et al., "Requisite role of angiopoietin-1, a ligand for TIE2 receptor, during embryonic angiogenesis," Cell. 87(7):1171-80 (1996).
Tam et al., "Blockade of VEGFR2 and not VEGFR1 can limit diet-induced fat tissue expansion: role of local versus bone marrow-derived endothelial cells," PLoS One. 4(3):e4974 (2009) (6 pages).
Tang et al., "Coexpression of transcripts encoding EPHB receptor protein tyrosine kinases and their ephrin-B ligands in human small cell lung carcinoma," Clin Cancer Res. 5(2):455-60 (1999).
Tang et al., "High-level expression of EPHB6, EFNB2, and EFNB3 is associated with low tumor stage and high TrkA expression in human neuroblastomas," Clin Cancer Res. 5(6):1491-6 (1999).
Tanga et al., "Syntheses of two potential food mutagens," J Heterocycl Chem. 40(4):569-73 (2003).
Taraboletti et al., "Inhibition of angiogenesis and murine hemangioma growth by batimastat, a synthetic inhibitor of matrix metalloproteinases," J Natl Cancer Inst. 87(4):293-8 (1995).
Temple et al., "New anticancer agents: alterations of the carbamate group of ethyl (5-amino-1,2-dihydro-3-phenylpyrido[3,4-b]pyrazin-7-yl)carbamates," J Med Chem. 32(10):2363-7 (1989).
Terao et al., "Synthesis of .alpha.-thio, .alpha.-sulfinyl, and .alpha.-sulfonyl-substituted nitrosamines," Chem Pharm Bull. 25(11):2964-8 (1977).
Thalhamer et al., "MAPKs and their relevance to arthritis and inflammation," Rheumatology (Oxford). 47(4):409-414 (2008).
Thornber, "Isosterism and molecular modification in drug design," Chem Soc Rev. 8(4):563-80 (1979).
Uchida et al., "Studies on 2(1H)-quinolinone derivatives as gastric antiulcer active agents. 2-(4-chlorobenzoylamino)-3-[2(1H)-quinolinon-4-yl]propionic acid and related compounds," Chem Pharm Bull (Tokyo). 33(9):3775-86 (1985).

Vergani et al., "Identification of MET and SRC activation in melanoma cell lines showing primary resistance to PLX4032," Neoplasia. 13(12):1132-1142 (2011) (14 pages).
Villanueva et al., "Acquired resistance to BRAF inhibitors mediated by a RAF kinase switch in melanoma can be overcome by cotargeting MEK and IGF-1R/PI3K," Cancer Cell. 18(6):683-695 (2010) (34 pages).
Wan et al., "Mechanism of activation of the RAF-ERK signaling pathway by oncogenic mutations of B-RAF," Cell. 116(6):855-67 (2004).
Wang et al., "Antisense targeting of basic fibroblast growth factor and fibroblast growth factor receptor-1 in human melanomas blocks intratumoral angiogenesis and tumor growth," Nature. 3(8): 887-893 (1997).
Wang et al., "Inhibition of MEK/ERK 1/2 pathway reduces pro-inflammatory cytokine interleukin-1 expression in focal cerebral ischemia," Brain Res. 996(1):55-66 (2004).
Wang et al., "Molecular distinction and angiogenic interaction between embryonic arteries and veins revealed by ephrin-B2 and its receptor Eph-B4", Cell. 93(5):741-53 (1998).
Wang et al., "Significant neuroprotection against ischemic brain injury by inhibition of the MEK1 protein kinase in mice: exploration of potential mechanism associated with apoptosis," J Pharmacol Exp Ther. 304(1): 172-178 (2003).
Ward et al., "Targeting oncogenic Ras signaling in hematologic malignancies," Blood. 120(17):3397-3406 (2012).
Wellbrock et al., "The RAF proteins take centre stage," Nat Rev Mol Cell Biol. 5(11):875-85 (2004).
Wellbrock et al., "V599EB-RAF is an oncogene in melanocytes," Cancer Res. 64(7): 2338-2342 (2004) (6 pages).
Whittaker et al., "A novel, selective and efficacious nanomolar pyridopyrazinone inhibitor of V600EBRAF," Cancer Res. 70(20): 8036-8044 (2010) (13 pages).
Wilks, "Structure and function of the protein tyrosine kinases," Prog Growth Factor Res. 2(2):97-111 (1990).
Wilson et al., "Widespread potential for growth-factor-driven resistance to anticancer kinase inhibitors," Nature. 487(7408): 505-509 (2012) (6 pages).
Xing, "Molecular pathogenesis and mechanisms of thyroid cancer," Nat Rev Cancer. 13(3):184-199 (2013).
Yancopoulos et al., "Vasculogenesis, angiogenesis and growth factors: ephrins enter the fray at the border," Cell. 93(5):661-4 (1998).
Yang et al., "Regulation of human immunodeficiency virus type 1 infectivity by the ERK mitogen-activated protein kinase signaling pathway," J Virol. 73(4):3460-3466 (1999).
Yao et al., "Lipopolysaccharide induction of the tumor necrosis factor-alpha promoter in human monocytic cells. Regulation by Egr-1, c-Jun and NF-kappaB transcription factors," J Biol Chem. 272(28): 17795-17801 (1997).
Yeatman, "A renaissance for SRC," Nat Rev Cancer. 4(6):470-480 (2004).
Young et al., "Ras signaling and therapies," Adv Cancer Res. 102:1-17 (2009).
Yu et al., "Loss of fibroblast growth factor receptor 2 ligand-binding specificity in Apert syndrome," Proc Natl Acad Sci U.S.A. 97(26):14536-41 (2000).
Zejc et al., "Synthesis and anticonvulsant properties of some arylsuccinate methylpyridylimides", Pol J Pharmacol Pharm. 42(1):69-77 (1990).
Zhang et al., "Activation of the Ras/Raf/MEK pathway facilitates hepatitis C virus replication via attenuation of the interferon-JAK-STAT pathway," J Virol. 86(3): 1544-1554 (2012).
Zhang et al., "Targeting Src family kinases in anti-cancer therapies: turning promise into triumph," Trends Pharmacol Sci. 33(3): 122-128 (2012).
Zhou et al.,"Synthesis and SAR of 5-, 6-, 7- and 8-aza analogues of 3-aryl-4-hydroxyquinolin-2(1H)-one as NMDA/glycine site antagonists," Bioorg Med Chem. 9(8):2061-71 (2001).
Ziegler et al.,"Some 9-Aza-alloxazines," J Am Chem Soc. 71:1891-1893 (1949).
Zouki et al.,"Peroxynitrite induces integrin-dependent adhesion of human neutrophils to endothelial cells via activation of the Raf-1/MEK/Erk pathway," FASEB J. 15(1):25-27 (2001).

\* cited by examiner

AA-01

AA-02

AA-03

AA-04

BB-01

BB-02

(Comparison Compounds)

(mutant RAS cell line: SW620)

(mutant RAS cell line: SW620)

(mutant BRAF cell line: A375)

(mutant BRAF cell line: A375)

(mutant RAS cell line: SW620)

(mutant RAS cell line: SW620)

(mutant RAS cell line: SW620)

(mutant RAS cell line: SW620)

(mutant BRAF cell line: A375)

1-(5-TERT-BUTYL-2-PHENYL-2H-PYRAZOL-3-YL)-3-[2-FLUORO-4-(1-METHYL-2-OXO-2,3-DIHYDRO-1H-IMIDAZO[4,5-B]PYRIDIN-7-YLOXY)-PHENYL]-UREA AND RELATED COMPOUNDS AND THEIR USE IN THERAPY

RELATED APPLICATION

This application is related to U.S. patent application No. 61/300,085 filed 1 Feb. 2010, the contents of which are incorporated herein by reference in their entirety.

TECHNICAL FIELD

The present invention pertains generally to the field of therapeutic compounds, and more specifically to certain compounds (for convenience, collectively referred to herein as "IP compounds"), which, inter alia, are useful in the treatment of cancer, e.g., cancer characterised by (e.g., driven by) mutant RAS ("mutant RAS cancer"). The present invention also pertains to pharmaceutical compositions comprising such compounds, and the use of such compounds and compositions in the treatment of cancer, e.g., mutant RAS cancer.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Cancer and RAS

RAS proteins are small-guanine nucleotide binding proteins that are downstream of growth factor, cytokine and hormone receptors. These cell surface receptors activate proteins called guanine-nucleotide exchange factors (GNEFs), which replace GDP for GTP on RAS proteins, stimulating RAS activation. Other proteins called GTPase-activating proteins (GAPs) stimulate the intrinsic GTPase activity of RAS, thereby promoting GTP hydrolysis and returning RAS to its inactive GDP-bound state. Activated RAS binds to several effector proteins, including phosphoinositide 3-kinase (PI3K), the RAF family of protein kinases, and the Rat guanine-nucleotide exchange factor. These effectors in turn regulate the activity of the signalling pathways that control cell proliferation, senescence, survival and differentiation. There are three RAS genes in mammals called HRAS, KRAS and NRAS and they serve overlapping but non-conserved functions.

RAS proteins are also important in cancer. 20-30% of human tumours harbour somatic gain-of-function mutations in one of the RAS genes. Most commonly these involve the codons for glycine 12 (G12), glycine 13 (G13) and glutamine 61 (Q61) and these mutations impair, through different mechanisms, the GAP-stimulated intrinsic GTPase activity of RAS, trapping it in the active GTP-bound state and allowing it to promote tumorigenesis. See, e.g., Downward, 2003; Young et al., 2009; and Bos, 1989.

TABLE 1

Frequency of RAS Mutatations in Different Types of Cancers

| Tumour Type | Frequency |
| --- | --- |
| Pancreas | 90% |
| Thyroid (Undifferentiated papillary) | 60% |
| Thyroid (Follicular) | 55% |
| Colorectal | 45% |
| Seminoma | 45% |
| Myelodysplastic syndrome (MDS) | 40% |
| Lung adenocarcinoma (non-small-cell) | 35% |
| Liver | 30% |
| Acute myelogenous leukemia (AML) | 30% |
| Melanoma | 15% |
| Bladder | 10% |
| Kidney | 10% |

RAS and BRAF

Active RAS proteins activate several downstream effectors, including the proteins of the RAF family. There are three RAF proteins, ARAF, BRAF and CRAF. Activated RAF phosphorylates and activates a second protein kinase called MEK, which then phosphorylates and activates a third protein kinase called ERK. ERK phosphorylates a multitude of cytosolic and nuclear substrates, thereby regulating cell processes such as proliferation, survival, differentiation and senescence.

BRAF is important in cancer, because it is mutated in about 2% of human cancers, particularly in melanoma (43% of cases), thyroid (45%), ovarian (10%), and colorectal (13%) cancers. In contrast, ARAF and CRAF mutations are very rare in human cancer. Notably, however, in cancer cells, oncogenic RAS does not signal through BRAF, but instead signals exclusively through CRAF to activate MEK.

Over 100 different mutations have been described in BRAF in cancer, but a single mutation (a glutamic acid substitution for the valine at position 600) accounts for about 90% of the mutations that occur. This mutant activates BRAF 500-fold, and allows it to stimulate constitutive ERK and NFkB signalling, stimulating survival and proliferation. Consequently, $^{V600E}$BRAF can transform cells such as fibroblasts and melanocytes. Inhibition of $^{V600E}$BRAF in cancer cells inhibits cell proliferation and induces apoptosis in vitro, and in vivo it suppresses tumor cell growth, validating $^{V600E}$BRAF as a therapeutic target.

In the vast majority of cancers, BRAF and RAS mutations are mutually exclusive. This provides genetic evidence to suggest that these proteins are on the same pathway and that they drive the same processes in cancer cells. However, there are clear differences between oncogenic BRAF and oncogenic RAS functions in cancer cells. First, RAS activates several pathways, whereas BRAF is only known to activate the MEK/ERK pathway. As a consequence, BRAF mutant cells are more dependent on MEK/ERK signalling and so are considerably more sensitive to BRAF or MEK inhibitors than cell in which RAS is mutated. See, e.g., Garnett et al., 2004; Wellbrock et al., 2004; Gray-Schopfer et al., 2007; Solit et al., 2006.

Related Compounds

Niculescu-Duvaz et al., 2006 (WO 2006/043090 A1), describes the following classes of compounds at pages 41 and 43 therein. The compounds are described as BRAF inhibitors useful for the treatment of cancer, especially mutant BRAF cancer.

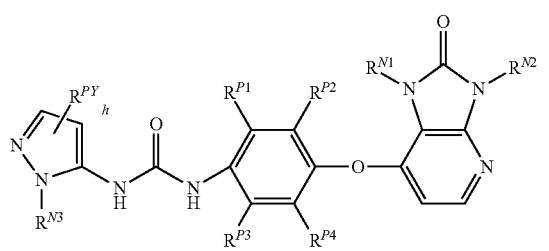

Additionally, Niculescu-Duvaz et al., 2006 provides the following examples:

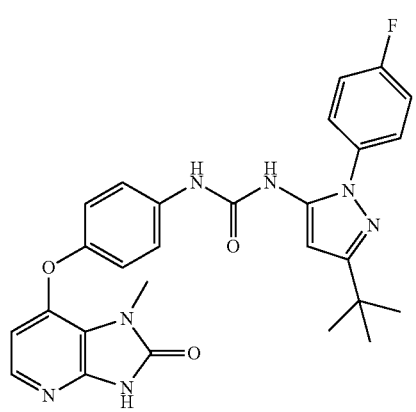

CJS 3247

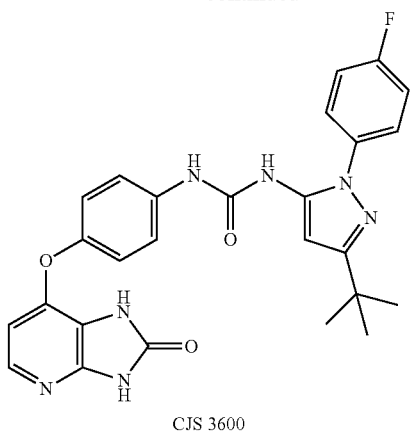

CJS 3600

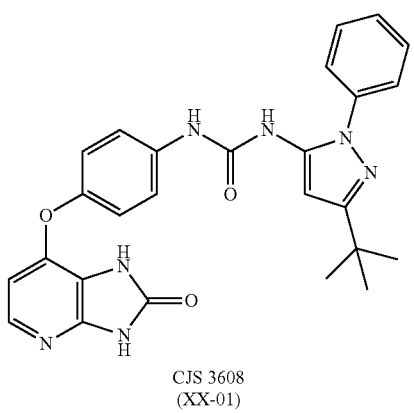

CJS 3608
(XX-01)

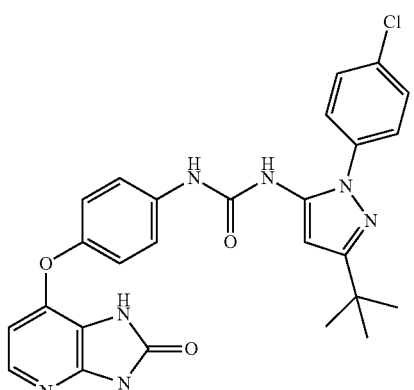

CJS 3609

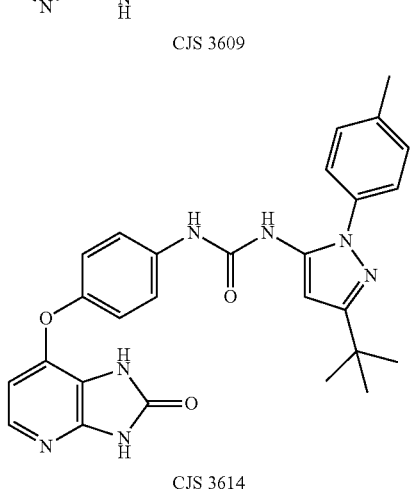

CJS 3614

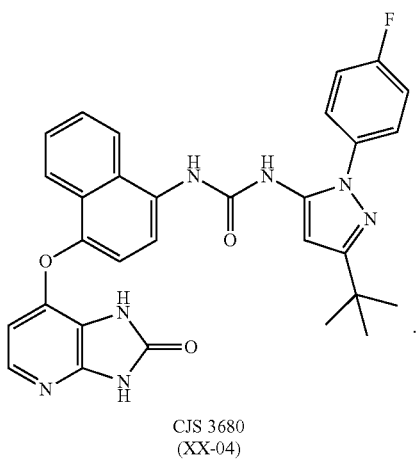

CJS 3680
(XX-04)

Niculescu-Duvaz et al., 2007 (WO 2007/125330 A1), describes the following classes of compounds at pages 57 and 58 therein. The compounds are described as BRAF inhibitors useful for the treatment of cancer, especially mutant BRAF cancer.

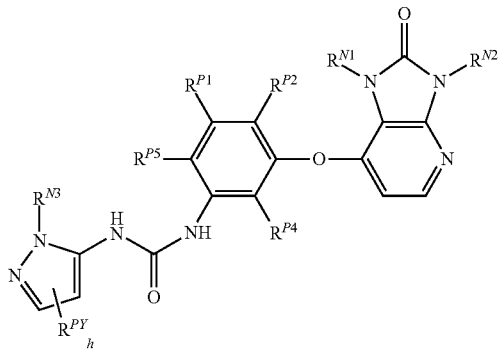

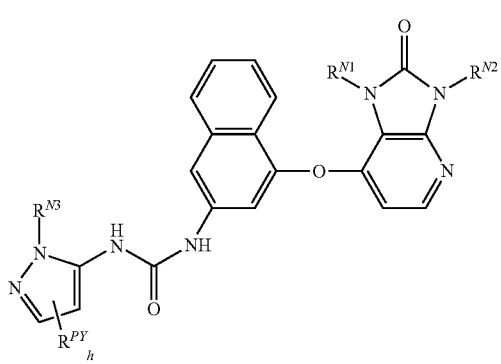

Additionally, Niculescu-Duvaz et al., 2007 provides the following examples:

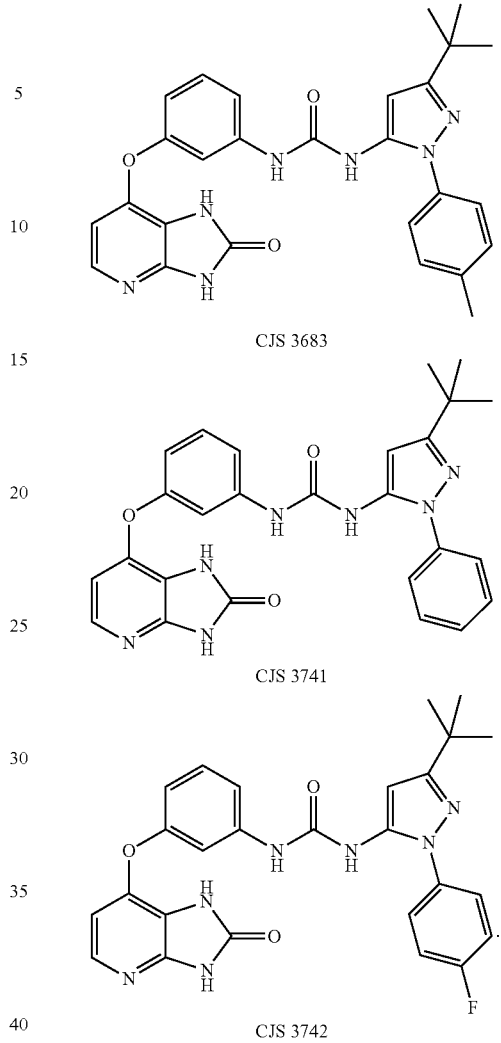

CJS 3683

CJS 3741

CJS 3742

The present invention provides alternative compounds, which are characterized by a particular combination of structural motifs, and which provide surprising and unexpected activity (e.g., activity against mutant RAS cancers), for example, as compared to one or more of the structurally-related known compounds.

Although structurally-related compounds are known as BRAF inhibitors, it would not have been predicted that the claimed compounds are active against mutant RAS cancers.

SW620, HCT116, and WM1361; and (c) a panel of wild type BRAF and RAS (wtBRAFT/RAS) cell lines: SKMEL23, KM12, and BT474.

Figure 1:
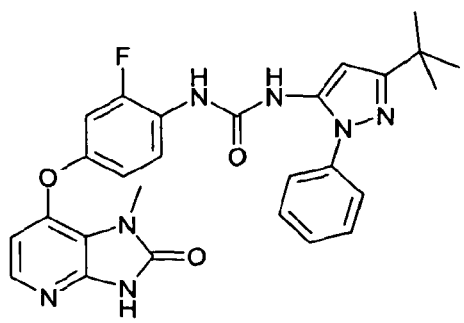
FIG. 1 shows the chemical structure of several compounds of the present invention: AA-01, AA-02, AA-03, and AA-04.
Figure 1:
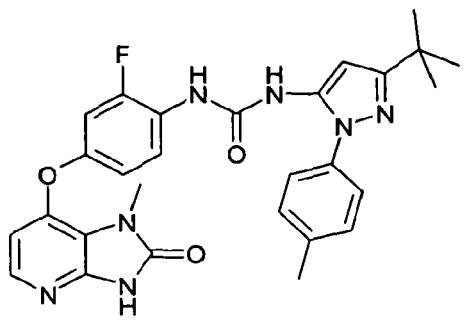
Figure 1:
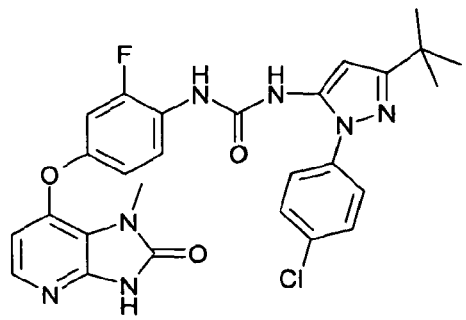
Figure 1:
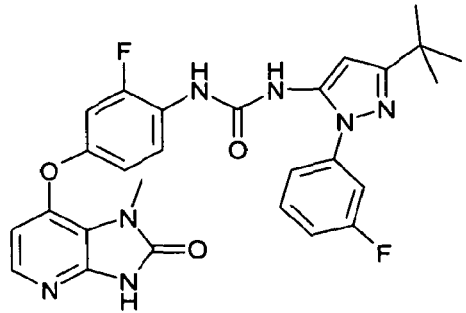
Figure 2:
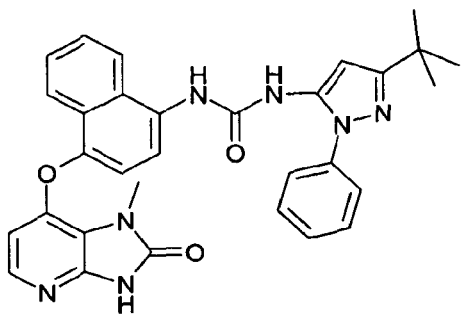
FIG. 2 shows the chemical structure of several compounds of the present invention: BB-01 and BB-02.
Figure 2:
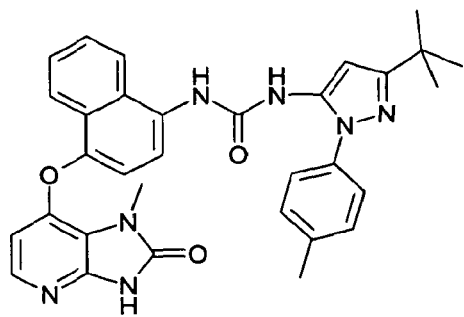
Figure 3:
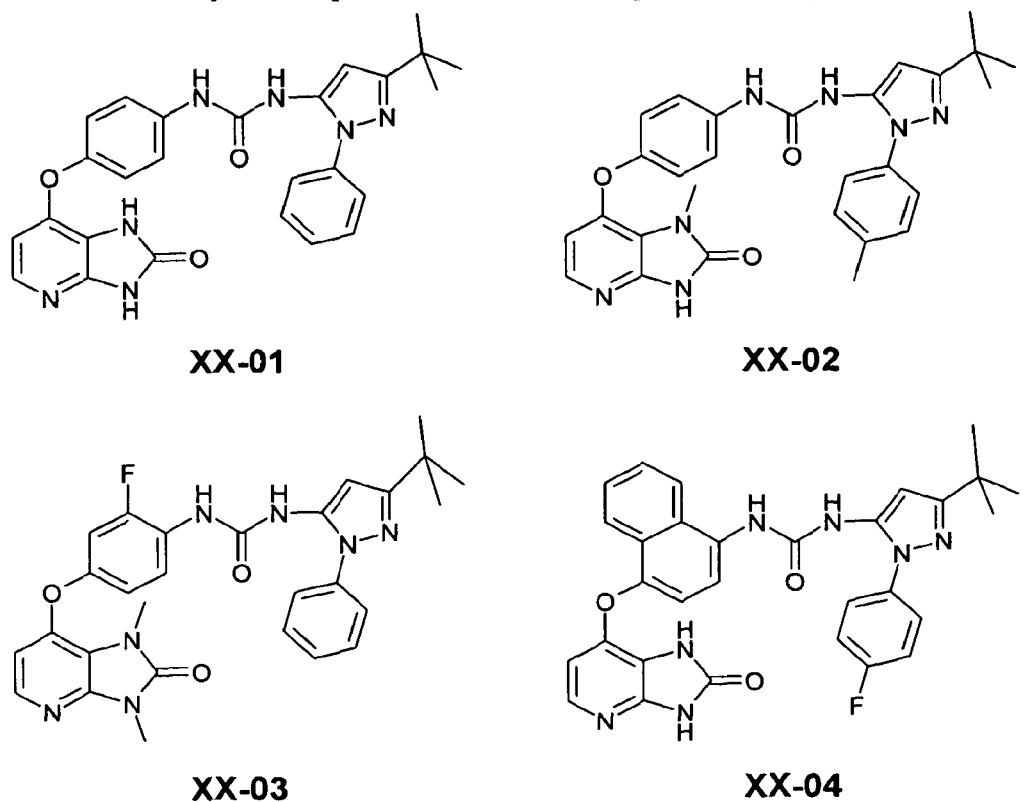
FIG. 3 shows the chemical structure of several comparison compounds: XX-01, XX-02, XX-03, and XX-04.
Figure 4:
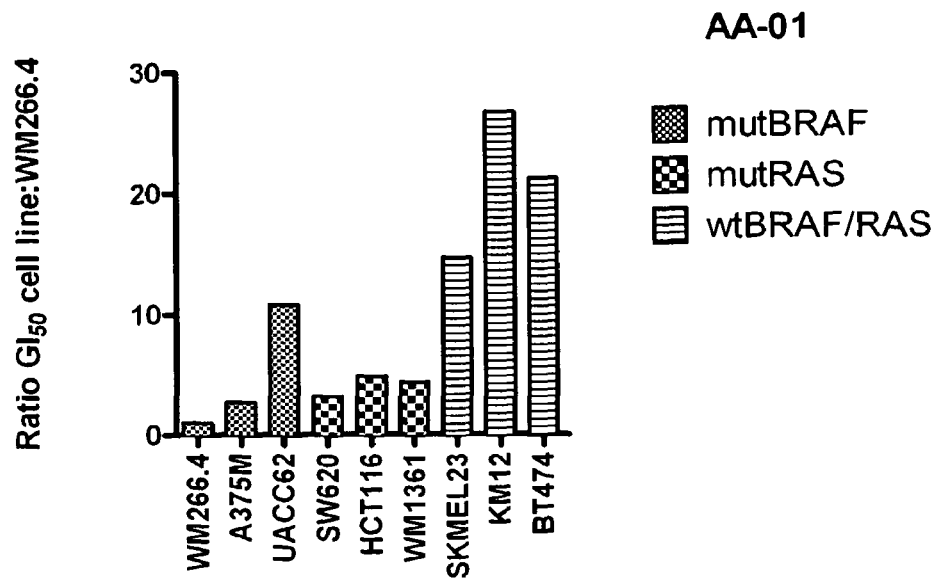
FIG. 4 is a bar graph showing the ratio of the $GI_{50}$ for each of a range of cell lines to the $GI_{50}$ for the WM266.4 cell line for compound AA-01. The range of cell lines are (a) a panel of mutant BRAF (mutBRAF) cell lines: WM266.4, A375M, UACC62; (b) a panel of mutant RAS (mutRAS) cell lines.
Figure 5:
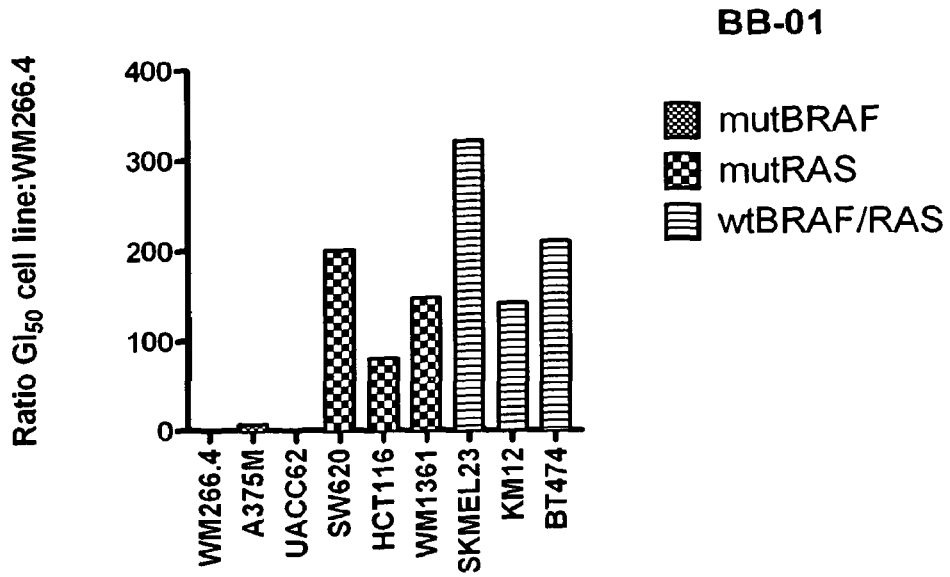

FIG. 5 is a bar graph showing the ratio of the $GI_{50}$ for each of a range of cell lines to the $GI_{50}$ for the WM266.4 cell line for compound BB-01. The ranges of cell lines are as for FIG. 4.

Figure 6:
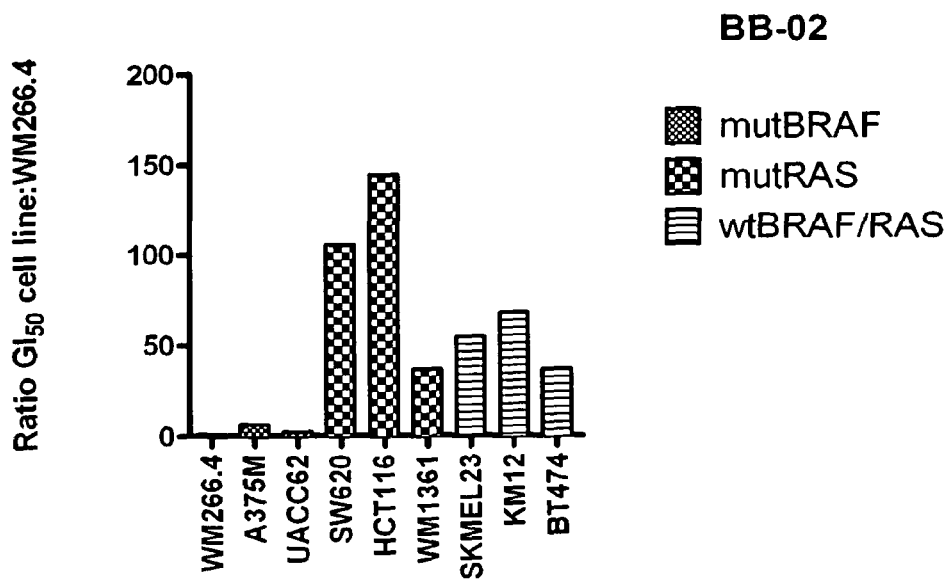

FIG. 6 is a bar graph showing the ratio of the $GI_{50}$ for each of a range of cell lines to the $GI_{50}$ for the WM266.4 cell line for compound BB-02. The ranges of cell lines are as for FIG. 4.

Figure 7:
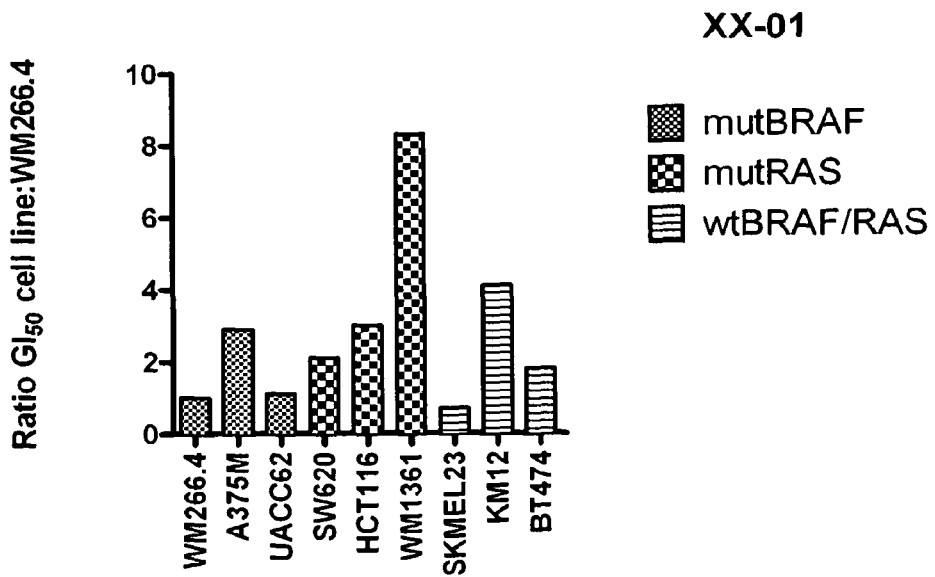

FIG. 7 is a bar graph showing the ratio of the $GI_{50}$ for each of a range of cell lines to the $GI_{50}$ for the WM266.4 cell line for comparison compound XX-01. The ranges of cell lines are as for FIG. 4.

Figure 8:
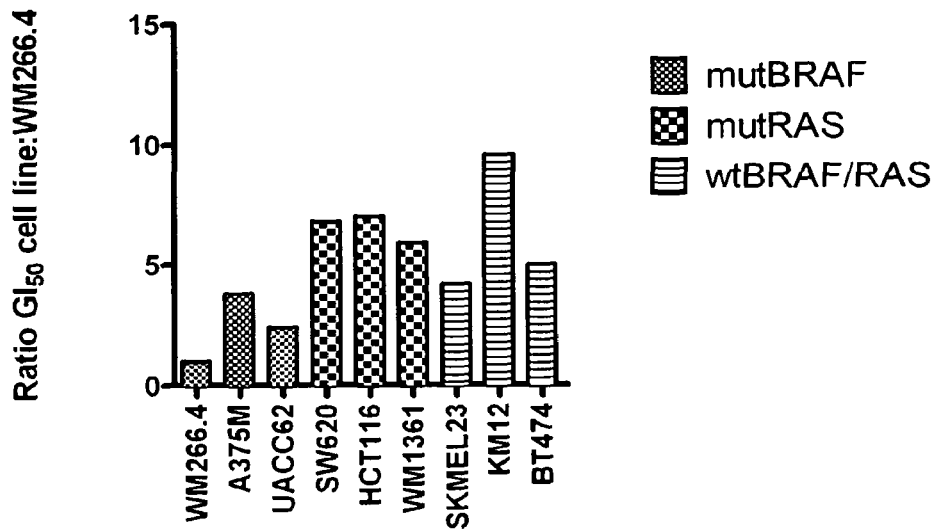

FIG. 8 is a bar graph showing the ratio of the $GI_{50}$ for each of a range of cell lines to the $GI_{50}$ for the WM266.4 cell line for comparison compound XX-02. The ranges of cell lines are as for FIG. 4.

Figure 9:
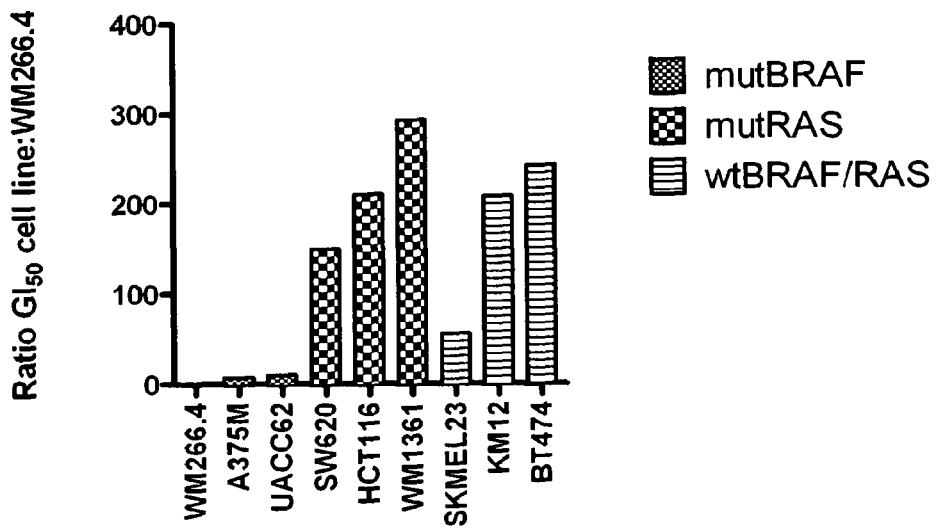

FIG. 9 is a bar graph showing the ratio of the $GI_{50}$ for each of a range of cell lines to the $GI_{50}$ for the WM266.4 cell line for comparison compound XX-03. The ranges of cell lines are as for FIG. 4.

Figure 10:
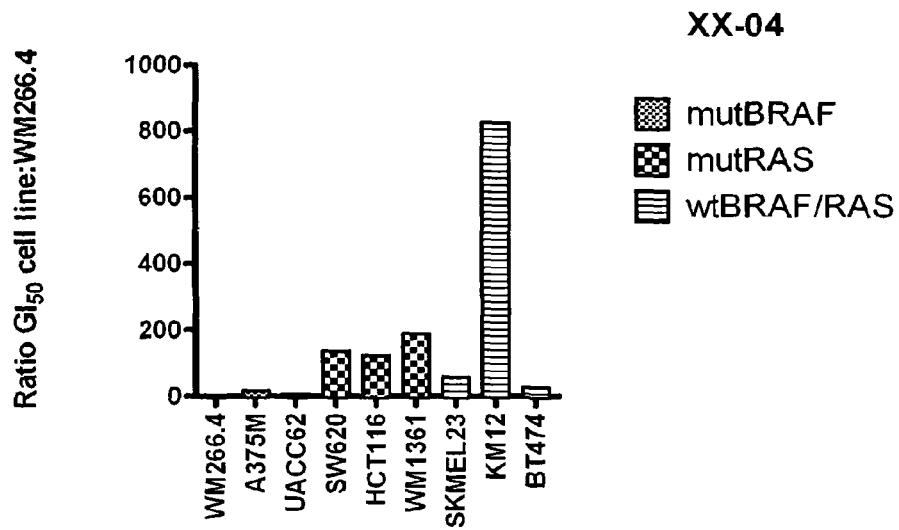

FIG. 10 is a bar graph showing the ratio of the $GI_{50}$ for each of a range of cell lines to the $GI_{50}$ for the WM266.4 cell line for comparison compound XX-04. The ranges of cell lines are as for FIG. 4.

Figure 11:
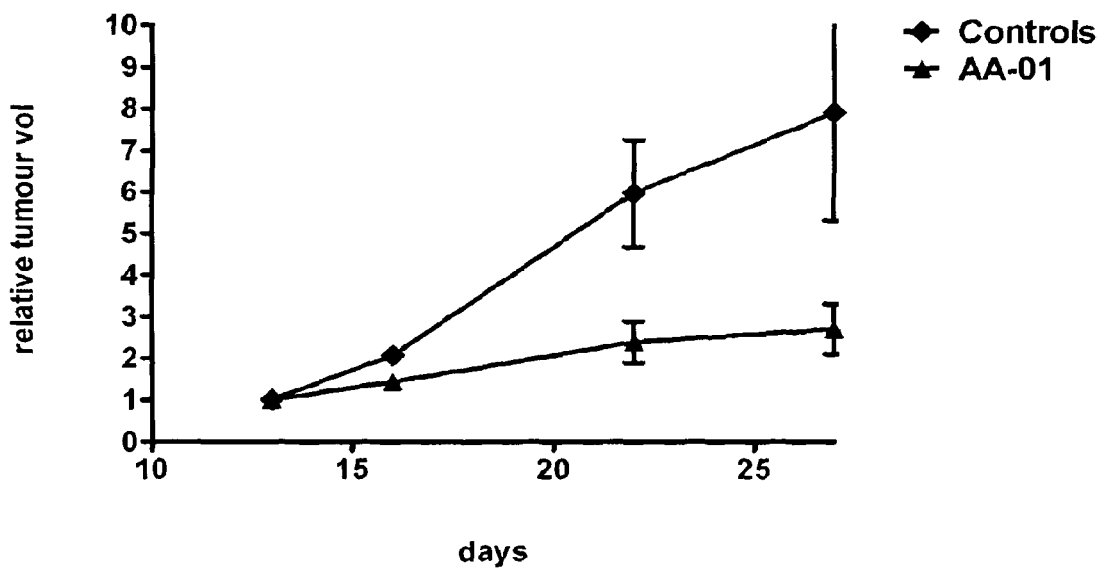

FIG. 11 is a graph of relative tumour volume as a function of time (days) for mouse xenografts of the mutant RAS cell line SW620, for treatment with compound AA-01 and for controls.

Figure 12:
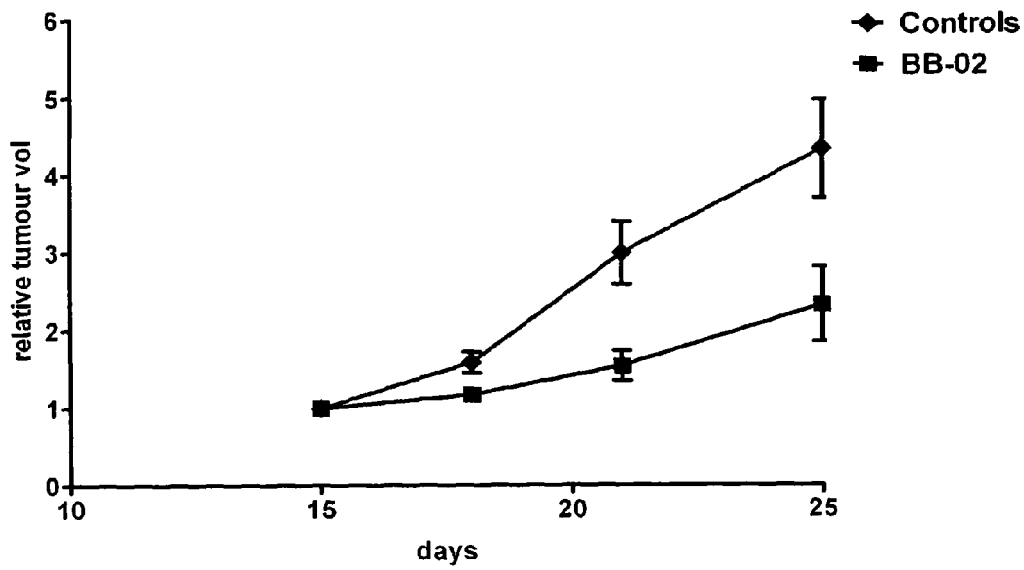

FIG. 12 is a graph of relative tumour volume as a function of time (days) for mouse xenografts of the mutant RAS cell line SW620, for treatment with compound BB-02 and for controls.

Figure 13:
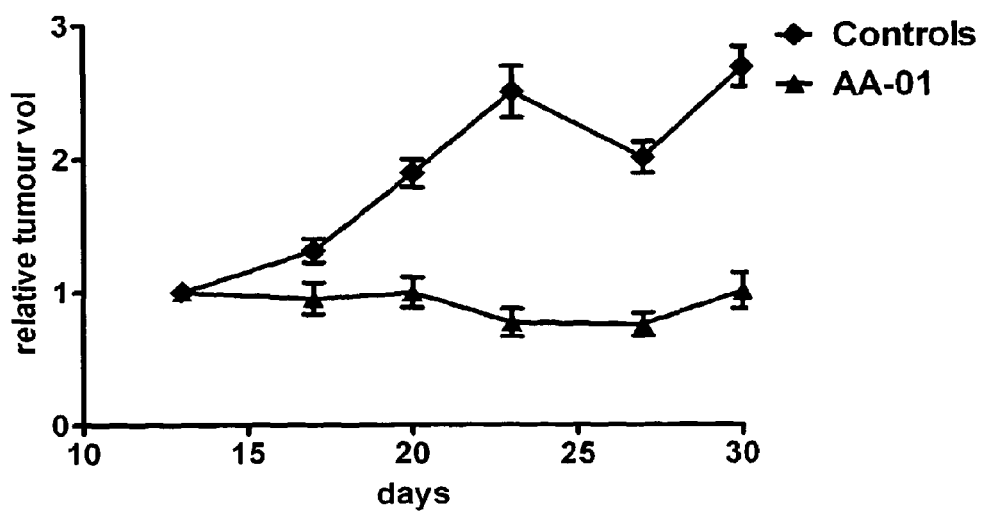

FIG. 13 is a graph of relative tumour volume as a function of time (days) for mouse xenografts of the mutant BRAF cell line A375, for treatment with compound AA-01 and for controls.

Figure 14:
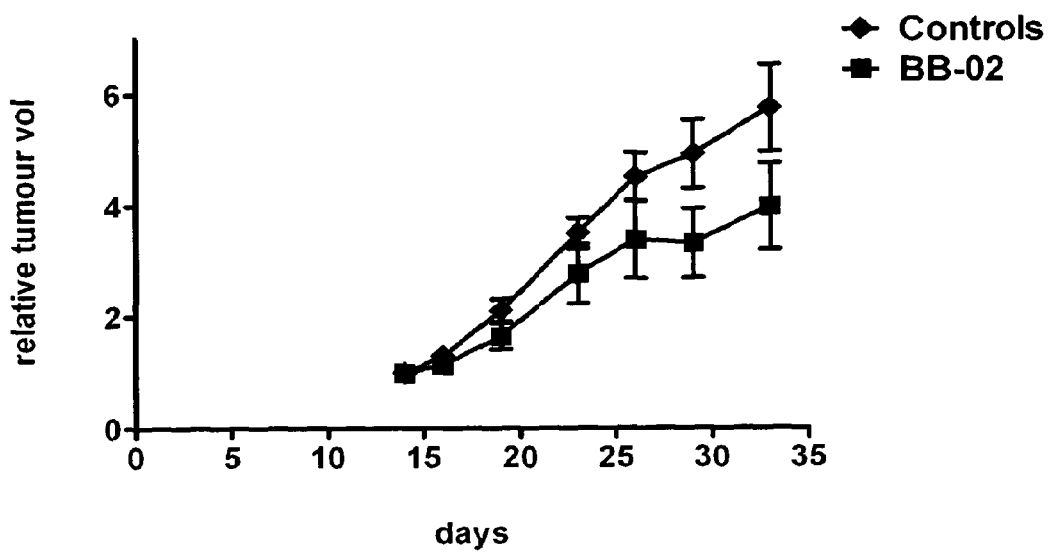

FIG. 14 is a graph of relative tumour volume as a function of time (days) for mouse xenografts of the mutant BRAF cell line A375, for treatment with compound BB-02 and for controls.

Figure 15:
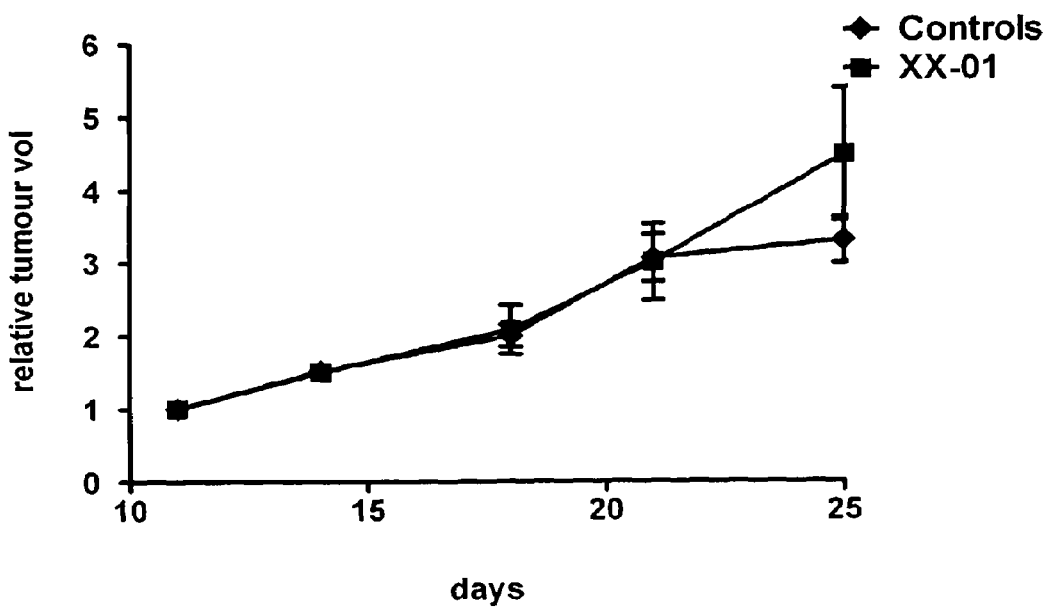

FIG. 15 is a graph of relative tumour volume as a function of time (days) for mouse xenografts of the mutant RAS cell line SW620, for treatment with comparison compound XX-01 and for controls.

Figure 16:
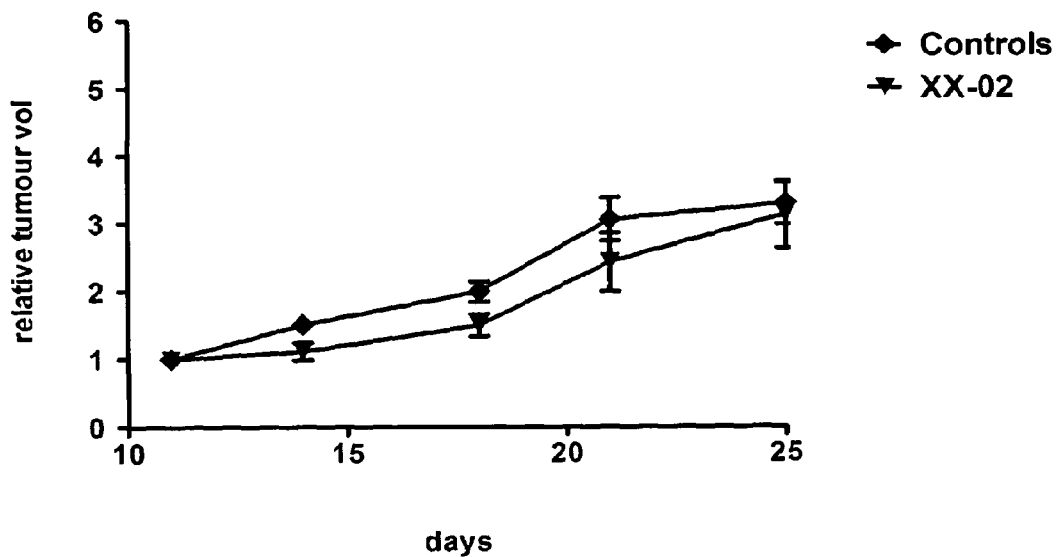

FIG. 16 is a graph of relative tumour volume as a function of time (days) for mouse xenografts of the mutant RAS cell line SW620, for treatment with comparison compound XX-02 and for controls.

Figure 17:
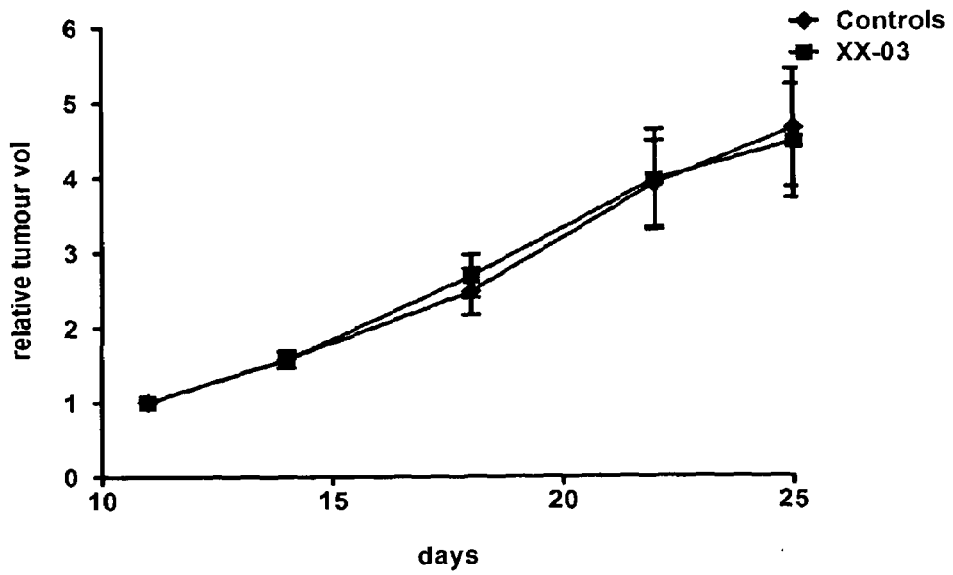

FIG. 17 is a graph of relative tumour volume as a function of time (days) for mouse xenografts of the mutant RAS cell line SW620, for treatment with comparison compound XX-03 and for controls.

Figure 18:
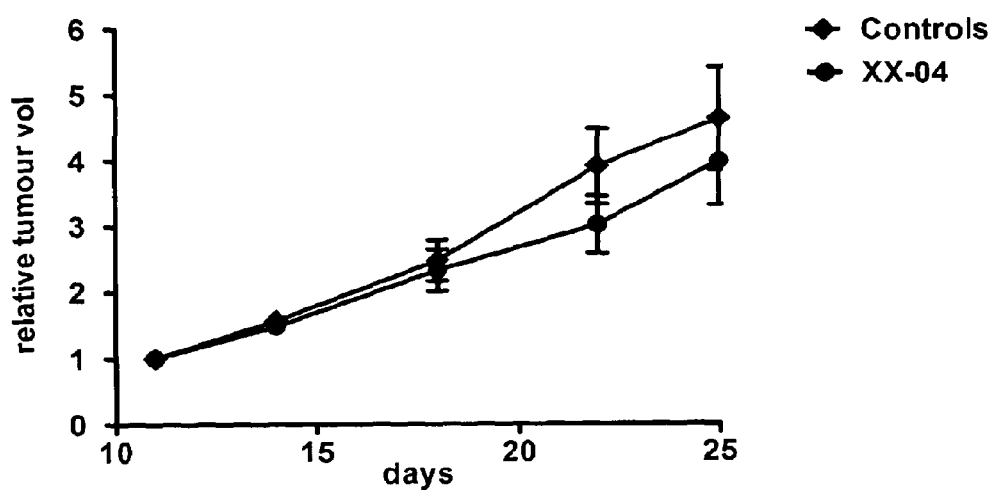

FIG. 18 is a graph of relative tumour volume as a function of time (days) for mouse xenografts of the mutant RAS cell line SW620, for treatment with comparison compound XX-04 and for controls.

Figure 19:
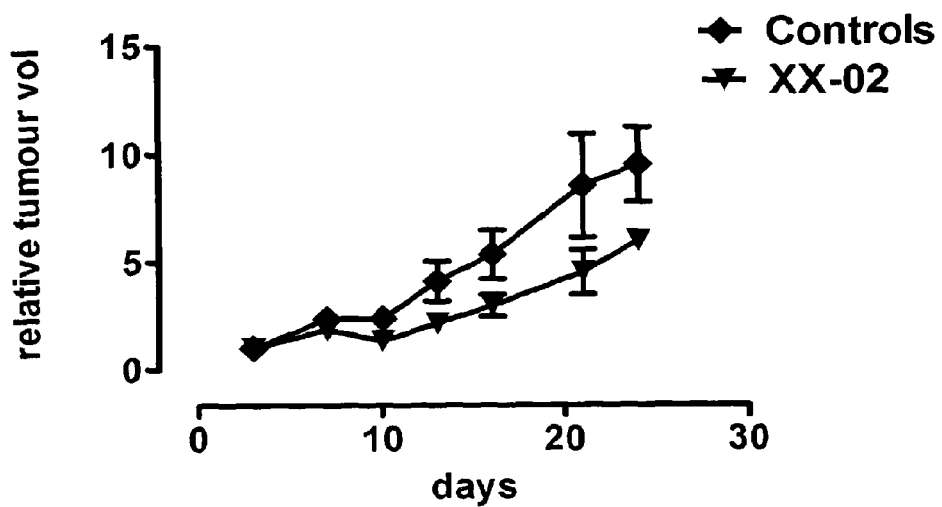

FIG. 19 is a graph of relative tumour volume as a function of time (days) for mouse xenografts of the mutant BRAF cell line A375, for treatment with comparison compound XX-02 and for controls.

SUMMARY OF THE INVENTION

One aspect of the invention pertains to certain compounds (for convenience, collectively referred to herein as "IP compounds"), as described herein.

Another aspect of the invention pertains to a composition (e.g., a pharmaceutical composition) comprising an IP compound, as described herein, and a pharmaceutically acceptable carrier or diluent.

Another aspect of the invention pertains to method of preparing a composition (e.g., a pharmaceutical composition) comprising the step of admixing an IP compound, as described herein, and a pharmaceutically acceptable carrier or diluent.

Another aspect of the present invention pertains to a method of treatment comprising administering to a subject in need of treatment a therapeutically-effective amount of an IP compound, as described herein, preferably in the form of a pharmaceutical composition.

Another aspect of the present invention pertains to an IP compound as described herein for use in a method of treatment of the human or animal body by therapy.

Another aspect of the present invention pertains to use of an IP compound, as described herein, in the manufacture of a medicament for use in treatment.

In one embodiment, the treatment is treatment of cancer.

In one embodiment, the cancer is solid tumour cancer.

In one embodiment, the cancer is pancreatic cancer; thyroid (e.g., follicular; undifferentiated papillary) cancer; colorectal cancer; seminoma; myelodysplastic syndrome (MDS); lung cancer (e.g., lung adenocarcinoma); liver cancer; leukemia (e.g., acute myelogenous leukemia (AML)); melanoma; bladder cancer; kidney cancer; breast cancer, ovarian cancer, bile duct cancer, or glioma.

In one embodiment, the cancer is pancreatic cancer.

In one embodiment, the cancer is thyroid cancer.

In one embodiment, the cancer is colorectal cancer.

In one embodiment, the cancer is seminoma.

In one embodiment, the cancer is myelodysplastic syndrome (MDS).

In one embodiment, the cancer is lung cancer.

In one embodiment, the cancer is lung adenocarcinoma.

In one embodiment, the cancer is liver cancer.

In one embodiment, the cancer is leukemia.

In one embodiment, the cancer is acute myelogenous leukemia (AML).

In one embodiment, the cancer is melanoma.

In one embodiment, the cancer is bladder cancer.

In one embodiment, the cancer is kidney cancer.

In one embodiment, the cancer is breast cancer.

In one embodiment, the cancer is ovarian cancer.

In one embodiment, the cancer is bile duct cancer.

In one embodiment, the cancer is glioma.

In one embodiment, the cancer is mutant RAS cancer (e.g., mutant RAS pancreatic cancer, etc.).

In one embodiment, the cancer is characterised by, or further characterised by, cancer stem cells.

In one embodiment, the treatment further comprises treatment with one or more additional therapeutic agents or therapies, for example, one or more additional anti-cancer agents or therapies.

Another aspect of the present invention pertains to a kit comprising (a) an IP compound, as described herein, preferably provided as a pharmaceutical composition and in a suitable container and/or with suitable packaging; and (b) instructions for use, for example, written instructions on how to administer the compound.

Another aspect of the present invention pertains to an IP compound obtainable by a method of synthesis as described herein, or a method comprising a method of synthesis as described herein.

Another aspect of the present invention pertains to an IP compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

The present relates to certain compounds which are structurally related to the following compounds:

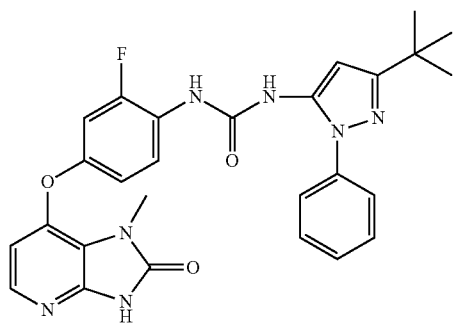

1-(5-tert-butyl-2-phenyl-2H-pyrazol-3-yl)-
3-[2-fluoro-4-(1-methyl-2-oxo-2,3-dihydro-1H-
imidazo[4,5-b]pyridin-7-yloxy)-
phenyl]-urea

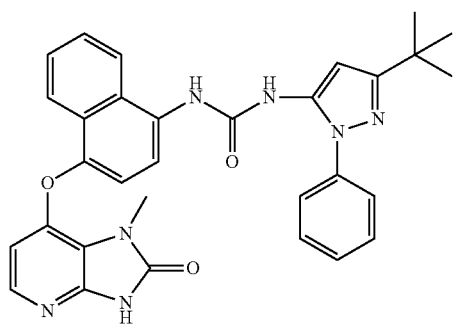

1-(5-tert-butyl-2-phenyl-2H-pyrazol-3-yl)-
3-[4-(1-methyl-2-oxo-2,3-dihydro-1H-
imidazo[4,5-b]pyridin-7-yloxy)-
naphthalen-1-yl]-urea In contrast to known compounds, the compounds of the present invention are characterized by a particular combination of structural motifs, specifically:

(A) a 1-methyl-2-oxo-2,3-dihydro-1H-imidazo[4,5-b]pyridin-7-yloxy motif:

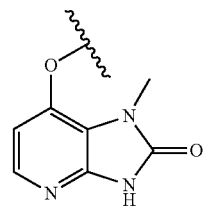 [SMILES: *Oc1ccnc2[nH]c(=O)n(C)c12]

(B) a linking 2-fluoro-phen-1,4-di-yl moiety or a linking naphth-1,4-di-yl motif:

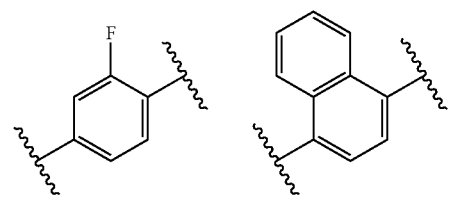 [SMILES: *c1ccc(*)c(F)c1 ; *c1ccc(*)c2ccccc12]

(C) a 1-(5-tert-butyl-2-phenyl-2H-pyrazol-3-yl)-ureyl motif, where the phenyl group optionally bears a meta- or para-substituent:

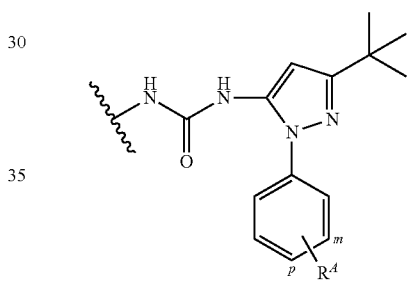

None of the known compounds have all three of these motifs. Furthermore, comparison studies with compounds (including known compounds) demonstrate that, surprisingly and unexpectedly, compounds having all three of the motifs (i.e., the claimed compounds) have substantially better activity against mutant RAS cancers, than comparison compounds which lack one or more of these motifs.

Thus, one aspect of the present invention pertains to compounds of the following formula, and pharmaceutically acceptable salts, hydrates, and solvates thereof (collectively referred to herein as "IP compounds"):

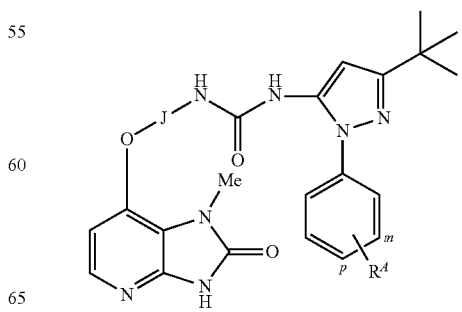

wherein -J- is independently:

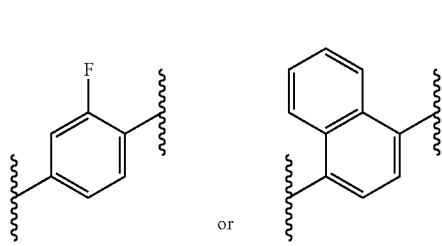

or ;

and wherein —R is independently —H, -Me, —F, —Cl, —Br, or —I;
and wherein —R is positioned meta- or para- on the phenyl ring.

In one embodiment, the compound is selected from compounds of the following formula, and pharmaceutically acceptable salts, hydrates, and solvates thereof, wherein —$R^A$ is independently —H, -Me, —F, —Cl, —Br, or —I, and wherein —$R^A$ is positioned meta- or para- on the phenyl ring:

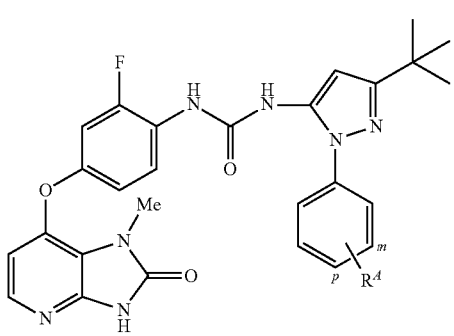

In one embodiment, the compound is selected from compounds of the following formula, and pharmaceutically acceptable salts, hydrates, and solvates thereof, wherein —$R^A$ is independently —H, -Me, —F, —Cl, —Br, or —I:

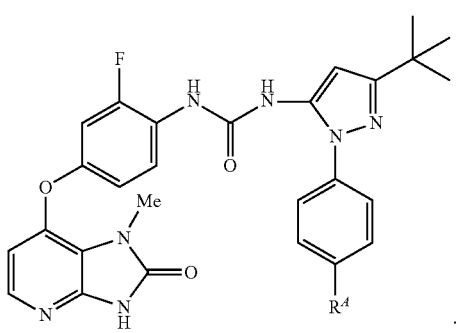

In one embodiment, the compound is selected from compounds of the following formula, and pharmaceutically acceptable salts, hydrates, and solvates thereof, wherein —$R^A$ is independently —H, -Me, —F, —Cl, —Br, or —I:

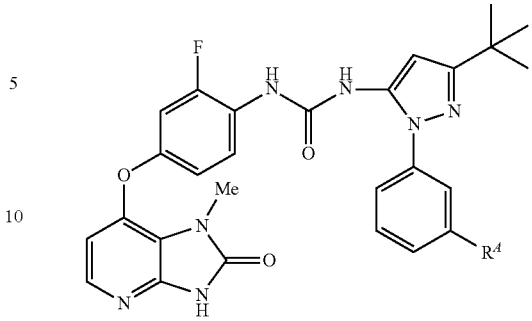

In one embodiment, —$R^A$ is independently —H, -Me, —F, or —Cl.
In one embodiment, —$R^A$ is independently —H or -Me.
In one embodiment, —$R^A$ is independently —H.
In one embodiment, —$R^A$ is independently -Me.
In one embodiment, —$R^A$ is independently —F or —Cl.
In one embodiment, —$R^A$ is independently —F.
In one embodiment, —$R^A$ is independently —Cl.

In one embodiment, the compound is selected from the following compound (i.e., AA-01), and pharmaceutically acceptable salts, hydrates, and solvates thereof:

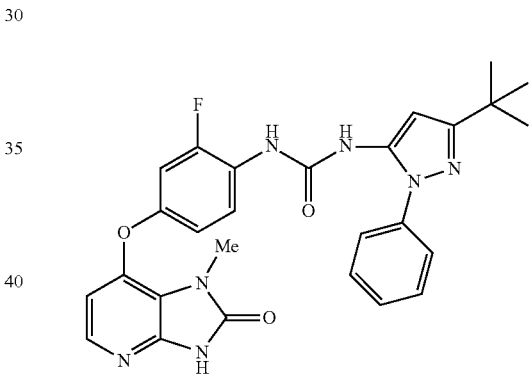

In one embodiment, the compound is selected from the following compound (i.e., AA-02), and pharmaceutically acceptable salts, hydrates, and solvates thereof:

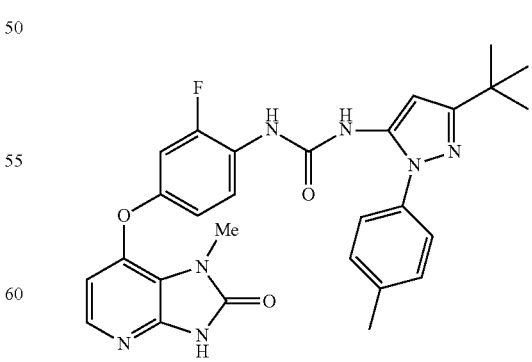

In one embodiment, the compound is selected from the following compound (i.e., AA-03), and pharmaceutically acceptable salts, hydrates, and solvates thereof:

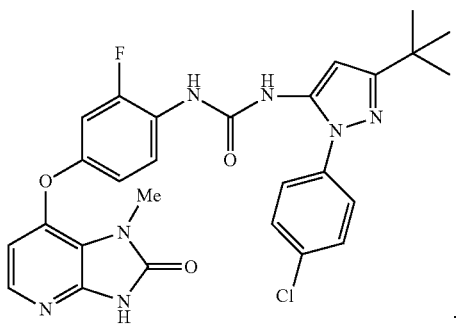

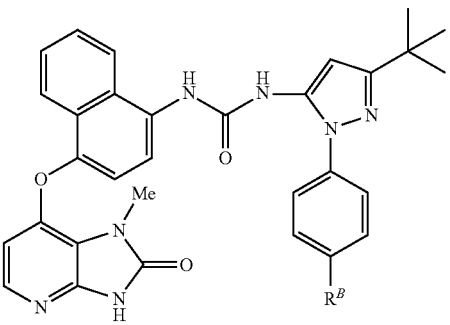

and pharmaceutically acceptable salts, hydrates, and solvates thereof, wherein —$R^B$ is independently —H, -Me, —F, —Cl, —Br, or —I:

In one embodiment, the compound is selected from the following compound (i.e., AA-04), and pharmaceutically acceptable salts, hydrates, and solvates thereof:

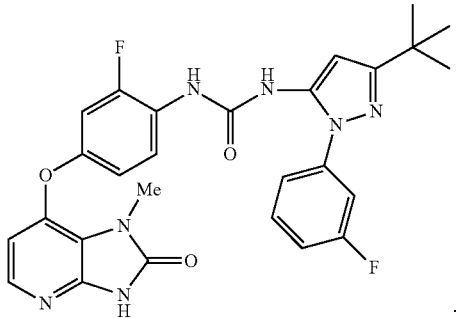 [SMILES: Cn1c(=O)[nH]c2nccc(Oc3ccc(NC(=O)Nc4cc(C(C)(C)C)nn4-c4cccc(F)c4)c(F)c3)c21]

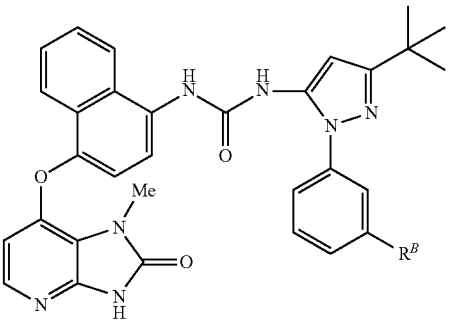

In one embodiment, —$R^B$ is independently —H, -Me, —F, or —Cl.

In one embodiment, —$R^B$ is independently —H or -Me.

In one embodiment, —$R^B$ is independently —H.

In one embodiment, —$R^B$ is independently -Me.

In one embodiment, —$R^B$ is independently —F or —Cl.

In one embodiment, —$R^B$ is independently —F.

In one embodiment, —$R^B$ is independently —Cl.

In one embodiment, the compound is selected from the following compound (i.e., BB-01), and pharmaceutically acceptable salts, hydrates, and solvates thereof:

In one embodiment, the compound is selected from compounds of the following formula, and pharmaceutically acceptable salts, hydrates, and solvates thereof, wherein —$R^B$ is independently —H, -Me, —F, —Cl, —Br, or —I, and wherein —$R^B$ is positioned meta- or para- on the phenyl ring:

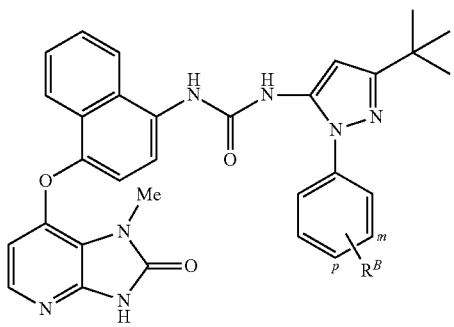

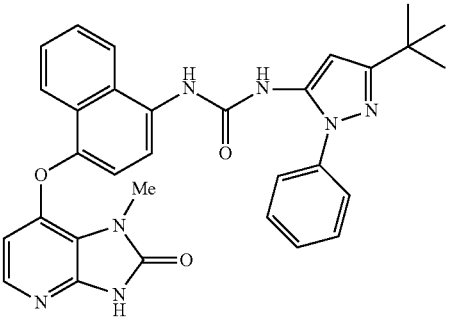

In one embodiment, the compound is selected from compounds of the following formula, and pharmaceutically acceptable salts, hydrates, and solvates thereof, wherein —$R^B$ is independently —H, -Me, —F, —Cl, —Br, or —I:

In one embodiment, the compound is selected from the following compound (i.e., BB-02), and pharmaceutically acceptable salts, hydrates, and solvates thereof:

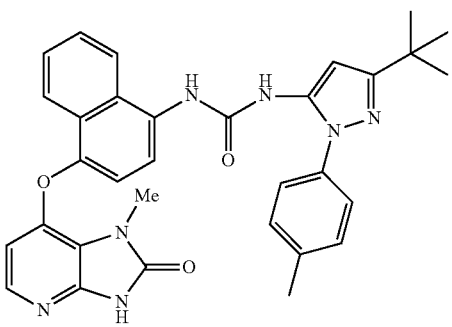

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., -J-, -R, -R$^A$, -R$^B$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to IP compounds, as described herein, in substantially purified form and/or in a form substantially free from contaminants.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric form. For example, in one embodiment, the substantially purified form refers to a mixture of stereoisomers, i.e., purified with respect to other compounds. In one embodiment, the substantially purified form refers to one stereoisomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers. In one embodiment, the contaminants refer to other compounds and other stereoisomers.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that specifically excluded from the term "isomers," as used herein, are structural (or constitutional) isomers (i.e., isomers which differ in the connections between atoms rather than merely by the position of atoms in space). For example, a reference to a tert-butyl group, —C(CH$_3$)$_3$, is not to be construed as a reference to its structural isomer, iso-butyl, —CH$_2$CH(CH$_3$)$_2$. Similarly, a reference to para-chlorophenyl is not to be construed as a reference to its structural isomer, meta-chlorophenyl.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures thereof.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is cationic, or has a functional group which may be cationic (e.g., —NH— may be —NH$_2$$^+$—), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemical Synthesis

Methods for the chemical synthesis of compounds of the present invention are described herein. These and/or other well known methods may be modified and/or adapted in known ways in order to facilitate the synthesis of additional compounds within the scope of the present invention.

Descriptions of general laboratory methods and procedures, useful for the preparation of the compounds described herein, are provided in *Vogel's Textbook of Practical Organic Chemistry*, 5th Edition, 1989, (Editors: Furniss, Hannaford, Smith, and Tatchell) (published by Longmann, UK).

Methods for the synthesis of pyridine compounds in particular are described in *Heterocyclic Chemistry*, 3rd Edition, 1998, (Editors: Joule, Mills, and Smith) (published by Chapman & Hall, UK).

The IP compounds described herein may be prepared via intermediates (2). These intermediates may be prepared from commercially available starting material, 2-amino-3-nitro-4-chloropyridine (1), and 3-fluoro-4-aminophenol ($R^1$ is —H and $R^2$ is —F) or 4-amino-1-naphthol ($R^1$ and $R^2$ together are —CH═CH—). Intermediates (2) are then protected selectively at the amino group, for example as a BOC carbamate, to afford intermediates (3).

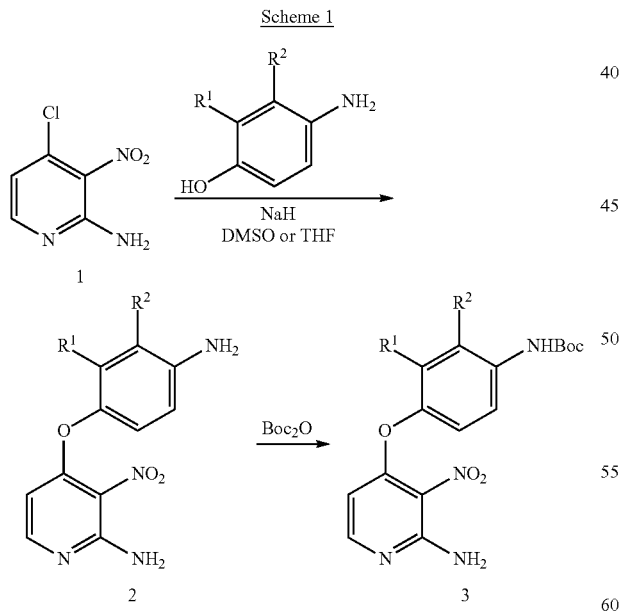

The intermediates (3) can also be obtained directly from 2-amino-3-nitro-4-chloropyridine (1) and N-BOC-protected 3-fluoro-4-aminophenol or N-BOC-protected 4-amino-1-naphthol.

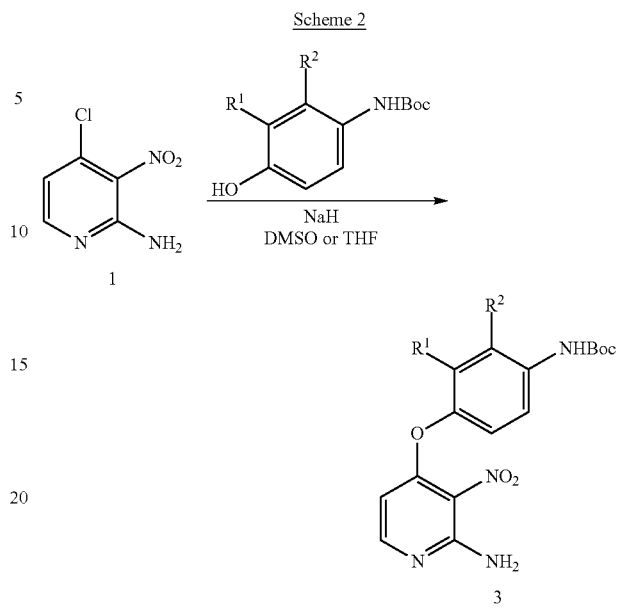

The nitro group of the protected intermediates (3) may be reduced to an amino group with Pd/C and ammonium formate or hydrogen, or with $NiCl_2$ and $NaBH_4$, to give the diamino intermediates (4).

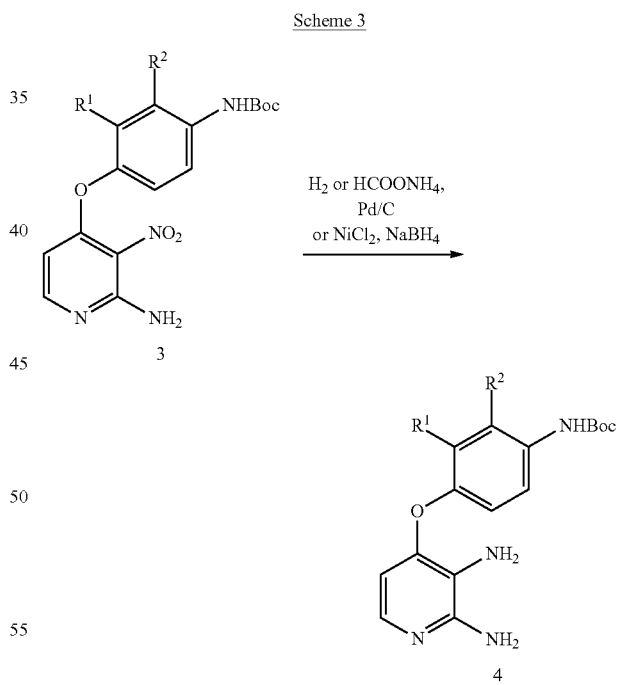

The intermediates (8), alkylated at N3 (by respect to the pyridine ring), may be prepared from intermediates (4). The more nucleophilic 3-amino group on intermediates (4) is converted to ethyl carbamate, to afford intermediates (5), and the BOC group is removed with TFA to afford intermediates (6). Deprotonation of the acidic carbamate proton with NaH gives an anion on N3 that is alkylated to afford the intermediates (7). Cyclisation of intermediates (7), in the presence of base, gives the corresponding intermediates (8).

Scheme 4

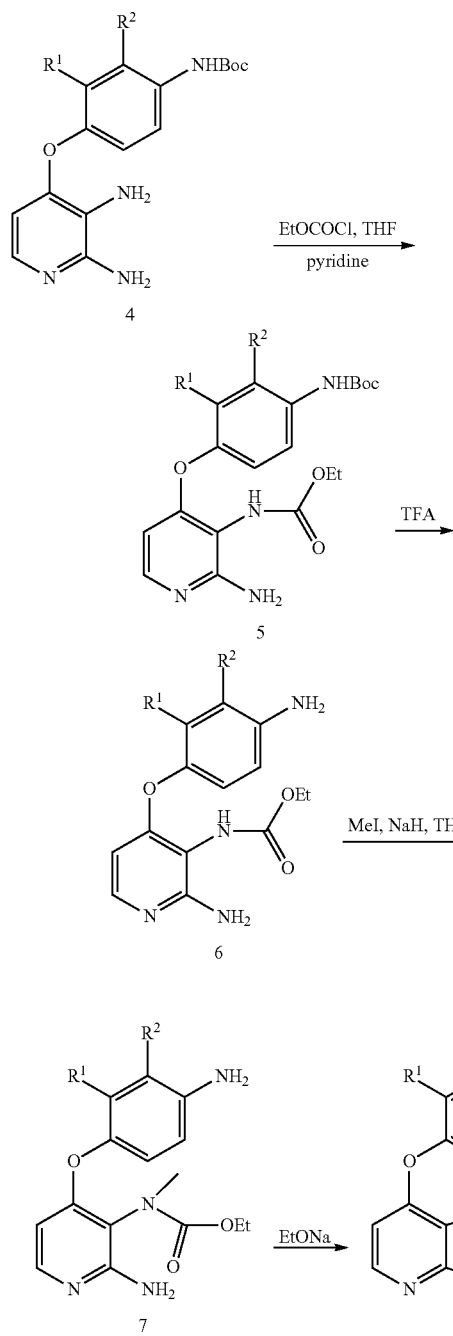

Scheme 5

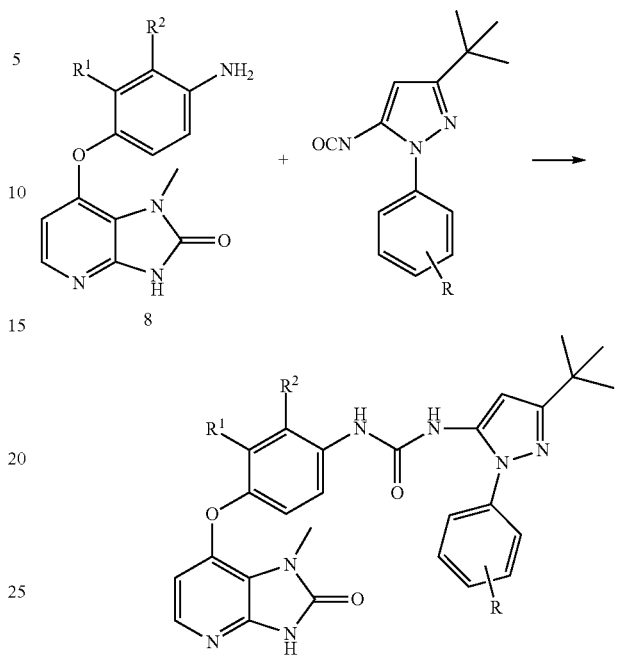

The intermediates (8) are reacted with 3-tert-butyl-5-isocyanato-1-aryl-1H-pyrazoles to afford the corresponding ureas. The respective isocyanates can be obtained either by the reaction of amines with phosgene, triphosgene or their derivatives, or by conversion of the corresponding carboxylic acids to acyl azides with, for example, diphenyl phosphoryl azide, followed by Curtius rearrangement. The aryl group on the pyrazole may be, for example, unsubstituted or substituted (e.g., meta or para-substituted) with an alkyl group (e.g., -Me) or a halogen atom (e.g., —F, —Cl, —Br, —I).

Compositions

One aspect of the present invention pertains to a composition (e.g., a pharmaceutical composition) comprising an IP compound, as described herein, and a pharmaceutically acceptable carrier, diluent, or excipient.

In one embodiment, the composition further comprises one or more (e.g., 1, 2, 3, 4) additional therapeutic agents, as described herein.

Another aspect of the present invention pertains to a method of preparing a composition (e.g., a pharmaceutical composition) comprising admixing an IP compound, as described herein, and a pharmaceutically acceptable carrier, diluent, or excipient.

Another aspect of the present invention pertains to a method of preparing a composition (e.g., a pharmaceutical composition) comprising admixing an IP compound, as described herein; one or more (e.g., 1, 2, 3, 4) additional therapeutic agents, as described herein; and a pharmaceutically acceptable carrier, diluent, or excipient.

Uses

The compounds described herein are useful, for example, in the treatment of cancer, for example, mutant RAS cancer.

For the avoidance of doubt, the term "mutant RAS cancer" is used herein to refer to cancer that is characterised by (e.g., driven by) mutant RAS, for example, by one or more mutations (e.g., gain-of-function mutations) in one of the RAS genes (i.e., HRAS, KRAS, and NRAS). As discussed herein, the most common RAS mutations involve codons for one or more of glycine 12 (G12), glycine 13 (G13) and glutamine 61 (Q61).

Use in Methods of Therapy

Another aspect of the present invention pertains to an IP compound, as described herein, for use in a method of treatment of the human or animal body by therapy.

Another aspect of the present invention pertains to an IP compound, as described herein, in combination with one or more (e.g., 1, 2, 3, 4) additional therapeutic agents, as described herein, for use in a method of treatment of the human or animal body by therapy.

Use in the Manufacture of Medicaments

Another aspect of the present invention pertains to use of an IP compound, as described herein, in the manufacture of a medicament for use in treatment.

In one embodiment, the medicament comprises the IP compound.

Another aspect of the present invention pertains to use of an IP compound, as described herein, and one or more (e.g., 1, 2, 3, 4) additional therapeutic agents, as described herein, in the manufacture of a medicament for use in treatment.

In one embodiment, the medicament comprises the IP compound and the one or more (e.g., 1, 2, 3, 4) additional therapeutic agents.

Methods of Treatment

Another aspect of the present invention pertains to a method of treatment comprising administering to a patient in need of treatment a therapeutically effective amount of an IP compound, as described herein, preferably in the form of a pharmaceutical composition.

Another aspect of the present invention pertains to a method of treatment comprising administering to a patient in need of treatment a therapeutically effective amount of an IP compound, as described herein, preferably in the form of a pharmaceutical composition, and one or more (e.g., 1, 2, 3, 4) additional therapeutic agents, as described herein, preferably in the form of a pharmaceutical composition.

Conditions Treated

In one embodiment, the treatment is treatment of cancer.

In one embodiment, the cancer is lung cancer, small cell lung cancer, non-small cell lung cancer, gastrointestinal cancer, stomach cancer, bowel cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the cancer is:
- a carcinoma, for example a carcinoma of the bladder, breast, colon/rectum (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
- a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
- a hematopoietic tumor of myeloid lineage, for example acute and chronic myelogenous leukemias, myelodysplastic syndrome, or promyelocytic leukemia;
- a tumour of mesenchymal origin, for example fibrosarcoma or habdomyosarcoma;
- a tumor of the central or peripheral nervous system, for example astrocytoma, neuroblastoma, glioma or schwannoma;
- melanoma; seminoma; teratocarcinoma; osteosarcoma; xenoderoma pigmentoum; keratoctanthoma; thyroid follicular cancer; or Kaposi's sarcoma.

In one embodiment, the cancer is solid tumour cancer.

In one embodiment, the cancer is pancreatic cancer; thyroid (e.g., follicular; undifferentiated papillary) cancer; colorectal cancer; seminoma; myelodysplastic syndrome (MDS); lung cancer (e.g., lung adenocarcinoma); liver cancer; leukemia (e.g., acute myelogenous leukemia (AML)); melanoma; bladder cancer; kidney cancer; breast cancer, ovarian cancer, bile duct cancer, or glioma.

In one embodiment, the cancer is pancreatic cancer.

In one embodiment, the cancer is thyroid cancer.

In one embodiment, the cancer is colorectal cancer.

In one embodiment, the cancer is seminoma.

In one embodiment, the cancer is myelodysplastic syndrome (MDS).

In one embodiment, the cancer is lung cancer.

In one embodiment, the cancer is lung adenocarcinoma.

In one embodiment, the cancer is liver cancer.

In one embodiment, the cancer is leukemia.

In one embodiment, the cancer is acute myelogenous leukemia (AML).

In one embodiment, the cancer is melanoma.

In one embodiment, the cancer is bladder cancer.

In one embodiment, the cancer is kidney cancer.

In one embodiment, the cancer is breast cancer.

In one embodiment, the cancer is ovarian cancer.

In one embodiment, the cancer is bile duct cancer.

In one embodiment, the cancer is glioma.

In one embodiment, the cancer is mutant RAS cancer (e.g., mutant RAS pancreatic cancer, etc.).

In one embodiment, the cancer is characterised by, or further characterised by, cancer stem cells.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of cell migration (the spread of cancer cells to other parts of the body), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, reducing the severity of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development.

One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The IP compounds described herein may also be used as part of an in vitro assay, for example, in order to determine whether a candidate host is likely to benefit from treatment with the compound in question.

The IP compounds described herein may also be used as a standard, for example, in an assay, in order to identify other compounds, other anti-cancer agents, etc.

Kits

One aspect of the invention pertains to a kit comprising (a) an IP compound as described herein, or a composition comprising an IP compound as described herein, e.g., preferably provided in a suitable container and/or with suitable packaging; and (b) instructions for use, e.g., written instructions on how to administer the compound or composition.

In one embodiment, the kit further comprises one or more (e.g., 1, 2, 3, 4) additional therapeutic agents, as described herein.

The written instructions may also include a list of indications for which the active ingredient is a suitable treatment.

Routes of Administration

The IP compound or pharmaceutical composition comprising the IP compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomiser or dry powder delivery device); ocular (e.g., by eyedrops); pulmonary (e.g., by inhalation or insufflation therapy using, e.g., an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the IP compound to be administered alone, it is preferable to present it as a pharmaceutical formulation (e.g., composition, preparation, medicament) comprising at least one IP compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one IP compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's*

*Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringers Solution, or Lactated Ringer's Injection. Typically, the concentration of the compound in the liquid is from about 1 ng/mL to about 10 µg/m L, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the IP compounds, and compositions comprising the IP compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular IP compound, the route of administration, the time of administration, the rate of excretion of the IP compound, the duration of the treatment, other drugs, compounds, and/or materials used in combination, the severity of the condition, and the species, sex, age, weight, condition, general health, and prior medical history of the patient. The amount of IP compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the IP compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

All starting materials, reagents and solvents for reactions were reagent grade and used as purchased. Chromatography solvents were HPLC grade and were used without further purification. Reactions were monitored by thin layer chromatography (TLC) analysis using Merck silica gel 60 F-254 thin layer plates. Flash column chromatography was carried out on Merck silica gel 60 (0.015-0.040 mm) or in disposable Isolute Flash Si and Si II silica gel columns. Preparative TLC was performed on either Macherey-Nagel [809 023] pre-coated TLC plates SIL G-25 $UV_{254}$ or Analtech [2015] pre-coated preparative TLC plates, 2000 µm with $UV_{254}$. LCMS analyses were performed on a Micromass LCT/ Water's Alliance 2795 HPLC system with a Discovery 5 µm, C18, 50 mm×4.6 mm i.d. column from Supelco at a temperature of 22° C. using the following solvent systems: Solvent A: Methanol; Solvent B: 0.1% formic acid in water at a flow rate of 1 mL/min. Gradient starting with 10% A/90% B from 0-0.5 minutes then 10% A/90% B to 90% A/10% B from 0.5 minutes to 6.5 minutes and continuing at 90% A/10% B up to 10 minutes. From 10-10.5 minutes the gradient reverted back to 10% A/90% where the concentrations remained until 12 minutes. UV detection was at 254 nm and ionisation was positive or negative ion electrospray. Molecular weight scan range is 50-1000. Samples were supplied as 1 mg/mL in DMSO or methanol with 3 μL injected on a partial loop fill. NMR spectra were recorded in DMSO-$d_6$ on a Bruker Advance 500 MHz spectrometer.

Synthesis 1

Tert-butyl 2-fluoro-4-hydroxyphenylcarbamate

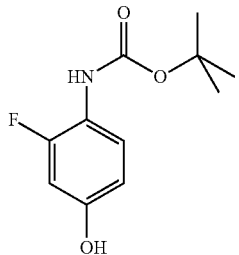 [SMILES: CC(C)(C)OC(=O)Nc1ccc(O)cc1F]

4-Amino-3-fluorophenol (10.61 g, 83.5 mmol) was added to a molten mixture of Boc$_2$O (18.29 g, 83.8 mmol) and InCl$_3$ (188 mg, 0.85 mmol) at 35° C. The black mixture was stirred at 35° C. for 2 hours, during which time it turned into a thick black oil. The mixture was then diluted with EtOAc (200 mL) and H$_2$O (200 mL) and stirring was continued for 10 minutes. The layers were separated and the organic layer was washed with H$_2$O (3×200 mL), dried (MgSO$_4$), filtered and concentrated to dryness. The resulting black oil was redissolved in CH$_2$Cl$_2$ (50 mL) and loaded onto a silica gel column. Elution with 5→7% EtOAc in CH$_2$Cl$_2$ furnished the title compound as a light yellow, crystalline solid.

Yield: 16.7 g (90%). $^1$H-NMR (DMSO-$d_6$), δ (ppm), J (Hz): 1.42 (s, 9H, C(CH$_3$)$_3$), 6.50-6.57 (m, 2H, ArH), 7.11-7.21 (m, 1H, ArH), 8.45 (bs, 1H, OH), 9.63 (s, 1H, NHBoc); $^{13}$C-NMR (DMSO-$d_6$), δ (ppm), J (Hz): 28.0, 78.6, 102.7 (d, $J_{FH}$=22.2), 110.8 (d, $J_{FH}$=2.7), 117.1 (d, $J_{FH}$=12.6), 127.2, 153.7, 155.5 (d, $J_{FH}$=11.3), 156.1 (d, $J_{FH}$=246); $^{19}$F-NMR (DMSO-$d_6$), δ (ppm): −121.6; LC-MS (3.94 min): m/z calcd. for C$_{11}$H$_{14}$FNO$_3$ [M-C(CH$_3$)$_3$]$^+$: 172.0; found: 172.0.

Synthesis 2

Tert-butyl 4-(2-amino-3-nitropyridin-4-yloxy)-2-fluorophenylcarbamate (3a)

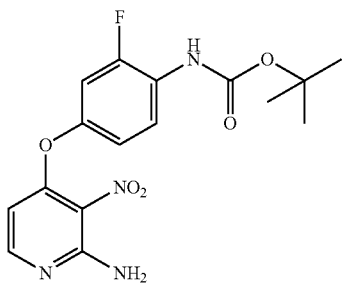 [SMILES: CC(C)(C)OC(=O)Nc1ccc(Oc2ccnc(N)c2[N+](=O)[O-])cc1F]

Dry DMSO (20 mL) was added to NaH (1.029 g of a 60% dispersion in mineral oil, 25.7 mmol) in a round bottom flask under argon. After 5 minutes, solid tert-butyl 2-fluoro-4-hydroxyphenylcarbamate (5.59 g, 24.6 mmol) was added in three portions, giving a dark solution, which, after 15 minutes of stirring at room temperature, was treated with 4-chloro-3-nitropyridin-2-amine (4.23 g, 24.4 mmol) at once. The dark red solution was heated to 110° C. for 1 hour and allowed to cool down to room temperature. EtOAc (150 mL) and H$_2$O (200 mL) were subsequently added to the solution and the organic layer was isolated. The aqueous layer was extracted with EtOAc (3×100 mL) and the combined organic layers were washed once with saturated NaHCO$_3$ (150 mL), dried (MgSO$_4$), filtered, and concentrated to dryness to give a bright yellow solid. This material was used in the next step without further purification.

Yield: 8.68 g (98%). $^1$H-NMR (DMSO-$d_6$), δ (ppm), J (Hz): 1.46 (s, 9H, C(CH$_3$)$_3$), 6.08 (d, 1H, $^3J_{HH}$=5.5, PyrH), 7.01 (m, 1H, ArH), 7.18 (br s, 2H, NH$_2$), 7.22 (m, 1H, ArH), 7.67 (m, 1H, ArH), 8.04 (d, 1H, $^3J_{HH}$=5.5, PyrH), 9.03 (s, 1H, NHBoc); $^{19}$F-NMR (DMSO-$d_6$), δ (ppm): −120.7; LC-MS (4.72 min): m/z calcd. for C$_{16}$H$_{17}$FN$_4$O$_5$ [M+H$^+$]: 365.0; found: 365.0.

Synthesis 3

Tert-butyl 4-(2,3-diaminopyridin-4-yloxy)-2-fluorophenylcarbamate (4a)

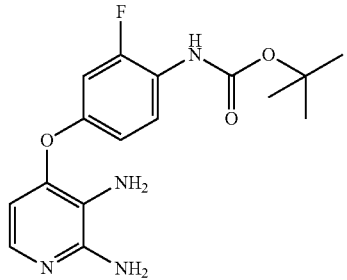 [SMILES: CC(C)(C)OC(=O)Nc1ccc(Oc2ccnc(N)c2N)cc1F]

Pd/C (1.09 g) was added to a yellow solution of tert-butyl 4-(2-amino-3-nitropyridin-4-yloxy)-2-fluorophenylcarbamate (3a) (6.20 g, 17.0 mmol) in EtOAc/EtOH (90/150 mL) and the black mixture was stirred under a nitrogen atmosphere for 5 hours and filtered over Celite. The dark brown filtrate was concentrated to dryness, redissolved in CH$_2$Cl$_2$ (20 mL) and loaded onto a silica gel column. The products were eluted with EtOAc and the fractions containing the title compound were evaporated to dryness. The orange oil was dissolved in CH$_2$Cl$_2$ and an equal amount of hexane was added. The solution was concentrated to dryness to give an orange foam.

Yield: 4.30 g (76%). $^1$H-NMR (DMSO-$d_6$), δ (ppm), J (Hz): 1.45 (s, 9H, C(CH$_3$)$_3$), 4.47 (s, 2H, NH$_2$), 5.61 (s, 2H, NH$_2$), 6.09 (d, 1H, $^3J_{HH}$=5.5, PyrH), 6.76 (m, 1H, ArH), 6.87 (m, 1H, ArH), 7.28 (d, 1H, $^3J_{HH}$=5.5, PyrH), 7.47 (m, 1H, ArH), 8.82 (s, 1H, NHBoc); $^{13}$C-NMR (DMSO-$d_6$), δ (ppm), J (Hz): 28.0, 79.1, 104.4, 105.9 (d, $J_{FH}$=23.1), 113.4 (d, $J_{FH}$=3.1), 120.3, 121.5 (d, $J_{FH}$=12.2), 126.1, 135.7, 146.2, 150.5, 153.1 (d, $J_{FH}$=10.1), 153.3, 155.1 (d, $J_{FH}$=248); $^{19}$F-NMR (DMSO-$d_6$), δ (ppm): −120.7; LC-MS (2.69 min): m/z calcd. for C$_{16}$H$_{20}$FN$_4$O$_3$ [M+H$^+$]: 335.2; found: 335.3.

Synthesis 4

Ethyl 4-(4-N-(tert-butoxycarbonyl)-amino-3-fluoro-phenoxy)-2-aminopyridin-3-yl-carbamate (5a)

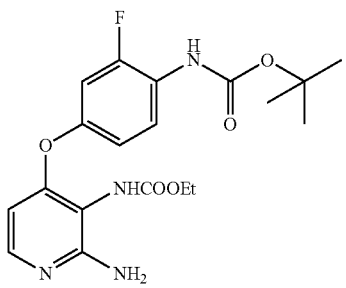

4-(4-N-(tert-butoxycarbonyl)-amino-3-fluorophenyloxy)-2,3-diaminopyridine (4a) (2.5 g, 7.5 mmol) was dissolved in dry THF (50 mL) under stirring, pyridine (1.2 mL, 15 mmol) was added and the solution was cooled at 0° C. Ethyl chloroformate (0.77 mL, 8.0 mmol) was added at once. After 30 minutes, the reaction mixture was allowed to reach room temperature and stirred for further 24 hours. The solvent was evaporated under vacuum and the residue partitioned between DCM and saturated aqueous $Na_2CO_3$. The organic layer was washed with $H_2O$, dried over $MgSO_4$ and evaporated. The residue was purified by column chromatography (eluent gradient DCM to EtOAc) to afford the title compound as a foam.

Yield: 1.13 g, 37%. $^1$H-NMR δ: 1.17 (t, 3H, $CH_{3,Et}$, J=7.1 Hz), 1.45 (s, 9H, tBu), 4.02 (q, 2H, J=7.1, $CH_{2,Et}$), 5.89 (s, 2H, $NH_{2,Py2}$), 5.98 (d, 1H, J=5.7, $H_{Py}$), 6.83 (d, 1H, $H_{arom}$), 6.96 (d, 1H, $H_{arom}$), 7.55 (t, 1H, $H_{arom}$), 7.73 (d, 1H, J=5.7, $H_{Py}$), 8.29 (br s, 1H, $NH_{Py3}$), 9.39 (s, 1H, NHBoc).

Synthesis 5

Ethyl 4-(4-amino-3-fluorophenoxy)-2-aminopyridin-3-yl-carbamate (6a)

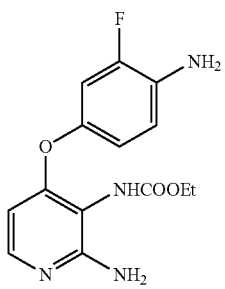

Ethyl 4-(4-N-(tert-butoxycarbonyl)-amino-3-fluorophenoxy)-2-aminopyridin-3-yl-carbamate (5a) (1.13 g, 2.8 mmol) was dissolved in TFA (8 mL), a few drops of water were added and the reaction mixture was stirred for 2 hours at room temperature. The TFA was evaporated, the residue dissolved in water (20 mL), neutralized with saturated aqueous $Na_2CO_3$ and extracted with DCM (2×20 mL). The organic layer was dried and evaporated to afford the title compound.

Yield: 730 mg, 86%. $^1$H-NMR δ: 1.17 (t, 3H, J=7.1, $CH_{3,Et}$), 4.05 (q, 2H, J=7.0, $CH_{2,Et}$), 5.04 (s, 2H, $NH_{2,Ph}$), 5.71 (s, 2H, $NH_{2,Py}$), 5.86 (d, 1H, J=5.7, $H_{Py}$), 6.64 (d, 1H, $H_{arom}$), 6.73-6.82 (m, 2H, $H_{arom}$), 7.68 (d, 1H, J=5.7, $H_{Py}$), 8.23 (br s, 1H, $NH_{Py3}$). LC-MS: m/z 307 ([M+H]$^+$, 100).

Synthesis 6

Ethyl 4-(4-amino-3-fluorophenoxy)-2-aminopyridin-3-yl-methyl-carbamate (7a)

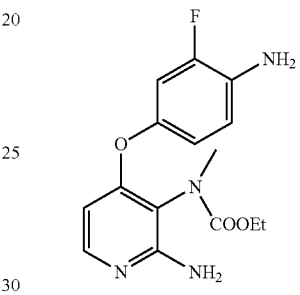

Ethyl 4-(4-amino-3-fluorophenoxy)-2-aminopyridin-3-yl-carbamate (6a) (480 mg, 1.6 mmol) was dissolved in dry THF (8 mL) and cooled at 0° C. Sodium hydride (60% in mineral oil, 80 mg, 2.0 mmol) was added, and the reaction mixture was stirred for 40 minutes at 0° C. Methyl iodide (130 μL, 1.8 mmol) was added at 0° C. The ice bath was removed, and the mixture was stirred at room temperature for 18 hours. The solvent was evaporated and the residue partitioned between DCM and distilled water. The organic layer was dried and evaporated, and the residue washed with diethyl ether to afford the title compound as a brown solid.

Yield: 322 mg, 63%. $^1$H-NMR δ: 1.09 (t, 3H, J=7.0, $CH_{3,Et}$), 3.00 (s, 3H, $CH_3N$), 3.90-4.10 (m, 2H, $CH_{2,Et}$), 5.07 (s, 2H, $NH_{2,Ph}$), 5.87 (d, 1H, $H_{Py}$), 6.03 (s, 2H, $NH_{2,Py}$), 6.63 (t, 1H, $H_{arom}$), 6.77-6.81 (m, 2H, $H_{arom}$), 7.75 (d, 1H, $H_{Py}$).

Synthesis 7

7-(4-Amino-3-fluorophenoxy)-1-N-methyl-1H-imidazo[4,5-b]pyridin-2(3H)-one (8a)

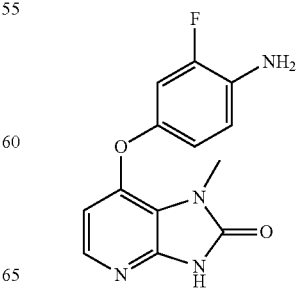

Ethyl 4-(4-amino-3-fluorophenoxy)-2-aminopyridin-3-yl-methyl-carbamate (7a) (320 mg, 1.0 mmol) was suspended in a solution of EtONa in EtOH (4 mL), obtained from dissolving sodium (480 mg, 21 mmol) in ethanol (9 mL). The suspension was heated under microwave irradiation for 1 hour (100° C., 100 W). The mixture was cooled at room temperature and the solvent was evaporated. The residue was dissolved in water and was acidified with AcOH to pH 4. The precipitate formed was recovered by filtration, to afford the title compound.

Yield: 188 mg, 67%. $^1$H-NMR δ: 3.46 (s, 3H, CH$_3$N), 5.11 (s, 2H, NH$_2$), 6.35 (d, 1H, J=5.9, H$_{Py}$), 6.77-6.82 (m, 2H, H$_{arom}$), 6.99 (d, 1H, H$_{arom}$), 7.76 (d, 1H, J=6.0, H$_{Py}$), 11.54 (s, 1H, NH$_{Py}$).

Synthesis 8

1-(3-Tert-butyl-1-phenyl-1H-pyrazol-5-yl)-3-(2-fluoro-4-(1-N-methyl-2-oxo-2,3-dihydro-1H-imidazo[4,5-b]pyridin-7-yloxy)phenyl)urea (AA-01)

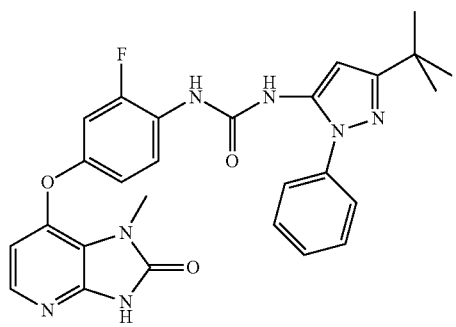 [SMILES: Cn1c(=O)[nH]c2nccc(Oc3ccc(NC(=O)Nc4cc(C(C)(C)C)nn4-c4ccccc4)c(F)c3)c21]

3-Tert-butyl-1-phenyl-1H-pyrazol-5-amine (550 mg, 1.8 mmol) was dissolved in CH$_2$Cl$_2$ (25 mL) and an equal volume of saturated NaHCO$_3$ (aq) was added. The biphasic mixture was stirred and cooled to 0° C. with an ice/water bath. After 10 minutes, 2 equiv. of a 1.9 M solution of phosgene in toluene were added. The mixture was vigorously stirred for 10 minutes, the organic layer was isolated, washed with H$_2$O, dried (MgSO$_4$) and concentrated to about 5 mL. This solution was added to a solution of the 7-(4-amino-3-fluorophenoxy)-1-N-methyl-1H-imidazo[4,5-b]pyridin-2(3H)-one (8a) (200 mg, 1.4 mmol) in THF. The solution was stirred for 15 hours at room temperature, the solvents were evaporated and the solid residue was washed with Et$_2$O and CH$_2$Cl$_2$ to afford the title compound as a white solid.

Yield: 200 mg, 53%. $^1$H NMR, δ: 1.28 (s, 9H, tert-Bu), 3.42 (s, 3H, CH$_3$), 6.39 (s, 1H, H$_{Pyz,4}$), 6.49 (d, 1H, J=5.9, H$_{Py,5}$), 6.99 (dd, 1H, J=1.6, 9.0, H$_{arom}$), 7.21 (dd, 1H, J=11.9, 2.7, H$_{arom}$), 7.40-7.45 (m, 1H, H$_{arom}$), 7.50-7.58 (m, 4H, H$_{arom}$), 7.81 (d, 1H, J=5.9, H$_{Py,6}$), 8.10 (t, 1H, J=9.1, H$_{arom}$), 8.80 (s, 1H, NH$_{urea}$), 8.93 (s, 1H, NH$_{urea}$), 11.63 (bs, 1H, NH$_{Py2}$). LC-MS: m/z 516 ([M]$^+$, 100). HRMS (EI): m/z calcd for C$_{27}$H$_{27}$N$_7$O$_3$ ([M+H]$^+$): 516.2154; found: 516.2152.

Synthesis 9

1-(3-Tert-butyl-1-p-tolyl-1H-pyrazol-5-yl)-3-(2-fluoro-4-(1-N-methyl-2-oxo-2,3-dihydro-1H-imidazo[4,5-b]pyridin-7-yloxy)phenyl)urea (AA-02)

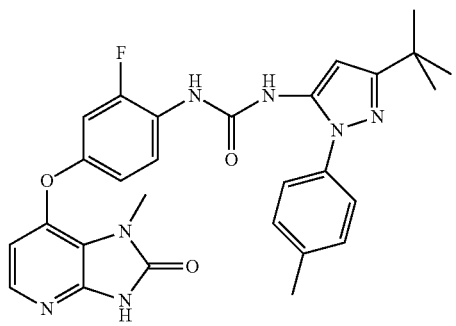 [SMILES: Cc1ccc(-n2nc(C(C)(C)C)cc2NC(=O)Nc2ccc(Oc3ccnc4[nH]c(=O)n(C)c34)cc2F)cc1]

The title compound was prepared from 3-tert-butyl-1-p-tolyl-1H-pyrazol-5-amine (458 mg, 2 mmol) and 7-(4-amino-3-fluorophenoxy)-1-N-methyl-1H-imidazo[4,5-b]pyridin-2(3H)-one (8a) (110 mg, 0.4 mmol) by the same method as described for (AA-01), as an off-white solid.

Yield: 150 mg, 71%. $^1$H NMR, δ: 1.27 (s, 9H, tert-Bu), 2.38 (s, 3H, Ph-CH$_3$), 3.42 (s, 3H, N—CH$_3$), 6.37 (s, 1H, H$_{Pyz,4}$), 6.49 (d, 1H, J=5.9, H$_{Py,5}$), 6.96 (dd, 1H, H$_{arom}$), 7.20 (d, 1H, H$_{arom}$), 7.34 (d, 2H, J=8.3, H$_{arom}$), 7.39 (d, 2H, J=8.4, H$_{arom}$), 7.81 (d, 1H, J=5.9, H$_{Py,6}$), 8.11 (t, 1H, H$_{arom}$), 8.74 (s, 1H, NH$_{urea}$), 8.92 (s, 1H, NH$_{urea}$), 11.61 (bs, 1H, NH$_{Py2}$). LC-MS: m/z 530 ([M+H]$^+$, 100).

Synthesis 10

1-(3-Tert-butyl-1-(4-chlorophenyl)-1H-pyrazol-5-yl)-3-(2-fluoro-4-(1-N-methyl-2-oxo-2,3-dihydro-1H-imidazo[4,5-b]pyridin-7-yloxy)phenyl)urea (AA-03)

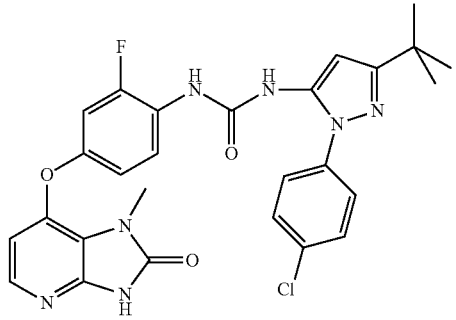 [SMILES: Cn1c(=O)[nH]c2nccc(Oc3ccc(NC(=O)Nc4cc(C(C)(C)C)nn4-c4ccc(Cl)cc4)c(F)c3)c21]

The title compound was prepared from 3-tert-butyl-1-(4-chlorophenyl)-1H-pyrazol-5-amine (375 mg, 1.5 mmol) and 7-(4-amino-3-fluorophenoxy)-1-N-methyl-1H-imidazo[4,5- b]pyridin-2(3H)-one (8a) (150 mg, 0.55 mmol) by the same method as described for (AA-01), as an off-white solid.

Yield: 190 mg, 63%. $^1$H NMR, δ: 1.28 (s, 9H, tert-Bu), 3.42 (s, 3H, CH$_3$), 6.39 (s, 1H, H$_{Pyz,4}$), 6.49 (d, 1H, J=5.9, H$_{Py,5}$), 6.96 (dd, 1H, 9.0, H$_{arom}$), 7.21 (d, 1H, H$_{arom}$), 7.57 (d, 2H, J=9.0, H$_{arom}$), 7.60 (d, 2H, J=8.9, H$_{arom}$), 7.81 (d, 1H, J=5.9, H$_{Py,6}$), 8.08 (t, 1H, H$_{arom}$), 8.80 (s, 1H, NH$_{urea}$), 8.89 (s, 1H, NH$_{urea}$), 11.63 (bs, 1H, NH$_{Py2}$). LC-MS: m/z 549 ([M]$^+$, 100).

Synthesis 11

3-Tert-butyl-1-(3-fluorophenyl)-1H-pyrazole-5-carboxylic acid

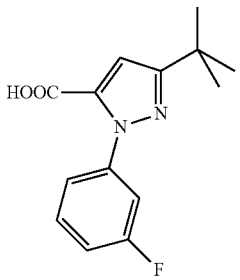 [SMILES: CC(C)(C)c1cc(C(=O)O)n(-c2cccc(F)c2)n1]

In a round-bottomed flask (dried in an oven) (3-fluorophenyl) boronic acid (224 mg, 1.6 mmol), ethyl-3-t-butyl-pyrazol-5-carboxylate (320 mg, 1.6 mmol), copper acetate (355 mg, 1.9 mmol) and dry pyridine (158 μL, 1.9 mmol) were suspended under vigorous stirring and an argon atmosphere in 10 mL dry DMF. To the reaction mixture, 300 mg of 4 A molecular sieve was added and the suspension stirred for 20 hours at room temperature. The suspension was diluted with 20 mL AcOEt, washed with water (2×20 mL), then with 20 mL conc. NaHCO$_3$ solution, and 20 mL brine, dried (MgSO$_4$) and evaporated under vacuum. A thick oil was obtained (520 mg) which was used in the next step without purification.

The oil was dissolved in 10 mL EtOH and 3 mL NaOH solution (2 M) was added under stirring and the reaction mixture was refluxed for 30 minutes. After cooling to room temperature, the reaction mixture was adjusted to pH 4 (with AcOH) and extracted with 20 mL AcOEt. The organic layer was washed with water (2×20 mL), dried and evaporated under vacuum. A solid was obtained (457 mg). The solid was purified on Biotage using cyclohexane:AcOEt 3:1 to afford the title compound as a white solid.

Yield: 166 mg (40%). $^1$H NMR (500 MHz, DMSO-d$_6$): δ 1.30 (s, 9H), 6.95 (s, 1H, H$_{pyr}$), 8.59 (d, 1H, J=8.6 Hz), 7.25-7.32 (m, 1H, H$_{arom}$), 7.35 (d, 1H, J=9.9 Hz, H$_{arom}$), 7.47-7.52 (m, 1H, H$_{arom}$), 13.22 (s, 1H, H$_{acid}$). HRMS: (M+H)$^+$ calcd for C$_{14}$H$_{15}$FN$_2$O$_2$, 262.1118, found: 262.1117.

Synthesis 12

1-(3-Tert-butyl-1-(3-fluorophenyl)-1H-pyrazol-5-yl)-3-(2-fluoro-4-(1-methyl-2-oxo-2,3-dihydro-1H-imidazo[4,5-b]pyridin-7-yloxy)phenyl)urea (AA-04)

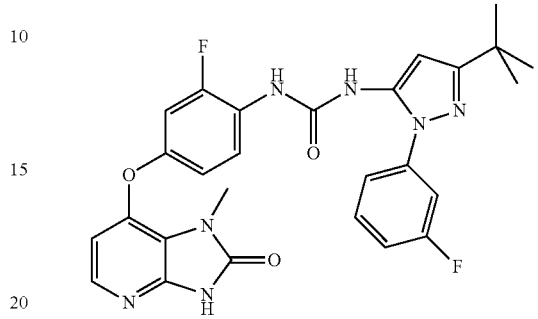

3-Tert-butyl-1-(3-fluorophenyl)-1H-pyrazole-5-carboxylic acid (393 mg, 1.5 mmol) was dissolved in dry DMF (8 mL), and triethylamine (209 μL, 1.5 mmol) was added. The solution was cooled at 0° C., and diphenylphosphoryl azide (323 μL, 1.5 mmol) was added. The reaction mixture was stirred for 30 minutes at 0° C., followed by 1 hour at room temperature. 7-(4-Amino-3-fluorophenoxy)-1-N-thyl-1H-imidazo[4,5-b]pyridin-2(3H)-one (8a) (140 mg, 0.5 mmol) was added, and the reaction mixture heated at 110° C. for 1 hour. The solution was cooled, diluted with AcOEt (100 mL) and extracted with water and brine. The organic layer was dried and evaporated, and the residue taken up in DCM. The remaining solid was recovered by filtration to afford the title compound.

Yield: 25 mg, 9%. $^1$H NMR, δ: 1.28 (s, 9H, tert-Bu), 3.41 (s, 3H, CH$_3$), 6.40 (s, 1H, H$_{Pyz,4}$)) 6.49 (d, 1H, J=6.1, H$_{Py,5}$), 6.96-7.02 (m, 1H, H$_{arom}$), 7.19-7.26 (m, 2H, H$_{arom}$), 7.36-7.44 (m, 2H, H$_{arom}$), 7.58 (t, 1H, H$_{arom}$), 7.81 (d, 1H, J=5.9, H$_{Py,6}$), 8.06 (t, 1H, J=9.1, H$_{arom}$), 8.83 (s, 1H, NH$_{urea}$), 8.92 (s, 1H, NH$_{urea}$), 11.64 (bs, 1H, NH$_{Py2}$). LC-MS: m/z 533 ([M]$^+$, 100).

Synthesis 13

Tert-butyl-4-(2-amino-3-nitropyridin-4-yl-oxy)naphthalen-1-yl-carbamate (3b)

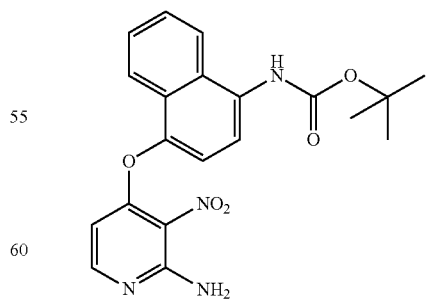

The title compound was prepared from tert-butyl 4-hydroxynaphthalen-1-ylcarbamate (Regan, J. et al, *J. Med. Chem.*, 2002, Vol. 45, No. 14, p. 2994) (3.9 g, 15 mmol) by the same method as described for compound (3a).

Yield: 5.4 g, 90%, upon recrystallization from dichloromethane. $^1$H-NMR (DMSO-d$_6$), δ (ppm), J (Hz): 1.52 (s, 9H, C(CH$_3$)$_3$), 5.80 (d, 1H, J=5.7, PyrH), 7.26 (s, 2H, NH$_2$), 7.38 (d, 1H, J=8.3, ArH, Naph), 7.58-7.69 (m, 3H, ArH, Naph), 7.86-7.89 (m, 1H, ArH, Naph), 7.93 (d, 1H, J=5.5, PyrH), 8.14-8.17 (m, 1H, ArH, Naph), 9.36 (s, 1H, NHBoc).

Synthesis 14

Tert-butyl-4-(2,3-diaminopyridin-4-yl-oxy)naphthalen-1-yl-carbamate (4b)

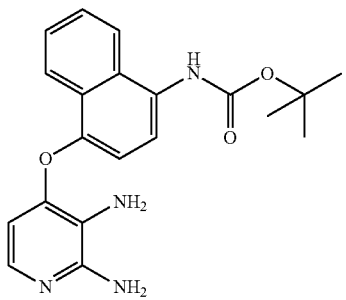 [SMILES: CC(C)(C)OC(=O)Nc1ccc(Oc2ccnc(N)c2[N+](=O)[O-])c2ccccc12]

The title compound was prepared from tert-butyl-4-(2-amino-3-nitropyridin-4-yl-oxy)naphthalen-1-yl-carbamate (3b) (0.50 g, 1.26 mmol) by the same method as described for compound (4a) as a brown solid.

Yield: 0.38 g (82%). $^1$H-NMR (DMSO-d$_6$), δ (ppm), J (Hz): 1.55 (s, 9H, C(CH$_3$)$_3$), 4.63 (s, 2H, NH$_2$), 5.66 (s, 2H, NH$_2$), 5.92 (d, 1H, J=5.6, PyrH), 7.05 (d, 1H, J=8.3, ArH, Naph), 7.24 (d, 1H, J=5.5, PyrH), 7.54 (d, 1H, J=8.3, ArH, Naph), 7.60-7.65 (m, 2H, ArH, Naph), 8.07-8.12 (m, 2H, ArH, Naph), 9.22 (s, 1H, NHBoc).

Synthesis 15

4-(4-N-Boc-aminonaphthalen-1-yl-oxy)-3-N-aminocarbamoylethyl-2-amino-pyridine (5b)

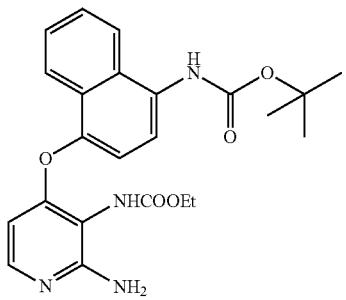

4-(4-N-Boc-aminonaphthalen-1-yl-oxy)-2,3-diaminopyridine (4b) (500 mg, 1.4 mmol) and the pyridine (222 μL, 2.7 mmol) were dissolved in dry THF (8 mL) under vigorous stirring at 0° C. To this solution the ethylchloroformate (136 mL, 1.5 mmol) was added at once. The reaction mixture was allowed to reach room temperature and was stirred for an additional 10 hours. The solvent was evaporated under vacuum and the residue partitioned between EtOAc and Na$_2$CO$_3$ solution. The organic layer was washed (20 mL brine), dried (MgSO$_4$) and evaporated to provide a solid residue. After purification by LC (Isolute column, Flash Si II, 50 g/170 mL; eluent: EtOAc), the desired compound was obtained.

Yield: 475 mg, 75%. $^1$H-NMR δ: 1.14-1.21 (m, 3H, CH$_3$), 1.50 (s, 9H, tBu), 4.04-4.10 (m, 2H, CH$_2$), 5.66 (d, 1H, J=5.7, H$_{Py}$), 5.84 (s, 2H, NH$_2$), 7.15 (d, 1H, J=8.1, H$_{arom}$), 7.49-7.60 (m, 3H, H$_{arom}$), 7.62 (d, 1H, J=5.7, H$_{Py}$), 7.98-8.04 (m, 1H, H$_{arom}$), 8.07 (d, 1H, J=8.5, H$_{arom}$), 8.40 (s, 1H, NH$_{carb}$), 9.22 (s, 1H, NH$_{Boc}$). LC-MS: m/z 440 [(M+H)$^+$, 100]. HRMS (EI): m/z calcd for C$_{23}$H$_{27}$N$_4$O$_5$ [(M+H)$^+$]: 439.1981; found 439.1979.

Synthesis 16

4-(4-Aminonaphthalen-1-yl-oxy)-3-N-aminocarbamoylethyl-2-amino-pyridine (6b)

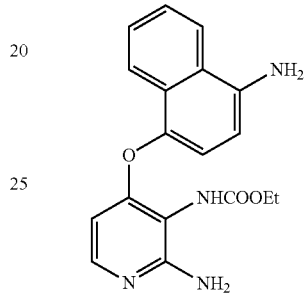

4-(4-N-Boc-aminonaphthalen-1-yl-oxy)-3-N-aminocarbamoylethyl-2-aminopyridine (5b) (475 mg, 1.05 mmol) was dissolved in dry TFA (10 mL) under vigorous stirring at 0° C. The solution was allowed to reach room temperature and was stirred for an additional 2 hours. The TFA was evaporated under vacuum and the oily residue partitioned between EtOAc and Na$_2$CO$_3$ solution. The organic layer was washed (20 mL brine), dried (MgSO$_4$) and evaporated to provide a solid residue.

Yield: 346 mg, 97%. $^1$H-NMR δ: 1.19-1.26 (m, 3H, CH$_3$), 4.07-4.13 (m, 2H, CH$_2$), 5.57 (d, 1H, J=5.7, H$_{Py}$), 5.77 (s, 4H, 2×NH$_2$), 6.66 (d, 1H, J=8.1, H$_{arom}$), 6.97 (d, 1H, J=8.1, H$_{arom}$), 7.37-7.45 (m, 2H, H$_{arom}$), 7.55 (d, 1H, J=5.7, H$_{Py}$), 7.76-7.86 (bs, 1H, H$_{arom}$), 8.09-8.12 (m, 1H, H$_{arom}$), 8.36 (s, 1H, NH$_{carb}$). LC-MS: m/z 339 [(M+H)$^+$, 100]. HRMS (EI): m/z calcd for C$_{18}$H$_{19}$N$_4$O$_3$ [(M+H)$^+$, 100]: 339.1457; found 339.1459.

Synthesis 17

4-(4-Aminonaphthalen-1-yl-oxy)-3-N-methyl-N-aminocarbamoylethyl-2-amino-pyridine (7b)

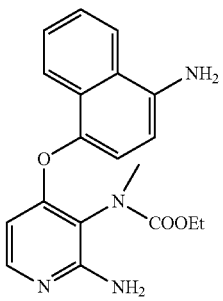 [SMILES: CCOC(=O)N(C)c1c(Oc2ccc(N)c3ccccc23)ccnc1N]

4-(4-Aminonaphthalen-1-yl-oxy)-3-N-aminocarbamoyl-ethyl-2-amino-pyridine (6b) (350 mg, 1.04 mmol) was dissolved in dry THF (8 mL) under vigorous stirring at 0° C. and argon. To this solution NaH (60% dispersed in mineral oil) (45 mg, 1.14 mmol) was added. After 40 minutes, MeI (66 mL, 0.91 mmol) was added at 0° C. The reaction mixture was allowed to reach room temperature and was stirred for further 10 hours. The solvent was evaporated under vacuum and the residue retaken in 20 mL of EtOAc. The solution was washed with brine (2×20 mL), dried and evaporated to dryness. The residue was triturated with $Et_2O$ and filtered to give the title compound as a solid.

Yield: 238 mg, 65%. $^1$H-NMR δ: 1.12-1.29 (m, 3H, $CH_3$), 3.14 (s, 3H, $CH_3$), 4.05-4.16 (m, 2H, $CH_2$), 5.53 (d, 1H, J=5.8, $H_{Py}$), 5.75 (s, 2H, $NH_2$), 6.01 (s, 2H, $NH_2$), 6.66 (d, 1H, J=8.1, $H_{arom}$), 6.96 (d, 1H, J=8.1, $H_{arom}$), 7.37-7.43 (m, 2H, $H_{arom}$), 7.57 (d, 1H, J=5.8, $H_{Py}$), 7.59-7.64 (m, 1H, $H_{arom}$), 8.11-8.15 (m, 1H, $H_{arom}$). LC-MS: m/z 353 ([M+H]$^+$, 100). HRMS (EI): m/z calcd for $C_{19}H_{21}N_4O_3$ ([M+H]$^+$): 353.1614; found 353.1610.

Synthesis 18

7-(4-Aminonaphthalen-1-yl-oxy)-1-N-methyl-1H-imidazo[4,5-b]pyridine-2(3H)-one (8b)

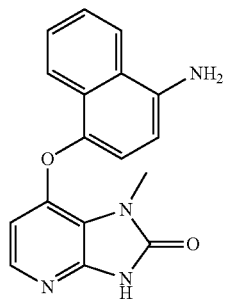 [SMILES: Cn1c(=O)[nH]c2nccc(Oc3ccc(N)c4ccccc34)c21]

230 mg (0.65 mmol) 4-(4-aminonaphthalen-1-yl-oxy)-3-N-methyl-N-aminocarbamoylethyl-2-aminopyridine (7b) were suspended in 5.0 mL solution 1.0 M of EtONa in EtOH. The suspension was submitted to microwave (150 W, 100° C.) for 45 minutes. After cooling, the reaction mixture was evaporated to dryness, retaken in 20 mL $H_2O$, the pH adjusted to 4.5 (AcOH), precipitating the title compound.

Yield: 167 mg, 84%. $^1$H-NMR δ: 3.61 (s, 3H, $CH_3$), 5.79 (s, 2H, $NH_2$), 6.10 (d, 1H, J=5.9, $H_{Py}$), 6.68 (d, 1H, J=8.1, $H_{arom}$), 7.10 (d, 1H, J=8.1, $H_{arom}$), 7.43-7.48 (m, 2H, $H_{arom}$), 7.64 (d, 1H, J=5.8, $H_{Py}$), 7.74-7.81 (m, 1H, $H_{arom}$), 8.12-8.17 (m, 1H, $H_{arom}$), 11.57 (s, 1H, $NH_{Py}$). LC-MS: m/z 307 ([M+H]$^+$, 100). HRMS (EI): m/z calcd for $C_{17}H_{25}N_4O_2$ ([M+H]$^+$): 307.1195; found 307.1188.

Synthesis 19

1-(3-Tert-butyl-1-phenyl-1H-pyrazol-5-yl)-3-(4-(1-methyl-2-oxo-2,3-dihydro-1H-imidazo[4,5-b]pyridin-7-yloxy)naphthalen-1-yl)urea (BB-01)

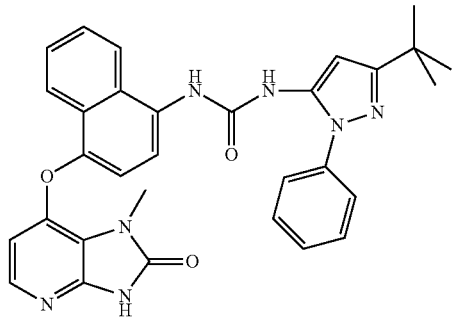 [SMILES: Cn1c(=O)[nH]c2nccc(Oc3ccc(NC(=O)Nc4cc(C(C)(C)C)nn4-c4ccccc4)c4ccccc34)c21]

The title compound was prepared from 3-tert-butyl-1-phenyl-1H-pyrazol-5-amine (0.18 mmol) and 7-(4-aminonaphthalen-1-yl-oxy)-1-N-methyl-1H-imidazo[4,5-b]pyridine-2(3H)-one (8b) (50 mg, 0.16 mmol) by the same method as described for (AA-01), as an off-white solid.

Yield: 87 mg, 98%. $^1$H NMR, δ 1.29 (s, 9H, tert-Bu), 3.53 (s, 3H, $CH_3$), 6.29 (d, 1H, J=5.9, $H_{Py,5}$), 6.40 (s, 1H, $H_{pyr}$), 7.24 (d, 1H, J=8.3, $H_{arom}$), 7.43 (t, 1H, J=7.0 Hz), 7.54-7.63 (m, 5H), 7.66 (t, 1H, J=8.2, $H_{arom}$), 7.74 (d, 1H, J=5.9, $H_{Py,6}$), 7.86 (d, 2H, J=8.3, $H_{arom}$), 8.05-8.10 (m, 1H), 8.77 (s, 1H, $NH_{urea}$), 9.07 (s, 1H, $NH_{urea}$), 11.64 (s, 1H, $NH_{Py2}$). LC-MS: $R_1$=8.25 min; m/z 548.2 (M$^+$, 100). HRMS (EI): m/z calcd for $C_{31}H_{30}N_7O_3$ ([M+H]$^+$): 548.2410; found: 548.2404.

Synthesis 20

1-(1-N-p-tolyl-3-tert-butyl-pyrazol-5-yl)-3-(4-(2-oxo-2,3-dihydro-1-N-methyl-1H-imidazo[4,5-b]pyridin-7-yl-oxy)naphthalen-1-yl)urea (BB-02)

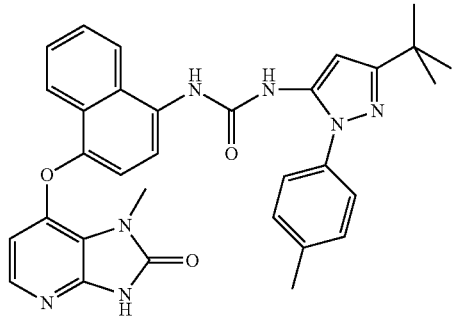 [SMILES: Cc1ccc(-n2nc(C(C)(C)C)cc2NC(=O)Nc2ccc(Oc3ccnc4[nH]c(=O)n(C)c34)c3ccccc23)cc1]

The title compound was prepared from 3-tert-butyl-1-p-tolyl-1H-pyrazol-5-amine (35 mg, 0.15 mmol) and 7-(4-aminonaphthalen-1-yl-oxy)-1-N-methyl-1H-imidazo[4,5-b]pyridin-2(3H)-one (8b) (40 mg, 0.13 mmol) by the same method as described for (AA-01), as an off-white solid.

Yield: 52 mg, 71%. $^1$H NMR, δ: 1.28 (s, 9H, tert-Bu), 2.40 (s, 3H, $CH_3$), 3.53 (s, 3H, $CH_3$), 6.29 (d, 1H, J=5.9, $H_{Py,5}$), 6.39 (s, 1H, $H_{pyr}$), 7.24 (d, 1H, J=8.4, $H_{arom}$), 7.36 (d, 2H, J=8.2, $H_{arom}$), 7.45 (d, 2H, J=8.2, $H_{arom}$), 7.60 (t, 1H, J=7.5, H$_{arom}$), 7.67 (t, 1H, J=7.6, H$_{arom}$), 7.74 (d, 1H, J=5.9, H$_{Py,6}$), 7.87 (d, 1H, J=8.3, H$_{arom}$), 8.07 (d, 2H, J=8.3, H$_{arom}$), 8.71 (s, 1H, NH$_{urea}$), 9.06 (s, 1H, NH$_{urea}$), 11.65 (s, 1H, NH$_{Py3}$). LC-MS: R$_f$=5.23 min; m/z 562.2 ([M+H]$^+$, 100). HRMS (EI): m/z calcd for C$_{32}$H$_{32}$N$_7$O$_3$ ([M+H]$^+$): 562.2561; found: 562.2566.

(Reference) Synthesis 21

Tert-butyl 2-fluoro-4-(2-(methylamino)-3-nitropyridin-4-yloxy)phenylcarbamate

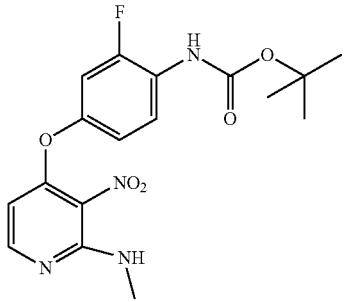

Tert-butyl 2-fluoro-4-hydroxyphenylcarbamate (3.25 g, 14.4 mmol) was dissolved in DMSO (25 mL) and the solution was stirred under an argon atmosphere for 20 minutes. Sodium hydride (60% in mineral oil, 580 mg, 14.4 mmol) was added portionwise and the dark solution was stirred at room temperature for 1 hour. 4-chloro-N-methyl-3-nitropyridin-2-amine (2.7 g, 14.4 mmol) dissolved in DMSO (5 mL) was added at once and the red solution was stirred at 50° C. for 2 hours. The solution was cooled, poured onto crushed ice (200 g) and extracted with ethyl acetate (3×100 mL). The organic phases were washed with brine, dried and evaporated to give the title compound as a yellow solid.

Yield: 5.3 g, 90%. $^1$H NMR (500 MHz, DMSO-d$_6$) δ: 1.47 (s, 9H, tert-Bu) 2.93 (d, J=4.5 Hz, CH$_3$N), 6.08 (d, J=5.7 Hz, 1H, H$_{py}$), 7.00 (m, 1H, H$_{arom}$), 7.22 (m, 1H, H$_{arom}$), 7.55 (q, J=4.5 Hz, 1H, NHCH$_3$), 7.66 (m, 1H, H$_{arom}$), 8.14 (d, J=5.7 Hz, 1H, 1H, H$_{py}$), 9.04 (bs, 1H, NH). LC-MS: m/z 378.3 ([M+H]$^+$, 100).

(Reference) Synthesis 22

Tert-butyl 4-(3-amino-2-(methylamino)pyridin-4-yloxy)-2-fluorophenylcarbamate

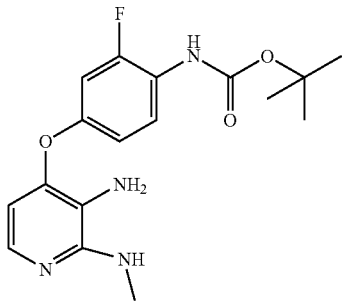 [SMILES: CNc1nccc(Oc2ccc(NC(=O)OC(C)(C)C)c(F)c2)c1[N+](=O)[O-]]

Tert-butyl 2-fluoro-4-(2-(methylamino)-3-nitropyridin-4-yloxy)phenylcarbamate (5.3 mg, 14 mmol) was dissolved in absolute ethanol (600 mL) and hydrogenated on a 10% Pd/C cartridge through an H-Cube apparatus, to give the title compound as a yellow solid.

Yield: 4.88 g (quantitative yield). $^1$H NMR (500 MHz, DMSO-d$_6$) δ: 1.44 (s, 9H, tert-Bu), 2.85(d, 3H, J=4.5 Hz, CH$_3$N), 4.51 (bs, 2H, NH$_2$), 5.94 (m, 1H, CH$_3$NH), 6.10 (d, 1H, J=5.6 Hz, H$_{py}$), 6.72 (m, 1H, H$_{arom}$), 6.85 (m, 1H, H$_{arom}$), 7.37 (d, 1H, J=5.6 Hz, H$_{py}$), 7.44 (m, 1H, H$_{arom}$), 8.87 (bs, 1H, NH). LC-MS: m/z 348.4 ([M+H]$^+$, 100).

(Reference) Synthesis 23

Tert-butyl 2-fluoro-4-(3-methyl-2-oxo-2,3-dihydro-1H-imidazo[4,5-b]pyridin-7-yloxy)phenylcarbamate

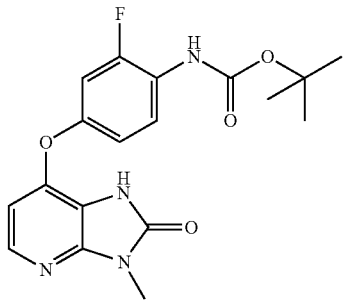 [SMILES: Cn1c(=O)[nH]c2c(Oc3ccc(NC(=O)OC(C)(C)C)c(F)c3)ccnc21]

To an ice-cooled solution of tert-butyl 4-(3-amino-2-(methylamino)pyridin-4-yloxy)-2-fluorophenylcarbamate (4.9 g, 14 mmol) in THF (150 mL) and pyridine (10 mL) under an argon atmosphere, a solution of triphosgene (4.45 g, 15 mmol) in THF (75 mL) was added over 2 hours via a dropping funnel. The solution was stirred for 2 hours at 0° C., followed by 4 hours at room temperature, and then refluxed overnight. After cooling, the solution was filtered, evaporated and chromatographed on a Biotage apparatus (25+M column, eluent DCM/EtOAc 1/1) to give the title compound as a white solid.

Yield: 2.05 g, 40%. $^1$H NMR (500 MHz, DMSO-d$_6$) δ: 1.47 (s, 9H, tert-Bu), 3.32 (s, 3H, CH$_3$N), 6.53 (d, 1H, J=5.9 Hz, H$_{py}$), 6.94 (m, 1H, H$_{arom}$), 7.15 (m, 1H, H$_{arom}$), 7.60 (m, 1H, H$_{arom}$), 7.89 (d, 1H, J=5.9 Hz, H$_{py}$), 8.97 (s, 1H, NH), 11.46 (s, 1H, NH). LC-MS: m/z 375.1 ([M+H]$^+$, 100).

(Reference) Synthesis 24

7-(4-Amino-3-fluorophenoxy)-3-methyl-1H-imidazo[4,5-b]pyridin-2(3H)-one

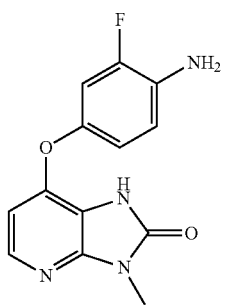 [SMILES: Cn1c(=O)[nH]c2c(Oc3ccc(N)c(F)c3)ccnc21]

A solution of tert-butyl 2-fluoro-4-(3-methyl-2-oxo-2,3-dihydro-1H-imidazo[4,5-b]pyridin-7-yloxy)phenylcarbamate (2.18 g, 5.8 mmol) in 1 M TBAF in THF (41 mL) was refluxed overnight under an argon atmosphere. The solution was cooled and evaporated and water (20 mL) was added, upon which a precipitate formed. The precipitate was filtered, washed with water, and dried to give the title compound as an off-white solid.

Yield: 1.37 g, 86%. $^1$H NMR (500 MHz, DMSO-d$_6$): δ 3.29 (s, 3H, CH$_3$N), 5.17 (s, 2H, NH$_2$), 6.35 (d, 1H, J=5.94 Hz, H$_{py}$), 6.74-6.83 (m, 2H, H$_{arom}$), 6.99 (m, 1H, H$_{arom}$), 7.81 (d, 1H, J=5.94 Hz, H$_{py}$), 11.44 (s, 1H, NH). LC-MS: m/z 275.1 ([M+H]$^+$, 100).

(Reference) Synthesis 25

7-(4-amino-3-fluorophenoxy)-1,3-dimethyl-1H-imidazo[4,5-b]pyridin-2(3H)-one

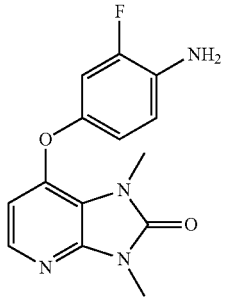 [SMILES: Cn1c(=O)n(C)c2c(Oc3ccc(N)c(F)c3)ccnc21]

To a solution of 7-(4-amino-3-fluorophenoxy)-3-methyl-1H-imidazo[4,5-b]pyridin-2(3H)-one (100 mg, 0.365 mmol) in THF (4 mL) at 0° C. under argon, NaH (16.77 mg, 0.419 mmol) was added in one portion. The resulting solution was stirred for 20 minutes and iodomethane (0.025 mL, 0.401 mmol) was added. After 1 hour, water was added, and the solution evaporated and extracted with DCM (3×20 mL) to give the title compound.

Yield: 80 mg, 0.278 mmol, 76%. $^1$H NMR (CDCl$_3$), δ: 3.51 (s, 3H, Me), 3.66 (s, 3H, Me), 6.40 (d, 1H, J=6.0, H$_{arom,Py}$), 6.74 (ddd, 1H, J=8.6, 2.5, 1.0, H$_{arom,Py}$), 6.83 (m, 2H, H$_{arom,FPh}$), 7.87 (d, 1H, J=6.0, H$_{arom,Py}$). LC-MS: Rf=2.60 min; m/z 289.1 ([M+H]$^+$, 90).

(Reference) Synthesis 26

1-(1-N-p-tolyl-3-tert-butyl-pyrazol-5-yl)-3-(4-(2-oxo-2,3-dihydro-1-N-methyl-1H-imidazo[4,5-b]pyridin-7-yl-oxy)phenyl)urea (XX-02)

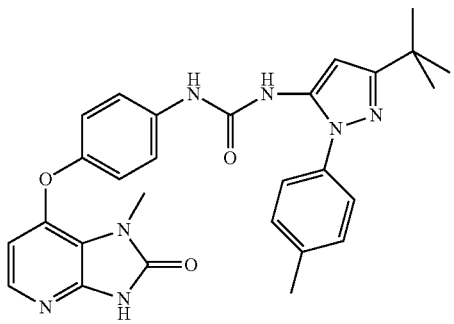

The title compound was prepared using 3-tert-butyl-1-p-tolyl-1H-pyrazol-5-amine (43.7 mg, 0.19 mmol) and 7-(4-aminophenyloxy)-1-N-methyl-1H-imidazo[4,5-b]pyridin-2(3H)-one (Niculescu-Duvaz, D. et al, *J. Med. Chem.*, 2009, Vol. 52, No. 8, p. 2255) (40 mg, 0.16 mmol) by the same method as described for (AA-01), as a white solid.

Yield: 62 mg, 76%. $^1$H NMR, δ: 1.27 (s, 9H, tert-Bu), 2.37 (s, 3H, CH$_3$), 3.44 (s, 3H, CH$_3$), 6.35 (d, 1H, J=5.9, H$_{Py,5}$), 6.39 (s, 1H, H$_{pyr}$), 7.11 (d, 2H, J=9.0, H$_{arom}$), 7.33 (d, 2H, J=8.3, H$_{arom}$), 7.39 (d, 2H, J=8.3, H$_{arom}$), 7.47 (d, 2H, J=9.0, H$_{arom}$), 7.78 (d, 1H, J=5.9, H$_{Py,6}$), 8.32 (s, 1H, NH$_{urea}$), 9.08 (s, 1H, NH$_{urea}$), 11.59 (s, 1H, NH$_{Py3}$). LC-MS: R$_f$=5.14 min; m/z 511 ([M+H]$^+$, 100). HRMS (EI): m/z calcd for C$_{28}$H$_{30}$N$_7$O$_3$ ([M+H]$^+$): 512.2405; found: 512.2405.

(Reference) Synthesis 27

1-(3-Tert-butyl-1-phenyl-1H-pyrazol-5-yl)-3-(4-(1,3-dimethyl-2-oxo-2,3-dihydro-1H-imidazo[4,5-b]pyridin-7-yloxy)-2-fluorophenyl)urea (XX-03)

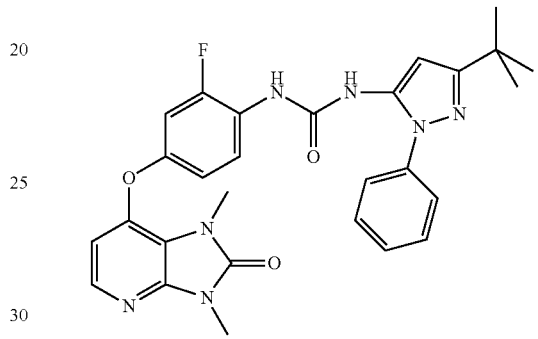

The title compound was prepared from 3-tert-butyl-1-phenyl-1H-pyrazol-5-amine (130 mg, 0.60 mmol) and 7-(4-amino-3-fluorophenoxy)-1,3-dimethyl-1H-imidazo[4,5-b]pyridin-2(3H)-one (100 mg, 0.35 mmol) by the same method as described for (AA-01), as a yellow powder.

Yield: 15 mg, 8%. $^1$H NMR (CDCl$_3$), δ: 1.39 (s, 9H, tert-Bu), 3.48 (s, 3H, Me), 3.59 (s, 3H, Me), 6.47 (d, 1H, J=5.9, H$_{arom,Py}$), 6.49 (s, 1H, H$_{Pyz,4}$), 6.85 (dd, 1H, J=11.1, 2.5, H$_{arom,FPh}$), 6.89 (d, 1H, J=9.0, H$_{arom,FPh}$), 7.31 (t, 1H, J=7.7, H$_{arom,Ph}$), 7.42 (t, 2H, J=7.7, H$_{arom,Ph}$), 7.50 (d, 2H, J=7.9, H$_{arom,Ph}$), 7.92 (d, 1H, J=5.9, H$_{arom,Py}$), 8.15 (t, 1H, J=8.9, H$_{arom,FPh}$). LC-MS: Rf=2.78 min; m/z 530 ([M+H]$^+$, 90). HRMS (EI): m/z calcd for C$_{28}$H$_{29}$FN$_7$O$_3$ ([M+H]$^+$): 530.2310; found: 530.2326.

(Reference) Synthesis 28

1-(5-Tert-butyl-2-phenyl-2H-pyrazol-3-yl)-3-[4-(2-oxo-2,3-dihydro-1H-imidazo[4,5-b]pyridin-7-yloxy)-phenyl]urea (XX-01)

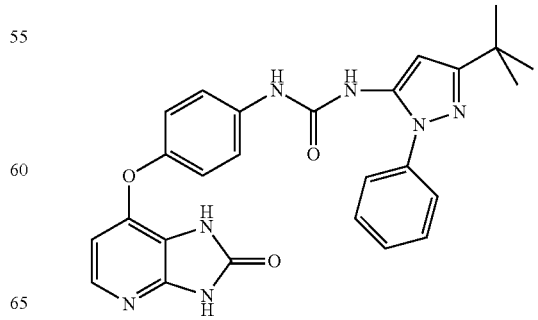

The title compound was obtained using known methods, as shown, for example, in Synthesis 61 in Niculescu-Duvaz et al., 2006.

(Reference) Synthesis 29

1-[5-tert-Butyl-2-(4-fluoro-phenyl)-2H-pyrazol-3-yl]-3-[4-(2-oxo-2,3-dihydro-1H-imidazo[4,5-b]pyridin-7-yloxy)-phenyl]urea (XX-04)

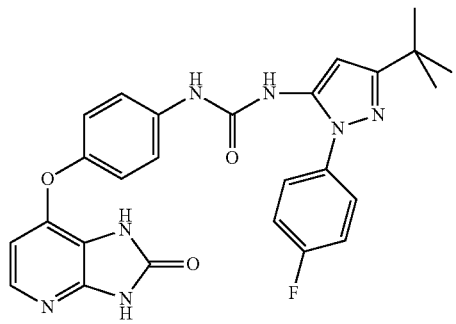

The title compound was obtained using known methods, as shown, for example, in Synthesis 79 in Niculescu-Duvaz et al., 2006.

Biological Methods
Biological Methods—Assay A—DELFIA Kinase Assay

Compounds were assessed by a kinase assay performed according to the following protocol.

The following reagents were prepared:
DELFIA Kinase Buffer (DKB):

TABLE 2

| Reagent | Stock Concentration | Volume per mL (µL) | Volume per 10 mL plate (µL) |
|---|---|---|---|
| 20 mM MOPS pH 7.2 | 0.2M | 100 | 1000 |
| 0.5M EGTA pH 8.0 | 0.5M | 10 | 100 |
| 10 mM MgCl₂ | 1M | 10 | 100 |
| 0.1% β-mercaptoethanol | — | 1 | 10 |
| 25 mM β-glycerophosphate | 0.5M | 50 | 500 |
| Water | 100% | 829 | 8290 |

MOPS=3-[N-Morpholino]propanesulfonic acid (Sigma M3183).

EGTA=Ethylene glycol-bis(2-aminoethylether)-N,N,N',N'-tetraacetic acid (Sigma E3889).

DKB1 (DKB with B-RAF and MEK Protein):

Combine 4950 µL of DKB and 50 µL of 2.5 mg/mL GST-MEK stock (to give 1 mg of MEK per 40 µL). Then add 22.5 µL of B-RAF to give ~0.2 µL of B-RAF per 40 µL.

DKB2 (DKB with MEK Protein):

Combine 4950 µL of DKB and 50 µL of 2.5 mg/mL GST-MEK stock (to give 1 mg of MEK per 40 µL). Use 500 µL of this for the blow out (BO) and the empty vector (EV) control.

ATP:

100 mM stock, dilute to 500 µM to give 100 µM final concentration in assay.

Inhibitors (Test Compounds):

100 mM stock, dilute to 10, 3, 1, 0.3, 0.1, 0.03, 0.01, 0.003, 0.001, 0.0003, and 0.0001 mM in DMSO in drug plate, resulting in concentration of 100, 30, 10, 3, 1, 0.3, 0.1, 0.03, 0.01, 0.003, and 0.001 µM in the assay.

Primary Antibody:

Phospho-MEK1/2 CST #9121S diluted 1:1000 in DELFIA assay buffer (AB).

Pre-incubate antibody in the AB for 30 minutes at room temperature prior to use.

Secondary Antibody:

Anti-rabbit-Eur labelled secondary Perkin Elmer #AD0105 diluted 1:1000 in DELFIA assay buffer (AB). Pre-incubate antibody in the AB for 30 minutes at room temperature prior to use. (Primary and secondary antibodies were incubated together.)

Tween:

0.1% Tween 20 in water.

Assay Buffer:

DELFIA assay buffer Perkin Elmer #4002-0010.

Enhancement Solution:

DELFIA enhancement solution Perkin Elmer #4001-0010.

Assay Plates:

96 well glutathione-coated black plate Perbio #15340.

Procedure:

1. Preblock wells with 5% milk in TBS for 1 hour.
2. Wash wells 3× with 200 µL TBS.
3. Plate out 40 µL of DKB1 for all inhibitors (test compounds), DMSO control, and optionally other control compounds.
4. Plate out 40 µL of DKB2 for BO and EV wells.
5. Add inhibitors (test compounds) at 0.5 µL per well according to desired plate layout.
6. Add 0.5 µL DMSO to vehicle control wells.
7. Add 2 µL of B-RAF to BO and EV wells.
8. Pre-incubate with inhibitors (test compounds) for 10 minutes at room temperature with shaking.
9. Add 10 µL of 500 µM ATP stock, in DKB, to give 100 µM assay concentration.
10. Seal plates with TopSeal and incubate at room temperature with shaking for 45 minutes.
11. Wash plates 3× with 200 µL 0.1% Tween20/Water to terminate reaction.
12. Add 50 µL per well of antibody mix and incubate for 1 hour at room temperature with shaking.
13. Wash plates 3× with 200 µL 0.1% Tween20/Water.
14. Add 100 µL DELFIA enhancement solution per well, cover in foil, and incubate at room temperature for 30 minutes with shaking.
15. Read on Victor using Europium protocol.

Values for the blank (Empty Vector) are subtracted from all values. The DMSO controls are set as 100% activity and assay points (the response) are calculated as a percentage of the DMSO control. Data are plotted using Graphpad Prism software and a non-linear regression line is calculated using a variable slope sigmoidal dose-response equation:

$$Y = \text{Bottom} + [\text{Top} - \text{Bottom}]/[1 + 10^{((\log EC_{50} - X) * \text{HillSlope})}]$$

where X is the logarithm of concentration and Y is the response. The IC50 generated by this procedure is the concentration of the drug that produces a percentage control fluorescence value midway between the saturation, and zero-effect plateaus. Three independent assays are usually performed and the mean IC50 is reported.

Biological Methods—Assay B—Cell Based Phosho-ERK Assay

Compounds were assessed using a cell-based assay which was performed according to the following protocol.

Day 0:
  Plate out 16,000 mutant BRAF WM266.4 cells/well in 99 μL medium in a 96-well plate.
Day 1:
  1. Add 1 μL inhibitor (test compound) to the cells (total 1 μL solution).
  2. Incubate the cells with test compound for 6 hours at 37° C.
  3. Aspirate off the solution from all of the wells.
  4. Fixate the cells with 100 μL 4% formaldehyde/0.25% Triton X-100 PBS per well.
  5. Incubate the plate for 1 hour at 4° C.
  6. Aspirate off the fixing solution and add 300 μL TBS per well.
  7. Leave the plate overnight at 4° C.
Day 2:
  1. Wash the plate 2× with 200 μL PBS per well.
  2. Block with 100 μL 5% dried milk in TBS.
  3. Incubate the plate for 20 minutes at 37° C.
  4. Wash the plate 2× with 0.1% tween/$H_2O$.
  5. Add 50 μL of 3 μg/mL primary antibody pERK (Sigma M8159), diluted in 5% milk powder/TBS, to each well.
  6. Incubate the plate for 2 hours at 37° C.
  7. Wash the plate 3× with 0.1% tween/$H_2O$.
  8. Add 50 μL of 0.45 μg/mL secondary Europium-labelled anti-mouse antibody (Perkin Elmer) to each well.
  9. Incubate the plate for 1 hour at 37° C.
  10. Wash the plate 3× with 0.1% tween/$H_2O$.
  11. Add 100 μL enhancement solution (Perkin Elmer) to each well.
  12. Leave the plate for approximately 10 minutes at room temperature before gently shaking the plate.
  13. Read Europium Time Resolved Fluorescence in Victor2.
  14. Wash the plate 2× with 0.1% tween/$H_2O$.
  15. Measure the protein concentration with BCA (Sigma) by adding 200 μL of solution per well.
  16. Incubate the plate for 30 minutes at 37° C.
  17. Read absorbance levels at 570 nm in a plate reader.

Note that Europium counts are normalised for protein levels by dividing counts by absorbance.

Values for the blank (no cells) are subtracted from all values. The DMSO controls are set as 100% activity and assay points (the response) are calculated as a percentage of the DMSO control. Data are plotted using Graphpad Prism software and a non-linear regression line is calculated using a variable slope sigmoidal dose-response equation:

$$Y = Bottom + [Top - Bottom]/[1 + 10^{((Log\ EC50 - X) * HillSlope)}]$$

where X is the logarithm of concentration and Y is the response). The IC50 generated by this procedure is the concentration of the drug that produces a percentage control fluorescence value midway between the saturation, and zero-effect plateaus. Three independent assays are usually performed and the mean IC50 is reported.

Biological Methods—Assay C—SRB Cell Proliferation Assay (SRB $GI_{50}$)

Cell lines (e.g., WM266.4 and A375M melanoma cell lines; SW620 colorectal carcinoma cell line) are routinely cultured in DMEM or RPMI1640 supplemented with 10% foetal bovine serum, at 37° C., in 10% $CO_2$ water saturated atmosphere. Cultures are maintained in exponential growth phase by sub-culturing before having become confluent (3-5 day intervals). Single cell suspensions are prepared by harvesting an 80 $cm^2$ tissue culture flask with 5 mL commercial trypsin EDTA. After 5 minutes, the detached cells are mixed with 5 mL fully complemented culture medium and centrifugally pelleted (1000 rpm for 7 minutes). After aspirating the supernatant, the cell pellet is re-suspended in 10 mL fresh medium and the cells fully disaggregated by drawing the whole volume up/down 5 times through a 19-gauge needle. The concentration of the cells is determined using a haemocytometer (1/10 dilution). A suitable volume to give at least a 2-fold excess for the number of tests being conducted, typically 100-200 mL, is prepared by diluting the cell suspension to 10,000-40,000/mL, and 100 μL/well dispensed into 96 well plates using a programmable 8-channel peristaltic pump, giving 1000-4000 cells/well, leaving column 12 blank. The plates are returned to the incubator for 24 hours to allow the cells to re-attach.

The compounds being tested are prepared at 10 mM in DMSO. Aliquots (24 μL are diluted into 1.2 mL culture medium giving 200 μM, and 10 serial dilutions of 3× performed by transferring 80 μL to 160 μL. Aliquots (100 μL) of each dilution are added to the wells, using an 8-channel pipettor, thus performing a final further 2× dilution, and giving doses ranging from 100 μM to 0.005 μM. Column 11 receives plain culture medium only. Each compound is tested in quadruplicate, each replicate being the average of four wells.

After a further 5 days growth, the plates are emptied, and the cells are fixed in 10% trichloroacetic acid for 30 minutes at 4° C. After thorough rinsing in running tap water, the plates are dried, and stained by adding 50 μL of a solution of 0.1% sulphorhodamine-B in 1% acetic acid, for 10 minutes at room temperature. The stain is poured out and the plates thoroughly rinsed under a stream of 1% acetic acid, thus removing unbound stain, and dried. The bound stain is taken into solution by addition of 100 μL Tris buffer pH 8, followed by 10 minutes on a plate-shaker (approximately 500 rpm). The absorbance at 540 nm in each well (being proportional to the number of cells present) is determined using a plate reader.

After averaging the blank values in column 12 this was subtracted from all values, and results expressed as a percentage of the untreated value (column 11). The 10 values so derived (in quadruplicate) are plotted against the logarithm of the drug concentration, and analysed by non-linear regression to a four parameter logistic equation, setting constraints if suggested by inspection. The $GI_{50}$ generated by this procedure is the concentration of the drug that produces a percentage control $A_{540}$ midway between the saturation, and zero-effect plateaus.

Biological Methods—Xenograft Studies

SW620 human colorectal carcinoma cells (mutant RAS, $7 \times 10^7$) or A375M human melanoma cells (mutant BRAF, $10^7$) were inoculated sub-cutaneuously in suspension (0.2 mL) into the right flank of female Crl:CD1-Foxn1nu athymic mice. Groups were assigned to treatment following stratified allocation of tumour volumes. Treatment with test compound began between days 11-14 post-cell administration. For gavage, a suspension (DMSO:water, 1:19, v/v at 10 mL/kg) was administered. Control animals received a similar dosage of vehicle (DMSO:water, 1:19, v/v). Treatment with test compound was continued once daily for 24 doses.

Biological Data—Assay Data

Data for several compounds of the present invention, as well as several comparison compounds are summarised in the following table. Lower $IC_{50}/GI_{50}$ values indicate higher potency.

TABLE 3

| Code | Assay A BRAF IC$_{50}$ (μM) | Assay B pERK WM266.4 IC$_{50}$ (μM) | Assay C SRB WM266.4 GI$_{50}$ (μM) | Assay C SRB A375M GI$_{50}$ (μM) | Assay C SRB SW620 GI$_{50}$ (μM) |
|---|---|---|---|---|---|
| AA-01 | 0.27  | 0.26  | 0.052 | 0.138 | 0.167 |
| AA-02 | 0.197 | 0.020 | 0.057 |       |       |
| AA-03 | 0.302 | 0.060 | 0.121 |       |       |
| BB-01 | 0.25  | 0.019 | 0.008 | 0.052 | 1.6   |
| BB-02 | 2.28  | 0.026 | 0.016 | 0.101 | 1.685 |
| XX-01 | 0.094 | 0.62  | 0.39  | 1.13  | 0.84  |
| XX-02 | 0.20  | 0.09  | 0.066 | 0.25  | 0.45  |
| XX-03 | 1.09  | 0.12  | 0.033 | 0.247 | 6.83  |
| XX-04 | 0.24  | 0.20  | 0.020 | 0.307 | 2.72  |

In the in vitro BRAF enzyme assay (Assay A), the compounds of the present invention (~0.2-2.3 μM) and the comparison compounds (~0.1-1.1 μM) had similar BRAF IC$_{50}$ values.

In the in vitro pERK cell-based assay (Assay B), the compounds of the present invention (~0.02-0.26 μM) and the comparison compounds (~0.1-0.6 μM) had similar pERK IC$_{50}$ values.

In the in vitro SRB cell-based Assay (Assay C), for the mutant BRAF cell lines WM266.4 and A375M, the compounds of the present invention (WM266.4: ~0.01-0.12 μM; A375M: ~0.05-0.14 μM) and the comparison compounds (WM266.4: ~0.02-0.4 μM; A375M: ~0.25-1.1 μM) had similar GI50 values. Notably, BB-01 was the most potent (with the lowest GI$_{50}$: WM266.4, 0.008 μM; A375M, 0.052 μM), and XX-01 was the least potent (with the highest GI$_{50}$: WM266.4, 0.39 μM; A375M, 1.13 μM).

In the in vitro SRB cell-based Assay (Assay C), for the mutant RAS cell line SW620, the compounds of the present invention (SW620: ~0.17-1.6 μM) and the comparison compounds (SW620: ~0.45-7 μM) had similar GI50 values.

However, note that, based on the in vitro mutant RAS data, it would be expected that XX-01 and XX-02 would have better therapeutic efficacy than BB-02, in the in vivo mutant RAS SW620 xenograft study.

Similarly, based on the in vitro mutant RAS data, it would be expected that XX-02 would have a similar therapeutic efficacy as AA-01, in the in vivo mutant RAS SW620 xenograft study.

Based on the in vitro mutant RAS data, it would not be expected that the claimed compounds (especially AA-01 and BB-02) are substantially more effective than the comparison compounds (XX-01, XX-02, XX-03, XX-04), in the in vivo mutant RAS SW620 xenograft study.

Biological Data—BRAF/RAS/Wild Type Selectivity Data

Data for several compounds of the present invention, as well as several comparison compounds are illustrated in FIGS. 4 to 10, as discussed below. The data illustrate the selectivity, or lack of selectivity, for mutant BRAF or mutant RAS cell lines.

FIG. 4 is a bar graph showing the ratio of the GI$_{50}$ for each of a range of cell lines to the GI$_{50}$ for the WM266.4 cell line for compound AA-01. The range of cell lines are (a) a panel of mutant BRAF (mutBRAF) cell lines: WM266.4, A375M, UACC62; (b) a panel of mutant RAS (mutRAS) cell lines: SW620, HCT116, and WM1361; and (c) a panel of wild type BRAF and RAS (wtBRAFT/RAS) cell lines: SKMEL23, KM12, and BT474.

FIG. 5 is a bar graph showing the ratio of the GI$_{50}$ for each of a range of cell lines to the GI$_{50}$ for the WM266.4 cell line for compound BB-01. The ranges of cell lines are as for FIG. 4.

FIG. 6 is a bar graph showing the ratio of the GI$_{50}$ for each of a range of cell lines to the GI$_{50}$ for the WM266.4 cell line for compound BB-02. The ranges of cell lines are as for FIG. 4.

FIG. 7 is a bar graph showing the ratio of the GI$_{50}$ for each of a range of cell lines to the GI$_{50}$ for the WM266.4 cell line for comparison compound XX-01. The ranges of cell lines are as for FIG. 4.

FIG. 8 is a bar graph showing the ratio of the GI$_{50}$ for each of a range of cell lines to the GI$_{50}$ for the WM266.4 cell line for comparison compound XX-02. The ranges of cell lines are as for FIG. 4.

FIG. 9 is a bar graph showing the ratio of the GI$_{50}$ for each of a range of cell lines to the GI$_{50}$ for the WM266.4 cell line for comparison compound XX-03. The ranges of cell lines are as for FIG. 4.

FIG. 10 is a bar graph showing the ratio of the GI$_{50}$ for each of a range of cell lines to the GI$_{50}$ for the WM266.4 cell line for comparison compound XX-04. The ranges of cell lines are as for FIG. 4.

Based on these in vitro data, it would not be expected that the claimed compounds (especially AA-01 and BB-02) are substantially more effective than the comparison compounds (XX-01, XX-02, XX-03, XX-04), in the in vivo mutant RAS SW620 xenograft study.

Biological Data—Xenograft Data

Xenograft data for several compounds of the present invention, as well as several comparison compounds are illustrated in FIGS. 11-19.

FIG. 11 is a graph of relative tumour volume as a function of time (days) for mouse xenografts of the mutant RAS cell line SW620, for treatment with compound AA-01 and for controls.

The data demonstrate that compound AA-01 substantially reduced tumour volume over the timescale of the study (e.g., a factor of about 3), as compared to the control, for this mutant RAS colorectal carcinoma cell line.

FIG. 12 is a graph of relative tumour volume as a function of time (days) for mouse xenografts of the mutant RAS cell line SW620, for treatment with compound BB-02 and for controls.

The data demonstrate that compound BB-02 substantially reduced tumour volume over the timescale of the study (e.g., a factor of about 1.5), as compared to the control, for this mutant RAS colorectal carcinoma cell line.

FIG. 13 is a graph of relative tumour volume as a function of time (days) for mouse xenografts of the mutant BRAF cell line A375, for treatment with compound AA-01 and for controls.

The data demonstrate that compound AA-01 substantially reduced tumour volume over the timescale of the study (e.g., a factor of about 2.5), as compared to the control, for this melanoma cell line.

FIG. 14 is a graph of relative tumour volume as a function of time (days) for mouse xenografts of the mutant BRAF cell line A375, for treatment with compound BB-02 and for controls.

The data demonstrate that compound BB-02 substantially reduced tumour volume over the timescale of the study (e.g., a factor of about 1.5), as compared to the control, for this mutant BRAF melanoma cell line.

FIG. 15 is a graph of relative tumour volume as a function of time (days) for mouse xenografts of the mutant RAS cell line SW620, for treatment with comparison compound XX-01 and for controls.

The data demonstrate that comparison compound XX-01 had relatively little effect, as compared to the control, for this mutant RAS colorectal carcinoma cell line.

FIG. 16 is a graph of relative tumour volume as a function of time (days) for mouse xenografts of the mutant RAS cell line SW620, for treatment with comparison compound XX-02 and for controls.

The data demonstrate that comparison compound XX-02 had relatively little effect, as compared to the control, for this mutant RAS colorectal carcinoma cell line.

FIG. 17 is a graph of relative tumour volume as a function of time (days) for mouse xenografts of the mutant RAS cell line SW620, for treatment with comparison compound XX-03 and for controls.

The data demonstrate that comparison compound XX-03 had relatively little effect, as compared to the control, for this mutant RAS colorectal carcinoma cell line.

FIG. 18 is a graph of relative tumour volume as a function of time (days) for mouse xenografts of the mutant RAS cell line SW620, for treatment with comparison compound XX-04 and for controls.

The data demonstrate that comparison compound XX-04 had relatively little effect, as compared to the control, for this mutant RAS colorectal carcinoma cell line.

FIG. 19 is a graph of relative tumour volume as a function of time (days) for mouse xenografts of the mutant BRAF cell line A375, for treatment with comparison compound XX-02 and for controls.

The data demonstrate that comparison compound XX-02 is at least to some degree effective, as compared to the control, for this mutant BRAF melanoma cell line.

The ratios of tumour volume (for treatment) to tumour volume (for control) (T/C) for mutant RAS SW620 xenografts are shown in the following table. A lower T/C ratio indicates a higher efficacy. Whereas the comparison compounds all have T/C ratios which indicate little or no efficacy, the claimed compounds AA-01 and BB-02 both have T/C ratios which demonstrate statistically significant efficacy.

TABLE 4

| Code | Ratio of: Tumour Volume (Treatment)/Tumour Volume (Control) (mutant RAS SW620 xenograft) |
| --- | --- |
| AA-01 | 0.34 |
| BB-02 | 0.66 |
| XX-01 | >1 |
| XX-02 | 0.95 |
| XX-03 | 0.97 |
| XX-04 | 0.87 |

The data for the claimed compounds demonstrate that, not only are the claimed compounds effective as BRAF inhibitors and against mutant BRAF tumours (for example, xenografts of the mutant BRAF melanoma cell line A375M; FIGS. 13 and 14), but, surprisingly and unexpectedly, the claimed compounds are also effective against mutant RAS tumours (for example, xenografts of the mutant RAS colorectal carcinoma cell line SW620; FIGS. 11 and 12). The surprising and unexpected activity of the claimed compounds against mutant RAS tumours could not be predicted from their known or expected BRAF inhibitory activity.

The data for the comparison compounds demonstrate that, although the comparison compounds are to some degree effective against mutant BRAF tumours (for example, xenografts of the mutant BRAF melanoma cell line A375M; FIG. 19), they have relatively little effect against mutant RAS tumours (for example, xenografts of the mutant RAS colorectal carcinoma cell line SW620; FIGS. 15, 16, 17, and 18).

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Bos, 1989, "ras oncogenes in human cancer: a review", Cancer Res., Vol. 49, pp. 4682-4689.

Downward, 2003, "Targeting RAS signalling pathways in cancer therapy", Nat. Rev. Cancer, Vol. 3, pp. 11-22.

Garnett et al., 2004, "Guilty as charged: B-RAF is a human oncogene", Cancer Cell, Vol. 6, pp. 313-319.

Gray-Schopfer et al., 2007, "Melanoma biology and new targeted therapy", Nature, Vol. 445, pp. 851-857.

Niculescu-Duvaz et al., 2006, "Imidazo[4,5-b]pyridine-2-one and oxazolo[4,5-b]pyridine-2-one compounds and analoges thereof as therapeutic compounds", international patent application publication number WO 2006/043090 A1 published 27 Apr. 2006.

Niculescu-Duvaz et al., 2007, "Imidazo[4,5-b]pyridine-2-one and oxazolo[4,5-b]pyridine-2-one compounds and analoges thereof as cancer therapeutic compounds", international patent application publication number WO 2007/125330 A1 published 8 Nov. 2007.

Niculescu-Duvaz et al., 2009, "Aryl-quinolyl compounds and their use", international patent application publication number WO 2009/130487 A1 published 29 Oct. 2009.

Solit et al., 2006, "BRAF mutation predicts sensitivity to MEK inhibition", Nature, Vol. 439, pp. 358-362.

Springer et al., 2009, "Pyrido[2,3-b]pyrazine-8-substituted compounds and their use", international patent application publication number WO 2009/077766 A1 published 25 Jun. 2009.

Wellbrock et al., 2004, "The RAF proteins take centre stage", Nature Reviews Molecular Cell Biology, Vol. 5, pp. 875-885.

Young et al., 2009, "Ras signaling and therapies", Adv. Cancer Res., Vol. 102, pp. 1-17.

The invention claimed is:

1. A method of treatment of mutant RAS cancer, comprising administering to a subject in need of treatment a therapeutically-effective amount of a compound selected from compounds of the following formula, and pharmaceutically acceptable salts thereof:

wherein -J- is independently:

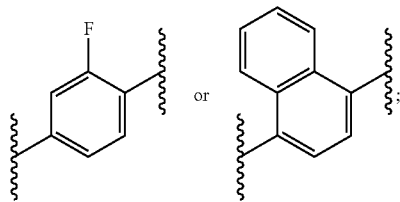 [SMILES: *c1ccc(*)c(F)c1 ; *c1ccc(*)c2ccccc12]

and wherein —R is independently: —H, -Me, —F, —Cl, —Br, or —I;
and wherein —R is positioned meta- or para- on the phenyl ring, wherein the mutant RAS cancer is mutant RAS melanoma or mutant RAS colorectal cancer.

2. A method according to claim 1, wherein the mutant RAS cancer is:
mutant RAS melanoma.

3. A method according to claim 1, wherein the mutant RAS cancer is:
mutant RAS colorectal cancer.

4. A method according to claim 1, wherein the compound is selected from compounds of the following formula, and pharmaceutically acceptable salts thereof:

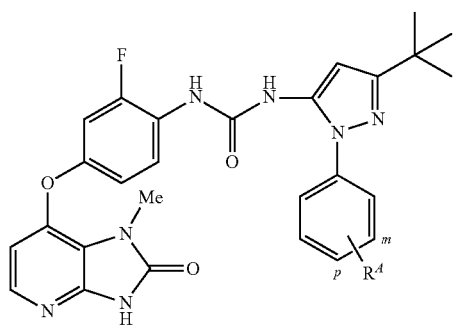

wherein —$R^A$ is independently —H, -Me, —F, —Cl, —Br, or —I; and
wherein —$R^A$ is positioned meta- or para- on the phenyl ring.

5. A method according to claim 4, wherein —$R^A$ is —H.
6. A method according to claim 4, wherein —$R^A$ is -Me.
7. A method according to claim 4, wherein —$R^A$ is —F.
8. A method according to claim 4, wherein —$R^A$ is —Cl.
9. A method according to claim 4, wherein the compound is selected from compounds of the following formula, and pharmaceutically acceptable salts thereof:

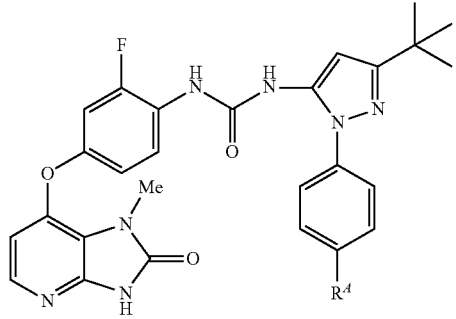

wherein —$R^A$ is independently —H, -Me, —F, —Cl, —Br, or —I.

10. A method according to claim 9, wherein —$R^A$ is independently —H, -Me, —F, or —Cl.

11. A method according to claim 4, wherein the compound is selected from compounds of the following formula, and pharmaceutically acceptable salts thereof:

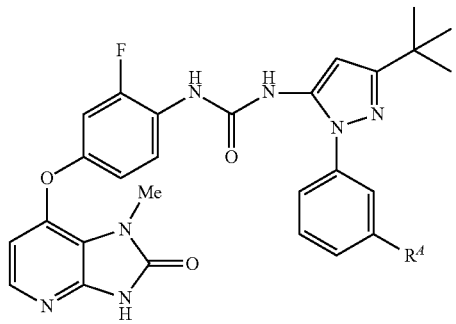

wherein —$R^A$ is independently —H, -Me, —F, —Cl, —Br, or —I.

12. A method according to claim 11, wherein —$R^A$ is independently —H, -Me, —F, or —Cl.

13. A method according to claim 4, wherein the compound is selected from the following compound and pharmaceutically acceptable salts thereof:

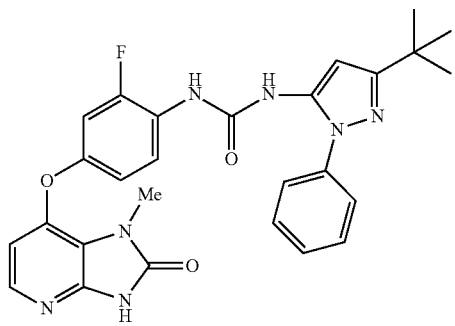

14. A method according to claim 4, wherein the compound is selected from the following compound and pharmaceutically acceptable salts thereof:

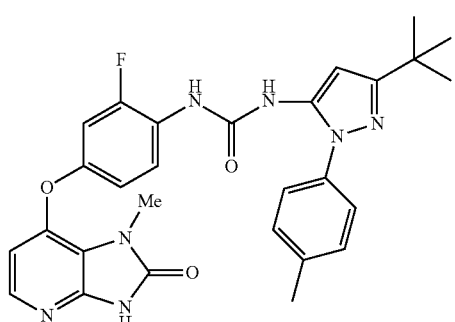

15. A method according to claim 4, wherein the compound is selected from the following compound and pharmaceutically acceptable salts thereof:

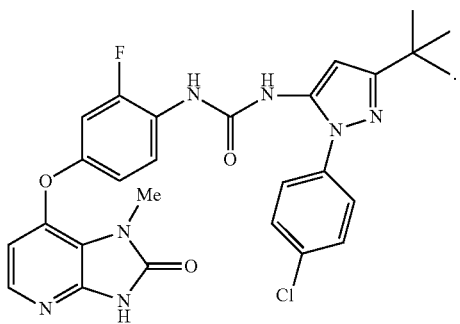

16. A method according to claim 4, wherein the compound is selected from the following compound and pharmaceutically acceptable salts thereof:

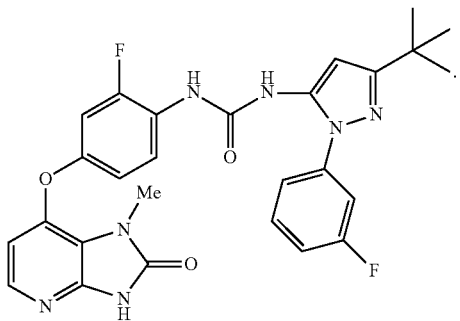 [SMILES: Cn1c(=O)[nH]c2nccc(Oc3ccc(NC(=O)Nc4cc(C(C)(C)C)nn4-c4cccc(F)c4)c(F)c3)c21]

17. A method according to claim 1, wherein the compound is selected from compounds of the following formula, and pharmaceutically acceptable salts thereof:

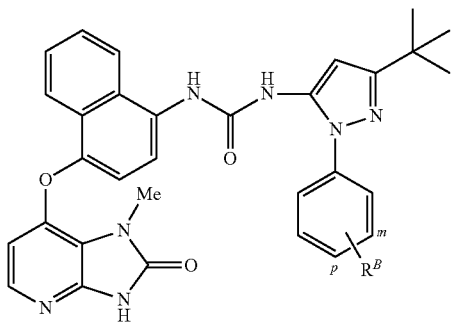

wherein —$R^B$ is independently —H, -Me, —F, —Cl, —Br, or —I; and wherein —$R^B$ is positioned meta- or para- on the phenyl ring.

18. A method according to claim 17, wherein —$R^B$ is independently —H, -Me, —F, or —Cl.

19. A method according to claim 17, wherein —$R^B$ is —H.

20. A method according to claim 17, wherein —$R^B$ is -Me.

21. A method according to claim 17, wherein —$R^B$ is —F.

22. A method according to claim 17, wherein —$R^B$ is —Cl.

23. A method according to claim 17, wherein the compound is selected from compounds of the following formula, and pharmaceutically acceptable salts thereof:

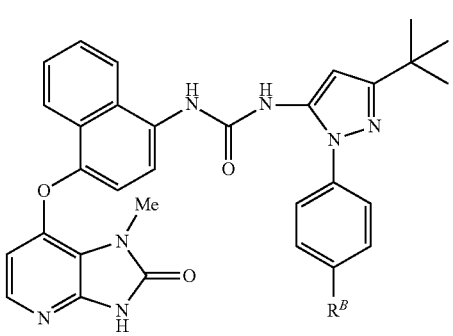

wherein —$R^B$ is independently —H, -Me, —F, —Cl, —Br, or —I.

24. A method according to claim 23, wherein —$R^B$ is independently —H, -Me, —F, or —Cl.

25. A method according to claim 17, wherein the compound is selected from compounds of the following formula, and pharmaceutically acceptable salts thereof:

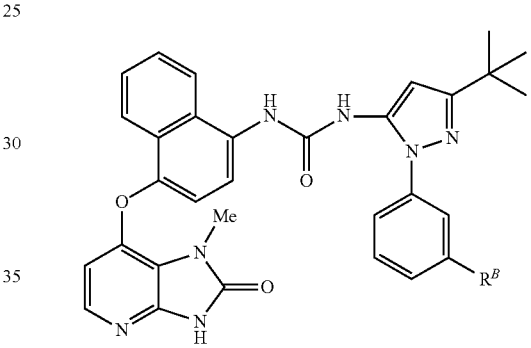

wherein —$R^B$ is independently —H, -Me, —F, —Cl, —Br, or —I.

26. A method according to claim 25, wherein —$R^B$ is independently —H, -Me, —F, or —Cl.

27. A method according to claim 17, wherein the compound is selected from the following compound, and pharmaceutically acceptable salts thereof:

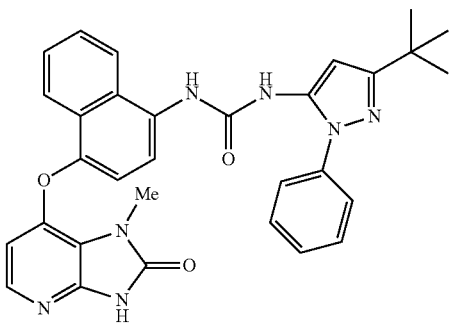

28. A method according to claim 17, wherein the compound is selected from the following compound, and pharmaceutically acceptable salts thereof:

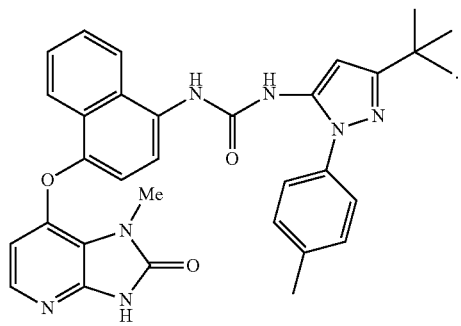
29. A method according to claim 17, wherein the compound is selected from the following compound, and pharmaceutically acceptable salts thereof:
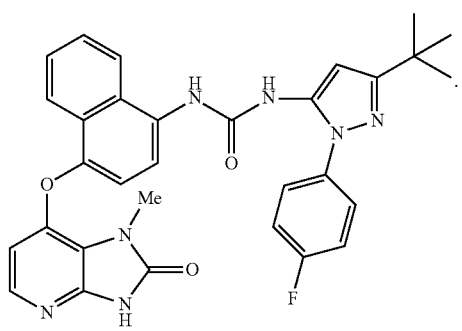 [SMILES: Cc1ccc(-n2nc(C(C)(C)C)cc2NC(=O)Nc2ccc(Oc3ccnc4[nH]c(=O)n(C)c34)c3ccccc23)cc1]
* * * * *